US012060364B2

(12) United States Patent
Yoo et al.

(10) Patent No.: US 12,060,364 B2
(45) Date of Patent: Aug. 13, 2024

(54) DIISOCYANATE COMPOUND HAVING ANHYDROSUGAR ALCOHOL CORE AND PREPARATION METHOD THEREFOR

(71) Applicant: SAMYANG CORPORATION, Seoul (KR)

(72) Inventors: Seung Hyun Yoo, Daejeon (KR); Hoon Ryu, Daejeon (KR); Jun Seop Im, Hwaseong-si (KR); Gwang Seok Song, Jeonju-si (KR); Won Hyun Jeon, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 828 days.

(21) Appl. No.: 17/266,150

(22) PCT Filed: Aug. 8, 2019

(86) PCT No.: PCT/KR2019/009952

§ 371 (c)(1),
(2) Date: Feb. 5, 2021

(87) PCT Pub. No.: WO2020/032611

PCT Pub. Date: Feb. 13, 2020

(65) Prior Publication Data

US 2021/0309670 A1 Oct. 7, 2021

(30) Foreign Application Priority Data

Aug. 8, 2018 (KR) ........................ 10-2018-0092550
Jun. 24, 2019 (KR) ........................ 10-2019-0074940
Jun. 28, 2019 (KR) ........................ 10-2019-0077877

(51) Int. Cl.
*C07D 493/04* (2006.01)
*C08G 18/77* (2006.01)

(52) U.S. Cl.
CPC ......... *C07D 493/04* (2013.01); *C08G 18/771* (2013.01)

(58) Field of Classification Search
CPC ............................ C07D 493/04; C08G 18/771
See application file for complete search history.

(56) References Cited

U.S. PATENT DOCUMENTS

2010/0130759 A1 5/2010 Gillet
2015/0148507 A1 5/2015 Gallagher et al.
2017/0044178 A1* 2/2017 Chen ................. C08G 18/3218

FOREIGN PATENT DOCUMENTS

| | | | |
|---|---|---|---|
| EP | 0 546 400 A2 | 6/1993 |
| KR | 10-1993-0012847 A | 7/1993 |
| KR | 10-1079518 B1 | 11/2011 |
| KR | 10-2012-0066904 A | 6/2012 |
| WO | WO 2012/081785 A1 | 6/2012 |

OTHER PUBLICATIONS

Fenouillot et al., "Polymers from renewable 1,4:3,6-dianhydrohexitols (isosorbide, isomannide and isoidide): A review", Progress in Polymer Science, vol. 35, 2010, pp. 578-622.
Hong et al., "Advanced materials from corn: isosorbide-based epoxy resins", Polymer Chemistry, vol. 5, 2014, pp. 5360-5368.
International Search Report issued in PCT/KR2019/009952 (PCT/ISA/210), dated Nov. 25, 2019.
Knölker et al., "A Novel Method for the Synthesis of Isocyanates Under Mild Conditions", Angew. Chem. Int. Ed. Engl., vol. 34, No. 22, 1995, pp. 2497-2500.

* cited by examiner

*Primary Examiner* — Timothy R Rozof
(74) *Attorney, Agent, or Firm* — Birch, Stewart, Kolasch & Birch, LLP

(57) ABSTRACT

The present invention relates to a diisocyanate compound having anhydrosugar alcohol core and a preparation method therefor and, more specifically, to a diisocyanate compound having anhydrosugar alcohol core and a preparation method therefor, wherein the diisocyanate compound is prepared through a reaction with a nitrile compound, a hydrogenation reaction, and an end-group substitution reaction while a recyclable, plant-based anhydrosugar alcohol or anhydrosugar alcohol-alkylene glycol is used as a raw material, and the diisocyanate compound can be utilized in various fields, such as soft or hard polyurethane expanded foams, molded foams, coating, adhesives or glues, fibers, and polymer synthesis.

20 Claims, No Drawings

DIISOCYANATE COMPOUND HAVING ANHYDROSUGAR ALCOHOL CORE AND PREPARATION METHOD THEREFOR

TECHNICAL FIELD

The present invention relates to a diisocyanate compound having anhydrosugar alcohol core and a method for preparing the same, and more specifically, to a diisocyanate compound which is prepared by a reaction of a renewable plant-based anhydrosugar alcohol or anhydrosugar alcohol-alkylene glycol as a raw material with a nitrile compound, hydrogenation and end-group substitution reaction, and can be used in various fields such as soft or hard polyurethane foam, mold foam, coating, tackifier or adhesive, fiber and polymer synthesis and a method for preparing the same.

BACKGROUND ART

Hydrogenated sugar (also known as "sugar alcohol") refers to a compound obtained by adding hydrogen to the reducing terminal group of a saccharide. Generally, it has the formula $HOCH_2(CHOH)_nCH_2OH$ (wherein n is an integer of 2 to 5) and is classified into tetritol, pentitol, hexitol and heptitol (having 4, 5, 6 and 7 carbon atoms, respectively) depending on the number of carbon atoms. Among them, hexitol having 6 carbon atoms includes sorbitol, mannitol, iditol, galactitol and the like, and sorbitol and mannitol are particularly useful substances.

Anhydrosugar alcohol has a diol form with two hydroxyl groups in the molecule and can be prepared by utilizing hexitol derived from starch (for instance, Korean Patent No. 10-1079518 and Korean Patent Laid-open Publication No. 10-2012-0066904). Since anhydrosugar alcohol is an eco-friendly substance derived from renewable natural resources, there has been much interest for a long time, and studies on the production method have been carried out. Among these anhydrosugar alcohols, isosorbide prepared from sorbitol presently has the largest industrial application range.

Anhydrosugar alcohol is widely used in the treatment of cardiac and vascular diseases, adhesives for patches, drugs for mouthwash and the like, solvents for compositions in the cosmetics industry and emulsifiers in the food industry. In addition, it is possible to increase the glass transition temperature of a polymer such as polyester, PET, polycarbonate, polyurethane and epoxy resin, and to improve the strength of these materials, and it is also very useful in the plastics industry such as bioplastics since it is an eco-friendly material derived from natural materials. It is also known to be used as adhesives, eco-friendly plasticizers, biodegradable polymers and an eco-friendly solvent for water-soluble lacquers.

Recently, while the demand for eco-friendly chemicals is increasing rapidly due to environmental pollution, since anhydrosugar alcohol is a renewable low-cost raw material derived from plants, it is necessary to develop bio-based monomers and polymers that can be used in various fields such as soft or hard polyurethane foam, mold foam, coating, tackifier or adhesive, fiber and polymer synthesis.

CONTENTS OF THE INVENTION

Problems to be Solved

The purpose of the present invention is to provide a diisocyanate compound which is prepared by a reaction of a renewable plant-based anhydrosugar alcohol or anhydrosugar alcohol-alkylene glycol as a raw material with a nitrile compound, hydrogenation and end-group substitution reaction, and can be used in various fields such as soft or hard polyurethane foam, mold foam, coating, tackifier or adhesive, fiber and polymer synthesis and a method for preparing the same.

Technical Means

In order to achieve the technical purpose, the present invention provides a compound represented by the following Formula A:

$$X—Y—O—M—O—Y'—X \qquad \text{[Formula A]}$$

in Formula A, each X is independently $—CH_2NCO$,

Y is $—[CH_2CHR_1O]_m—CHR_2CHR_3—$,

Y' is $—[CH_2CHR_1O]_n—CHR_2CHR_3—$, wherein each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and M is a divalent organic group derived from anhydrosugar alcohol.

In another aspect, the present invention provides a method for preparing a compound represented by Formula A, comprising (1) a step of performing Michael reaction of anhydrosugar alcohol or anhydrosugar alcohol-alkylene glycol with a nitrile compound; (2) a step of adding hydrogen to the compound obtained from the Michael reaction; and (3) a step of converting the terminal group of the compound obtained from the hydrogenation into an isocyanate:

$$X—Y—O—M—O—Y'—X \qquad \text{[Formula A]}$$

in Formula A, each X is independently $—CH_2NCO$,

Y is $—[CH_2CHR_{10}]_m—CHR_2CHR_3—$, wherein each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and M is a divalent organic group derived from anhydrosugar alcohol.

In still another aspect, the present invention provides a polymer comprising the above compound represented by Formula A.

Effect of the Invention

Since the diisocyanate compound according to the present invention having anhydrosugar alcohol core or anhydrosugar alcohol core and alkylene oxide extension is prepared by a reaction of a renewable plant-based anhydrosugar alcohol or anhydrosugar alcohol-alkylene glycol as a raw material with a nitrile compound, hydrogenation and end-group substitution reaction, it is eco-friendly and can reduce manufacturing cost. The diisocyanate compound of the present invention may be used in various forms such as being used singly, with introducing a trivalent or higher functional group through a cyclization reaction or mixing with a petroleum-based isocyanate compound. For example, it can be used in various fields such as soft or hard polyurethane foam, mold foam, coating, tackifier or adhesive, fiber and polymer synthesis.

CONCRETE MODE FOR CARRYING OUT THE INVENTION

The present invention is explained in more detail below.

The present invention provides a compound represented by the following Formula A:

X—Y—O—M—O—Y'—X [Formula A]

in Formula A, each X is independently —$CH_2NCO$,

Y is —$[CH_2CHR_1O]_m$—$CHR_2CHR_3$—,

Y' is —$[CH_2CHR_1O]_n$—$CHR_2CHR_3$—, wherein each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and M is a divalent organic group derived from anhydrosugar alcohol.

Hydrogenated sugar (also known as "sugar alcohol") refers to a compound obtained by adding hydrogen to the reducing terminal group of a saccharide. Generally, it has the formula $HOCH_2(CHOH)_nCH_2OH$ (wherein n is an integer of 2 to 5) and is classified into tetritol, pentitol, hexitol and heptitol (having 4, 5, 6 and 7 carbon atoms, respectively) depending on the number of carbon atoms.

Among them, hexitol having 6 carbon atoms includes sorbitol, mannitol, iditol, galactitol and the like, and sorbitol and mannitol are particularly useful substances.

Anhydrosugar alcohol has a diol form with two hydroxyl groups in the molecule and can be prepared by utilizing hexitol derived from starch (for instance, Korean Patent No. 10-1079518 and Korean Patent Laid-open Publication No. 10-2012-0066904). Since anhydrosugar alcohol is an eco-friendly substance derived from renewable natural resources, there has been much interest for a long time, and studies on the production method have been carried out. Among these anhydrosugar alcohols, isosorbide prepared from sorbitol presently has the largest industrial application range.

In the compound represented by Formula A of the present invention, M may be a divalent organic group derived from an anhydrosugar alcohol such as isosorbide (1,4:3,6-dianhydroisorbitol), isomannide (1,4:3,6-dianhydromannitol) or isoidide (1,4:3,6-dianhydroiditol). In one embodiment, M may be selected from the following formula.

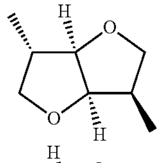 ; 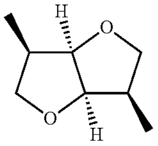 ;

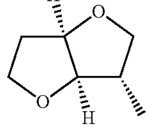

In the compound represented by Formula A of the present invention, each $R_1$ is independently hydrogen, alkyl or aryl, and each of $R_2$ and $R_3$ is independently hydrogen, alkyl, aryl, heteroaryl or cycloalkyl.

The alkyl may be, for example, a substituted or unsubstituted linear alkyl having 1 to 10 carbon atoms (more specifically 1 to 6); or a substituted or unsubstituted branched alkyl having 3 to 10 carbon atoms (more specifically 3 to 6). The aryl may be, for example, a substituted or unsubstituted monocyclic aryl, polycyclic aryl or fused cyclic aryl having carbon number 6 to 14 (more specifically 6 to 12). In addition, the heteroaryl may be, for example, a substituted or unsubstituted 5- to 12-membered (more specifically 5- to 10-membered) monocyclic heteroaryl, polycyclic heteroaryl or fused cyclic heteroaryl comprising at least one heteroatom selected from N, O or S. The cycloalkyl may be, for example, a substituted or unsubstituted cycloalkyl having 3 to 8 carbon atoms (more specifically 3 to 6).

The groups can be substituted with, for example, one or more substituents selected from $C_1$-$C_{10}$ alkyl (e.g., methyl, ethyl, propyl, butyl, etc.) or $C_6$-$C_{10}$ aryl (e.g., phenyl, benzyl, tolyl, etc.).

In Formula A, each of m and n is independently an integer of 0 to 15, so when both m and n are 0, a renewable plant-based anhydrosugar alcohol is used as a raw material, and the compound represented by Formula A means a compound that does not comprise an alkylene oxide extension between an anhydrosugar alcohol core and an isocyanate group (referred to herein as a "diisocyanate compound having an anhydrosugar alcohol core"). In addition, when m+n is an integer of 1 to 25, a renewable plant-based anhydrosugar alcohol-alkylene glycol is used as a raw material, and the compound represented by Formula A means a compound comprising an alkylene oxide extension between the anhydrosugar alcohol core and an isocyanate group (referred to herein as a "diisocyanate compound having an anhydrosugar alcohol core and an alkylene oxide extension").

In one embodiment, when both m and n are 0, that is, when the compound represented by Formula A of the present invention is a diisocyanate compound having an anhydrosugar alcohol core, the compound represented by Formula A may be a compound represented by the following Formula 3 (isosorbide diisocyanate compound):

[Formula 3]

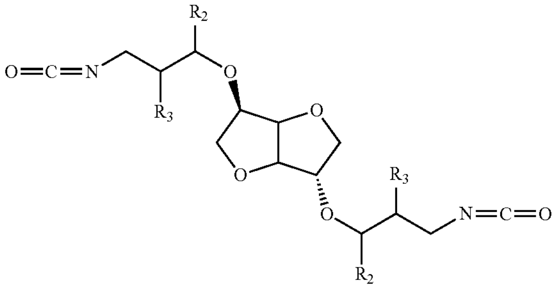

in Formula 3, each of $R_2$ and $R_3$ is independently hydrogen, alkyl, aryl, heteroaryl or cycloalkyl.

In one embodiment, an example of the compound represented by Formula 3 may be a compound represented by Formulas 3-1 to 3-6, but it is not limited thereto.

[Formula 3-1]

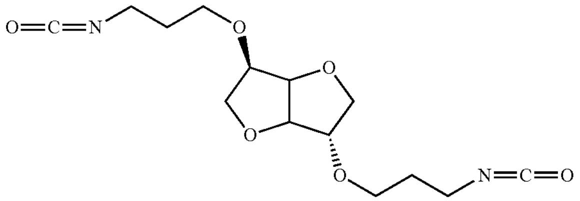

[Formula 3-2]

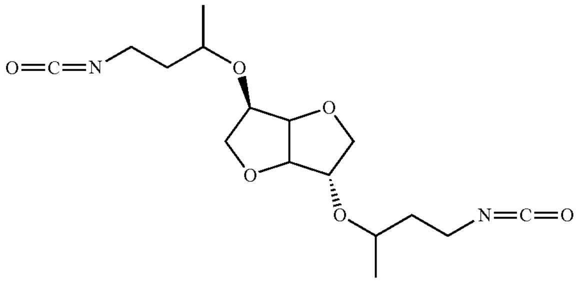

[Formula 3-3]

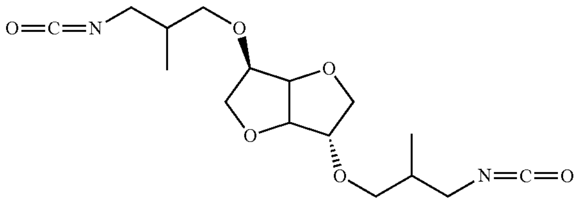

[Formula 3-4]

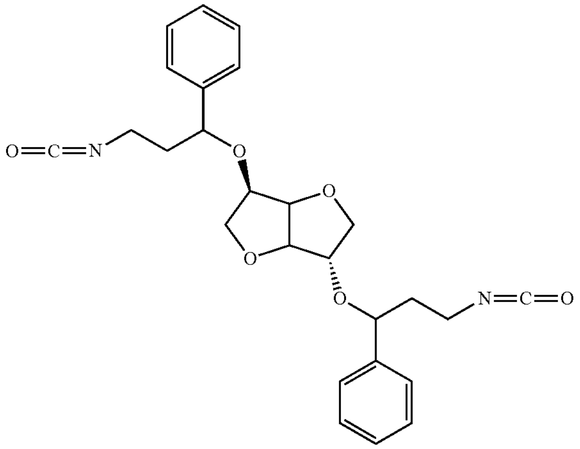

-continued

[Formula 3-5]

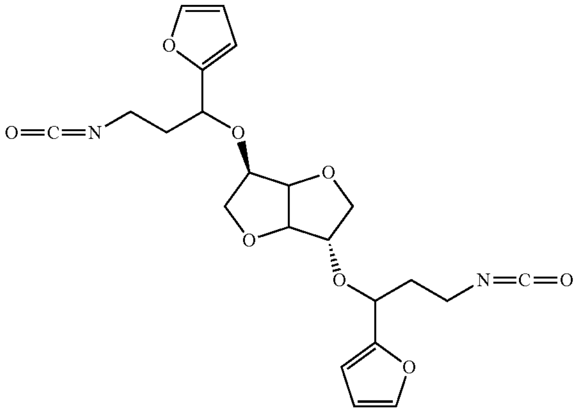

[Formula 3-6]

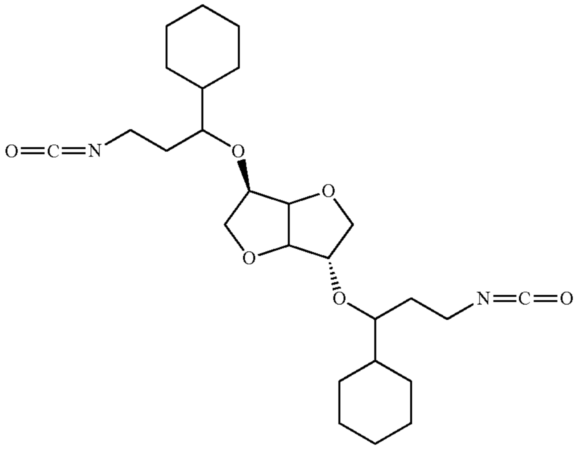

In one embodiment, when both m and n are 0, that is, when the compound represented by Formula A of the present invention is a diisocyanate compound having an anhydrosugar alcohol core, the compound represented by Formula A may be a compound represented by the following Formula 6 (isomannide diisocyanate compound):

[Formula 6]

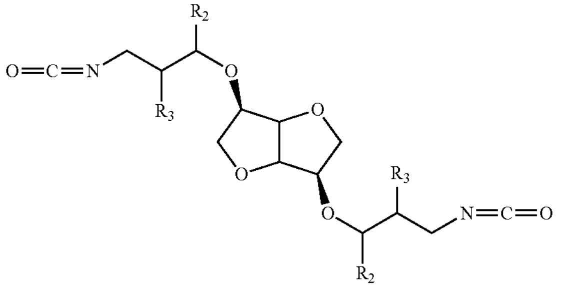

in Formula 6, each of $R_2$ and $R_3$ is independently hydrogen, alkyl, aryl, heteroaryl or cycloalkyl.

In one embodiment, an example of the compound represented by Formula 6 may be a compound represented by Formulas 6-1 to 6-6, but it is not limited thereto.

[Formula 6-1]

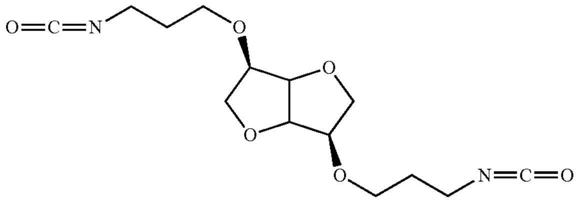

[Formula 6-2]

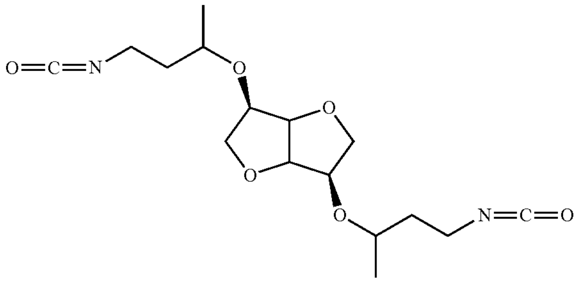

[Formula 6-3]

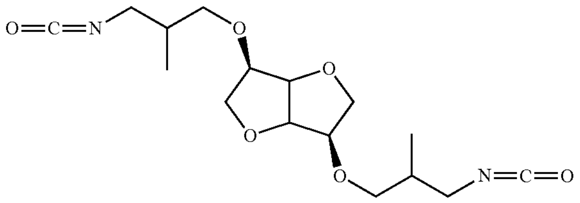

[Formula 6-4]

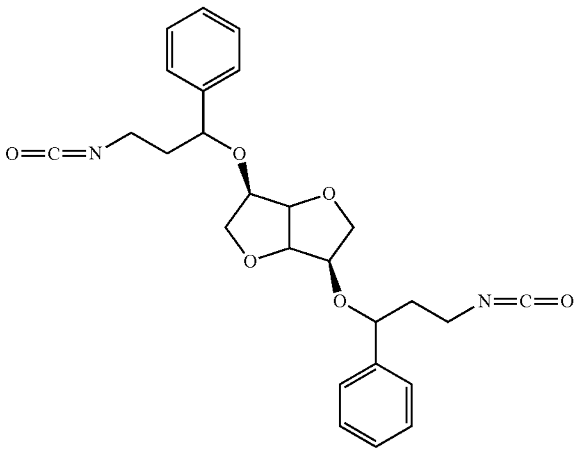

-continued

[Formula 6-5]

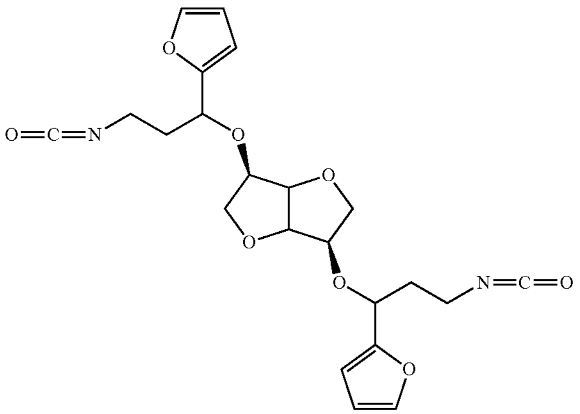

[Formula 6-6]

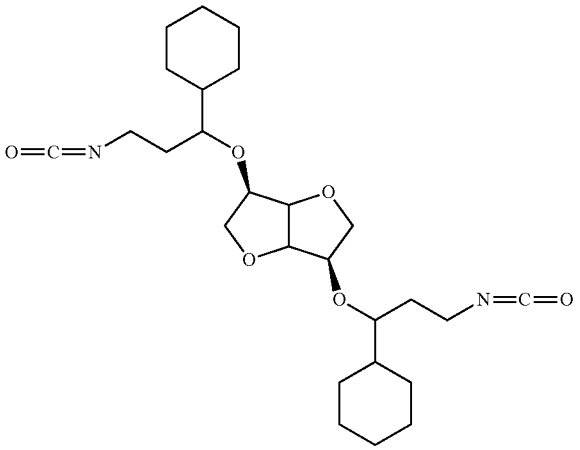

In one embodiment, when both m and n are 0, that is, when the compound represented by Formula A of the present invention is a diisocyanate compound having an anhydrosugar alcohol core, the compound represented by Formula A may be a compound represented by the following Formula 9 (isoidide diisocyanate compound):

[Formula 9]

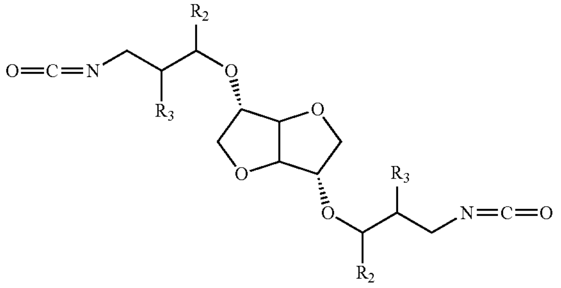

in Formula 9, each of $R_2$ and $R_3$ is independently hydrogen, alkyl, aryl, heteroaryl or cycloalkyl.

In one embodiment, an example of the compound represented by Formula 9 may be a compound represented by Formulas 9-1 to 9-6, but it is not limited thereto.

-continued

[Formula 9-1]

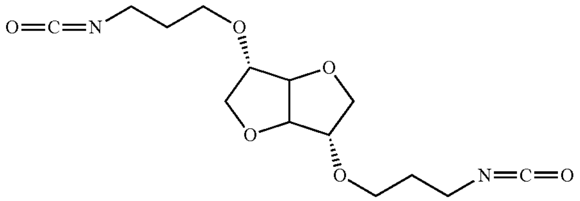

[Formula 9-2]

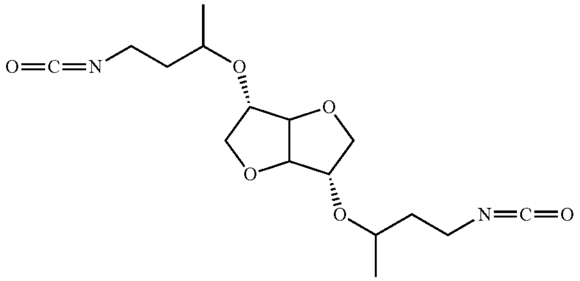

[Formula 9-3]

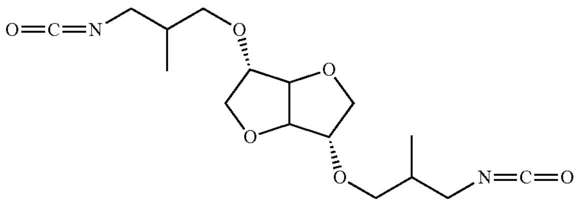

[Formula 9-4]

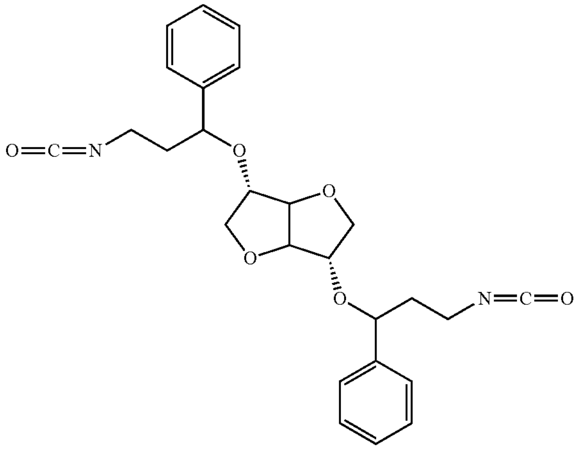

[Formula 9-5]

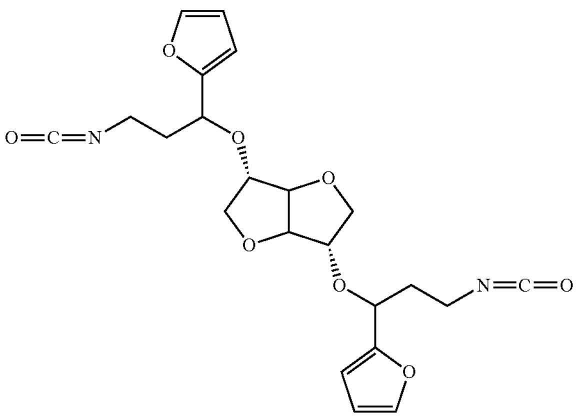

[Formula 9-6]

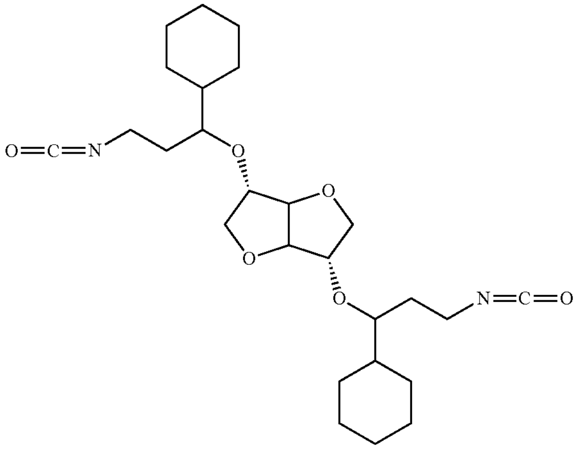

In one embodiment, when m+n is an integer of 1 to 25, that is, when the compound represented by Formula A of the present invention is a diisocyanate compound having an anhydrosugar alcohol core and an alkylene oxide extension, the compound represented by Formula A may be a compound represented by the following Formula 12 (isosorbide-alkylene glycol-diisocyanate compound):

[Formula 12]

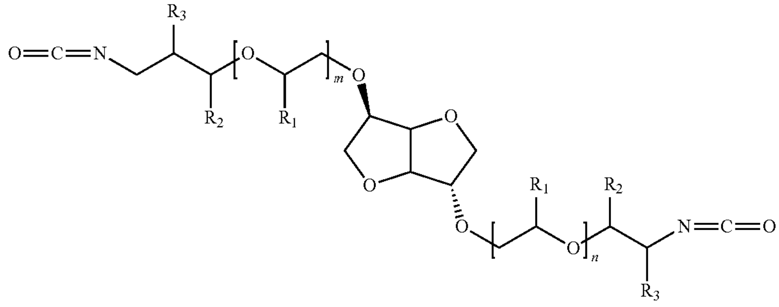

in Formula 12, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

In one embodiment, an example of the compound represented by Formula 12 may be a compound represented by Formulas 12-1 to 12-6, but it is not limited thereto.

[Formula 12-1]

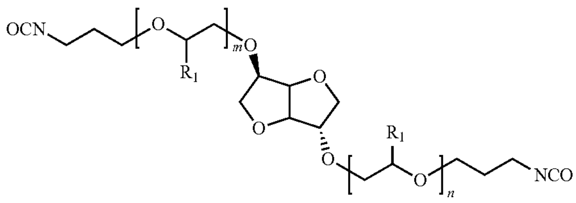

[Formula 12-2]

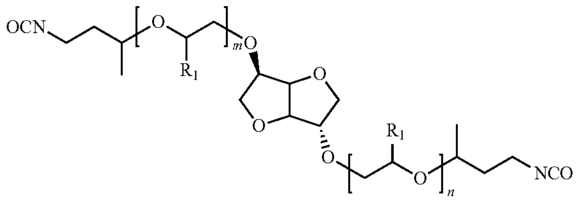

[Formula 12-3]

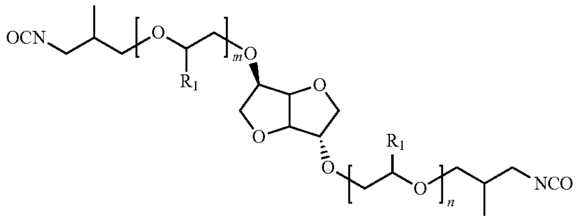

-continued

[Formula 12-4]

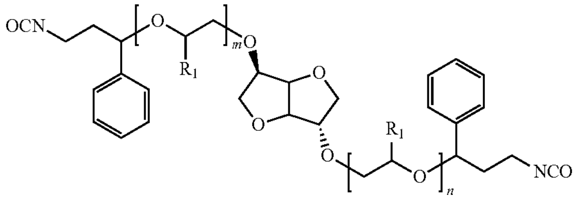

[Formula 12-5]

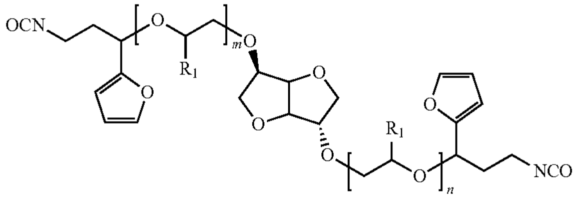

[Formula 12-6]

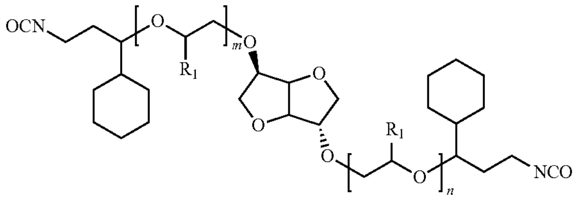

in Formulas 12-1 to 12-6.

each $R_1$ is independently hydrogen, alkyl or aryl, each of m and n is independently an integer of 0 to 15, and m+n is an integer from 1 to 25.

In one embodiment, when m+n is an integer of 1 to 25, that is, when the compound represented by Formula A of the present invention is a diisocyanate compound having an anhydrosugar alcohol core and an alkylene oxide extension, the compound represented by Formula A may be a compound represented by the following Formula 15 (isomannide-alkylene glycol-diisocyanate compound):

[Formula 15]

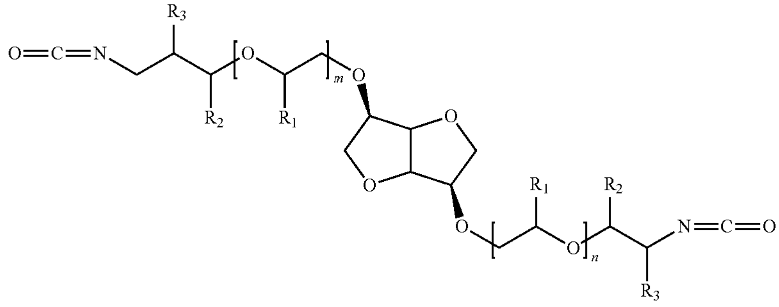

in Formula 15, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

In one embodiment, an example of the compound represented by Formula 15 may be a compound represented by Formulas 15-1 to 15-6, but it is not limited thereto.

[Formula 15-1]

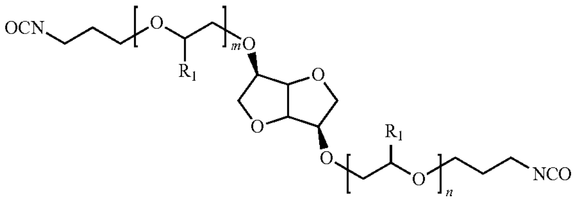

[Formula 15-2]

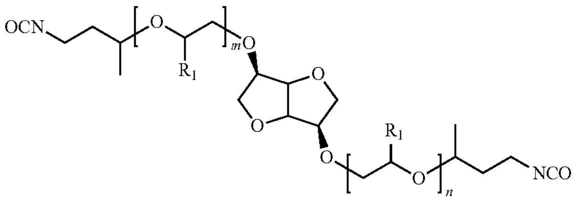

[Formula 15-3]

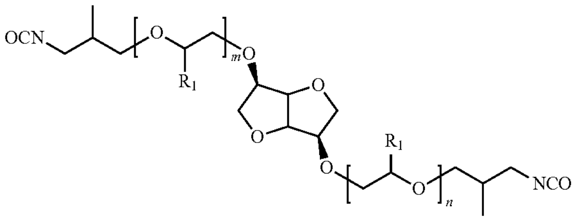

-continued

[Formula 15-4]

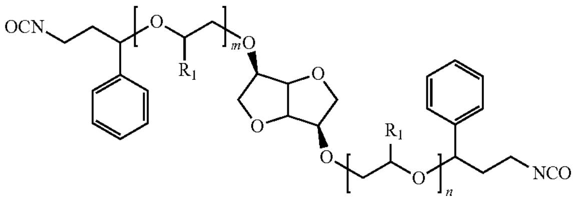

[Formula 15-5]

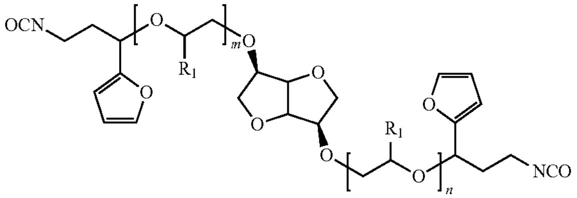

[Formula 15-6]

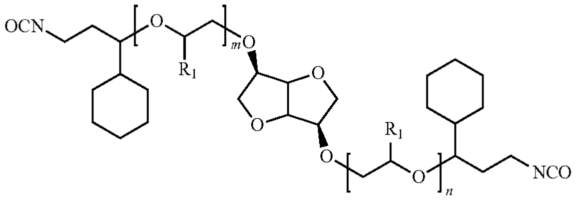

in Formulas 15-1 to 15-6, each $R_1$ is independently hydrogen, alkyl or aryl, each of m and n is independently an integer of 0 to 15, and m+n is an integer from 1 to 25.

In one embodiment, when m+n is an integer of 1 to 25, that is, when the compound represented by Formula A of the present invention is a diisocyanate compound having an anhydrosugar alcohol core and an alkylene oxide extension, the compound represented by Formula A may be a compound represented by the following Formula 18 (isoidide-alkylene glycol-diisocyanate compound):

[Formula 18]

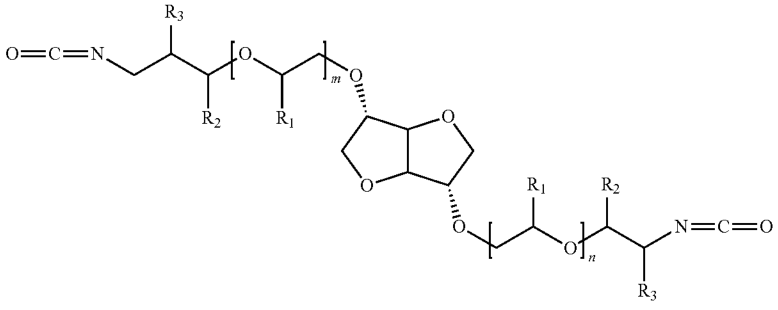

in Formula 18, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

In one embodiment, an example of the compound represented by Formula 18 may be a compound represented by Formulas 18-1 to 18-6, but it is not limited thereto.

[Formula 18-1]

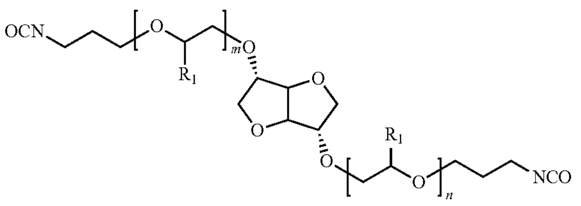

[Formula 18-2]

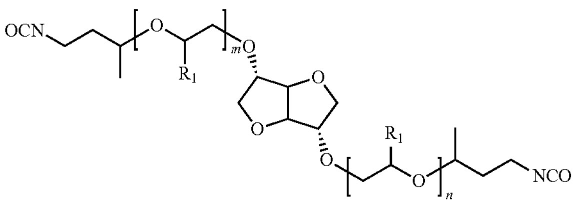

[Formula 18-3]

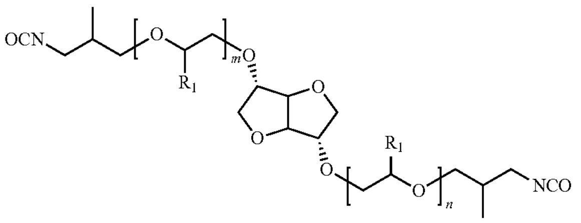

[Formula 18-4]

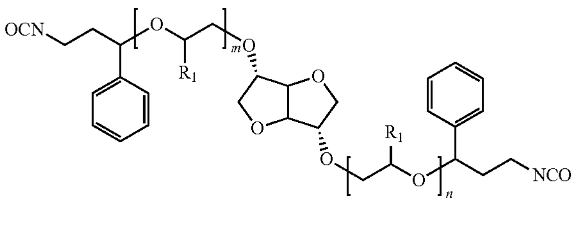

-continued

[Formula 18-5]

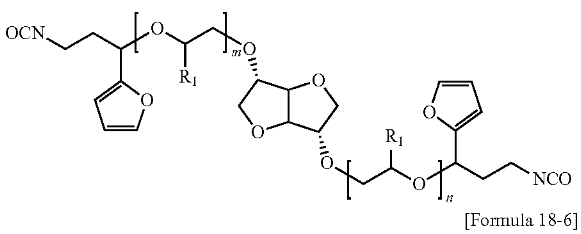

[Formula 18-6]

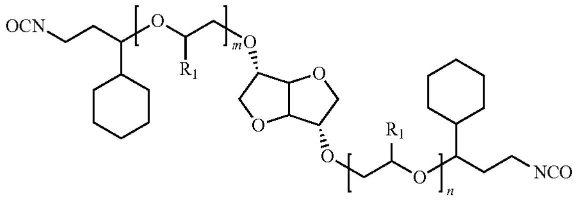

in Formulas 18-1 to 18-6, each $R_1$ is independently hydrogen, alkyl or aryl, each of m and n is independently an integer of 0 to 15, and m+n is an integer from 1 to 25.

In another aspect, the present invention provides a method for preparing a compound represented by Formula A, comprising (1) a step of performing Michael reaction of anhydrosugar alcohol or anhydrosugar alcohol-alkylene glycol with a nitrile compound; (2) a step of adding hydrogen to the compound obtained from the Michael reaction; and (3) a step of converting the terminal group of the compound obtained from the hydrogenation into an isocyanate:

X—Y—O—M—O—Y'—X [Formula A]

in Formula A, each X is independently —$CH_2NCO$,

Y is —$[CH_2CHR_1O]_m$—$CHR_2CHR_3$—,

Y' is —$[CH_2CHR_1O]_n$—$CHR_2CHR_3$—, wherein each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and M is a divalent organic group derived from anhydrosugar alcohol.

In one embodiment, when the reaction starting material is anhydrosugar alcohol-alkylene glycol, the method for preparing the compound represented by Formula A may further comprise a step of preparing anhydrosugar alcohol-alkylene glycol by adding alkylene oxide to both ends of the anhydrosugar alcohol, prior to step (1) of performing the Michael reaction. In this case, 1 to 30 molar equivalents of alkylene oxide may be added to 1 molar equivalent of anhydrosugar alcohol. If the molar equivalent of the alkylene oxide is too low, the yield of the anhydrosugar alcohol-alkylene oxide adduct is lowered. On the other hand, if the molar equivalent is too high, it is difficult to expect additional effects and the manufacturing cost increases.

In one embodiment, the alkylene oxide may be a linear alkylene oxide having 2 to 8 carbon atoms or a branched alkylene oxide having 3 to 8 carbon atoms, and more specifically, may be selected from ethylene oxide, propylene oxide or a combination thereof.

In one embodiment, the alkylene oxide addition reaction may be carried out at a temperature of 100 to 200° C., preferably 120 to 160° C., for 1 to 10 hours, preferably 2 to 4 hours.

In step (1) of performing Michael reaction of anhydrosugar alcohol or anhydrosugar alcohol-alkylene glycol with a nitrile compound, the anhydrosugar alcohol may be isosorbide (1,4:3,6-dianhydroisorbitol), isomannide (1,4:3,6-dianhydromannitol), isoidide (1,4:3,6-dianhydroiditol) or a combination thereof.

The nitrile compound used in the preparing method of the present invention may be selected from the group consisting of acrylonitrile, crotononitrile, methacrylonitrile, cinnamonitrile, 3-(furan-2-yl)prop-2-enenitrile, cyclohexaneacrylonitrile or a combination thereof, but it is not limited thereto.

In performing Michael reaction of anhydrosugar alcohol or anhydrosugar alcohol-alkylene glycol with a nitrile compound, 1 to 10 molar equivalents, more preferably 2 to 5 molar equivalents and even more preferably 2 to 3 molar equivalents of a nitrile compound are reacted with 1 molar equivalent of anhydrosugar alcohol or anhydrosugar alcohol-alkylene glycol. If the molar equivalent of the nitrile compound is too low, the yield of the compound represented by Formula A decreases. If the molar equivalent of the nitrile compound is too high, it is difficult to expect additional effects and the manufacturing cost increases.

The Michael reaction may be performed in the presence of a base catalyst, and is not particularly limited, but Michael reaction may be performed in the presence of 0.005 to 0.05 molar equivalent of a base catalyst with respect to 1 molar equivalent of anhydrosugar alcohol or anhydrosugar alcohol-alkylene glycol. If the content of the base catalyst is too low, the reaction rate of the Michael reaction is slowed. On the other hand, if the content of the base catalyst is too high, it is difficult to expect additional effects and the manufacturing cost increases.

Although the type of the base catalyst is not particularly limited—for example, alkali metal hydroxides (specifically, a hydroxide of Li, Na, K, Rb or Cs, etc.), alkaline earth metal hydroxides (specifically, a hydroxide of Mg, Ca, Sr or Ba, etc.), carbonates of alkali metals (specifically, carbonates of Li, Na, K, Rb or Cs, etc.), alcoholates of alkali metals or alkaline earth metals (specifically, sodium methylate, sodium ethylate or potassium t-butylate, etc.) or a basic organic catalyst (specifically, 1,8-diazabicyclo[5.4.0]undec-7-ene or 4-(dimethylamino)pyridine, etc.)-preferably a basic organic catalyst may be used.

When a basic organic catalyst is used as the base catalyst, the rate of Michael reaction (nitrile addition reaction) is accelerated compared to the basic inorganic catalyst, thereby solving a serious heat generation problem due to accumulation of unreacted raw materials during the addition of a nitrile compound.

Step (1) of performing the Michael reaction of the anhydrosugar alcohol or anhydrosugar alcohol-alkylene glycol with the nitrile compound can further comprise a step of stirring the product of the Michael reaction for 1 to 10 hours. If the stirring time is too short, the yield of the compound represented by Formula A may be lowered. On the other hand, if the stirring time is too long, it is difficult to expect additional effects.

The product of the Michael reaction may be cooled to room temperature after the stirring step, and the cooled product of the Michael reaction may be diluted with an organic solvent (e.g., ethyl acetate, dichloromethane, 2-methyltetrahydrofuran, diethyl ether, etc.). After dilution, it can be washed sequentially with an aqueous hydrochloric acid solution, an aqueous sodium hydroxide solution and distilled water. After that, the step of concentrating under reduced pressure may be further performed.

In the method for preparing the compound represented by Formula A, the anhydrosugar alcohol, anhydrosugar alcohol-alkylene glycol, the nitrile compound, and $R_1$ to $R_3$ are the same as described above.

In the preparing method of the present invention, the compound obtained from the Michael reaction in step (1) may be a compound represented by the following formula A':

X'—Y—O—M—O—Y'—X" [Formula A']

in Formula A',

X' is —CN,

Y is $—[CH_2CHR_{10}]_m—CHR_2CHR_3—$, wherein each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and M is a divalent organic group derived from anhydrosugar alcohol.

In Formula A', the alkyl may be, for example, a substituted or unsubstituted linear alkyl having 1 to 10 carbon atoms (more specifically 1 to 6); or a substituted or unsubstituted branched alkyl having 3 to 10 carbon atoms (more specifically 3 to 6). The aryl may be, for example, a substituted or unsubstituted monocyclic aryl, polycyclic aryl or fused cyclic aryl having carbon number 6 to 14 (more specifically 6 to 12). In addition, the heteroaryl may be, for example, a substituted or unsubstituted 5- to 12-membered (more specifically 5- to 10-membered) monocyclic heteroaryl, polycyclic heteroaryl or fused cyclic heteroaryl comprising at least one heteroatom selected from N, O or S. The cycloalkyl may be, for example, a substituted or unsubstituted cycloalkyl having 3 to 8 carbon atoms (more specifically 3 to 6).

The groups can be substituted with, for example, one or more substituents selected from $C_1$-$C_{10}$ alkyl (e.g., methyl, ethyl, propyl, butyl, etc.) or $C_6$-$C_{10}$ aryl (e.g., phenyl, benzyl, tolyl, etc.).

In Formula A', each of m and n is independently an integer of 0 to 15, so when both m and n are 0, a renewable plant-based anhydrosugar alcohol is used as a raw material, and the compound represented by Formula A' means a compound that does not comprise an alkylene oxide extension between an anhydrosugar alcohol core and a nitrile group (referred to herein as a "dinitrile compound having an anhydrosugar alcohol core"). In addition, when m+n is an integer of 1 to 25, a renewable plant-based anhydrosugar alcohol-alkylene glycol is used as a raw material, and the compound represented by Formula A' means a compound comprising an alkylene oxide extension between the anhydrosugar alcohol core and a nitrile group (referred to herein as a "dinitrile compound having an anhydrosugar alcohol core and an alkylene oxide extension").

In one embodiment, when both m and n are 0, that is, when the compound represented by Formula A' of the present invention is a dinitrile compound having an anhydrosugar alcohol core, the compound represented by Formula A' may be a compound represented by the following Formula 1 (isosorbide dinitrile compound):

[Formula 1]

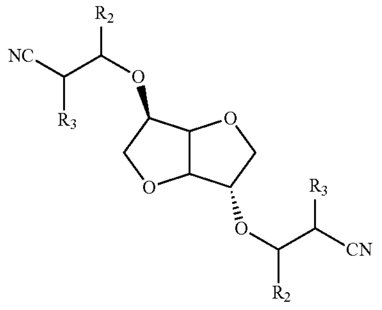

in Formula 1, each of $R_2$ and $R_3$ is independently hydrogen, alkyl, aryl, heteroaryl or cycloalkyl.

In one embodiment, an example of the compound represented by Formula 1 may be a compound represented by Formulas 1-1 to 1-6, but it is not limited thereto.

[Formula 1-1]

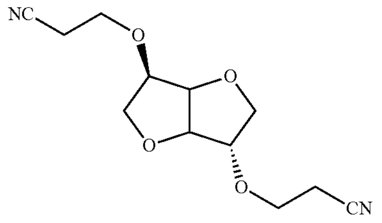

[Formula 1-2]

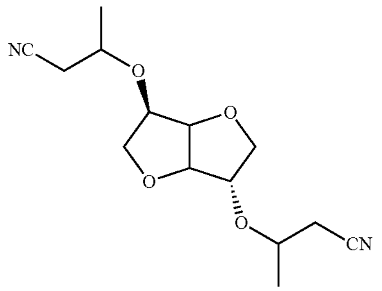

[Formula 1-3]

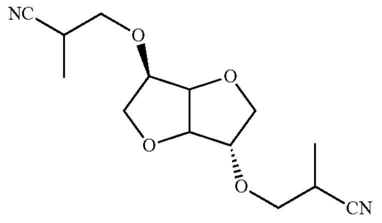

-continued

[Formula 1-4]

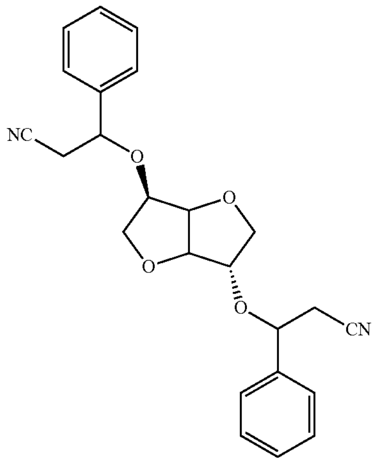

[Formula 1-5]

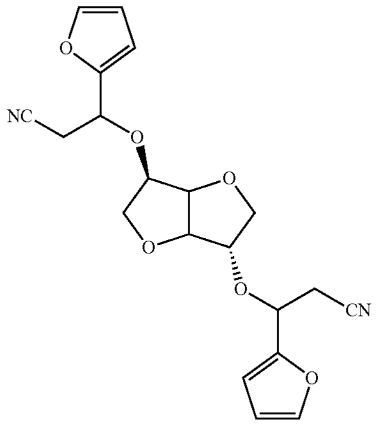

[Formula 1-6]

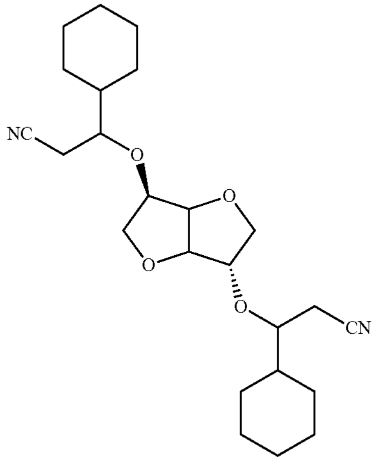

In one embodiment, when both m and n are 0, that is, when the compound represented by Formula A' of the present invention is a dinitrile compound having an anhydrosugar alcohol core, the compound represented by Formula A' may be a compound represented by the following Formula 4 (isomannide dinitrile compound):

[Formula 4]

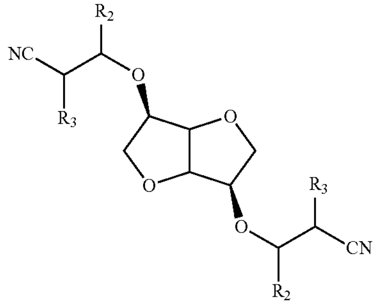

in Formula 4, each of $R_2$ and $R_3$ is independently hydrogen, alkyl, aryl, heteroaryl or cycloalkyl.

In one embodiment, an example of the compound represented by Formula 4 may be a compound represented by Formulas 4-1 to 4-6, but it is not limited thereto.

[Formula 4-1]

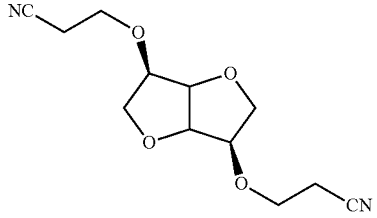

[Formula 4-2]

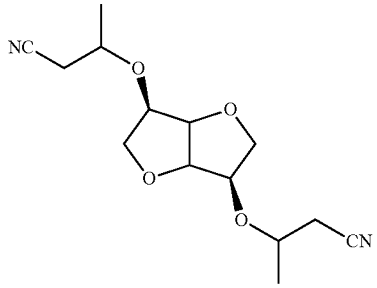

[Formula 4-3]

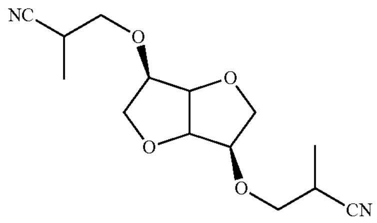

-continued

[Formula 4-4]

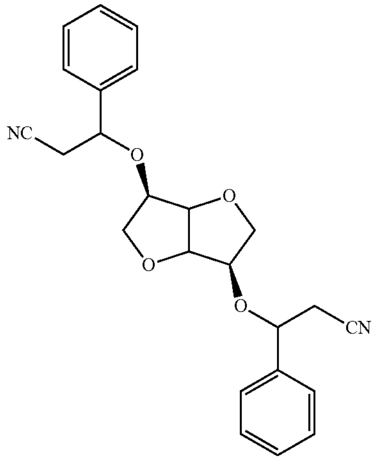

[Formula 4-5]

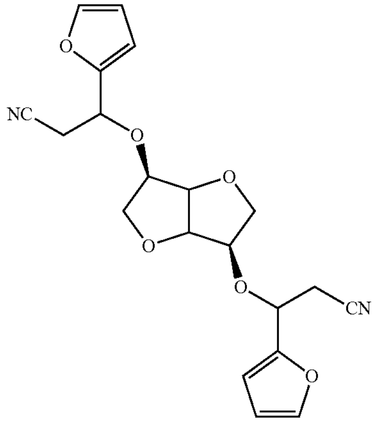

[Formula 4-6]

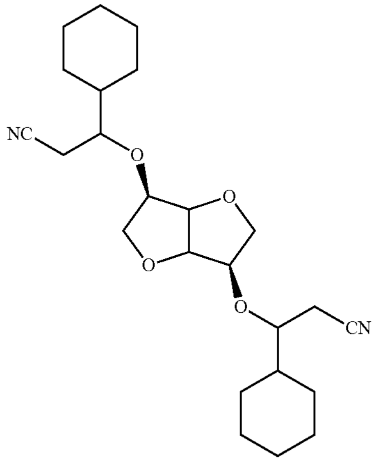

In one embodiment, when both m and n are 0, that is, when the compound represented by Formula A' of the present invention is a dinitrile compound having an anhydrosugar alcohol core, the compound represented by Formula A' may be a compound represented by the following Formula 7 (isoidide dinitrile compound):

[Formula 7]

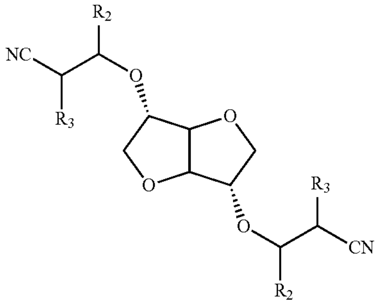

in Formula 7, each of $R_2$ and $R_3$ is independently hydrogen, alkyl, aryl, heteroaryl or cycloalkyl.

In one embodiment, an example of the compound represented by Formula 7 may be a compound represented by Formulas 7-1 to 7-6, but it is not limited thereto.

[Formula 7-1]

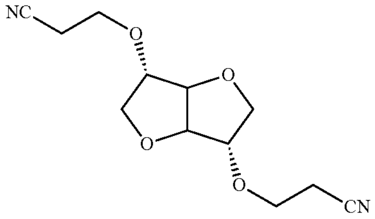

[Formula 7-2]

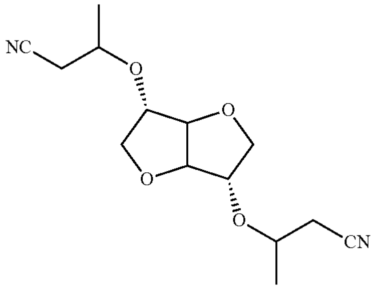

[Formula 7-3]

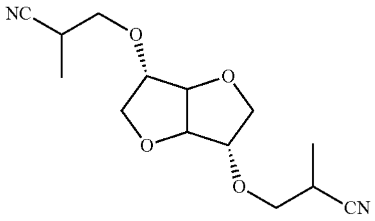

-continued

[Formula 7-4]

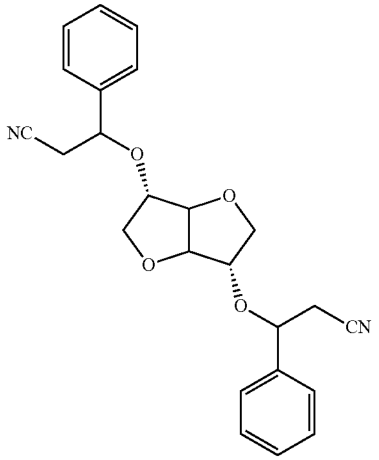

[Formula 7-5]

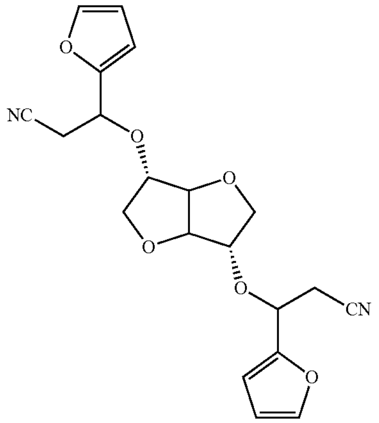

[Formula 7-6]

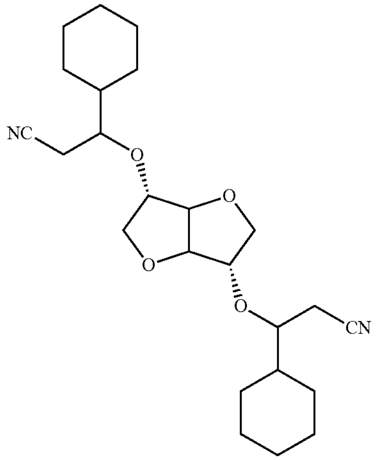

In one embodiment, when min is an integer of 1 to 25, that is, when the compound represented by Formula A' of the present invention is a dinitrile compound having an anhydrosugar alcohol core and an alkylene oxide extension, the compound represented by Formula A' may be a compound represented by the following Formula 10 (isosorbide-alkylene glycol-dinitrile compound):

[Formula 10]

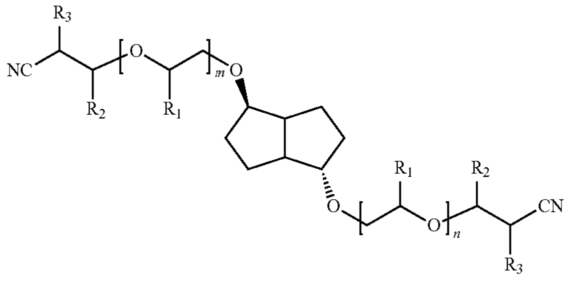

in Formula 10, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and min is an integer from 1 to 25.

In one embodiment, an example of the compound represented by Formula 10 may be a compound represented by Formulas 10-1 to 10-6, but it is not limited thereto.

[Formula 10-1]

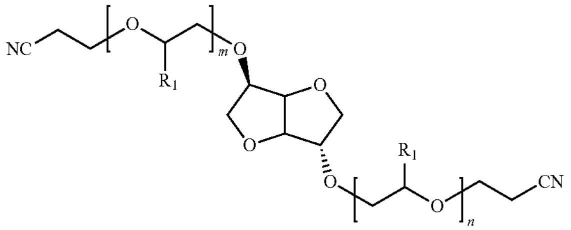

[Formula 10-2]

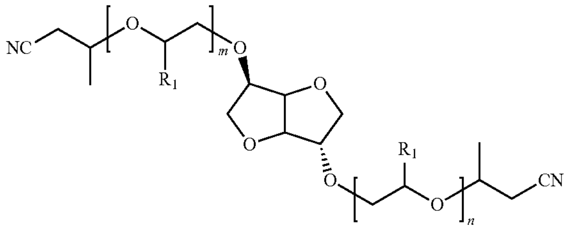

[Formula 10-3]

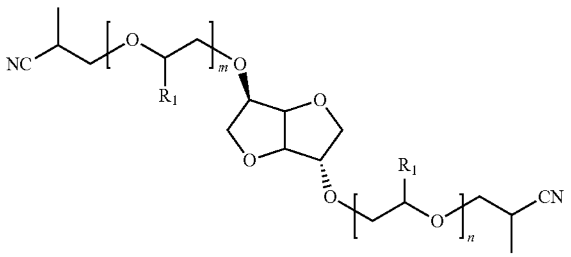

[Formula 10-4]

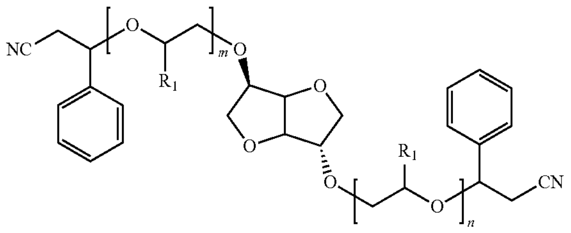

-continued

[Formula 10-5]

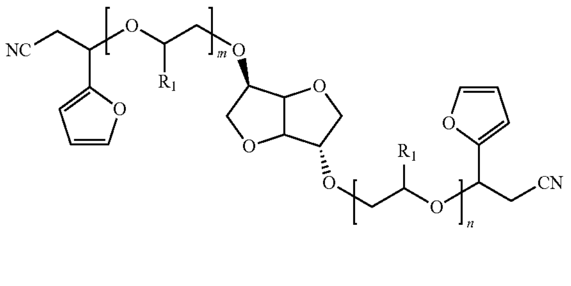

[Formula 10-6]

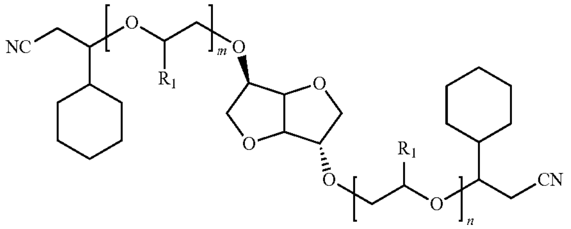

in Formulas 10-1 to 10-6, each $R_1$ is independently hydrogen, alkyl or aryl, each of m and n is independently an integer of 0 to 15, and m+n is an integer from 1 to 25.

In one embodiment, when m+n is an integer of 1 to 25, that is, when the compound represented by Formula A' of the present invention is a dinitrile compound having an anhydrosugar alcohol core and an alkylene oxide extension, the compound represented by Formula A' may be a compound represented by the following Formula 13 (isomannide-alkylene glycol-dinitrile compound):

[Formula 13]

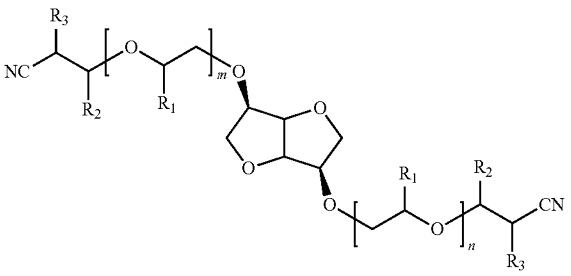

in Formula 13, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and min is an integer from 1 to 25.

In one embodiment, an example of the compound represented by Formula 13 may be a compound represented by Formulas 13-1 to 13-6, but it is not limited thereto.

[Formula 13-1]

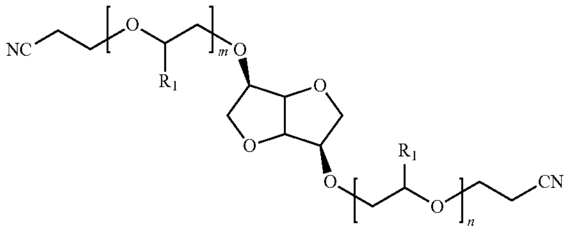

[Formula 13-2]

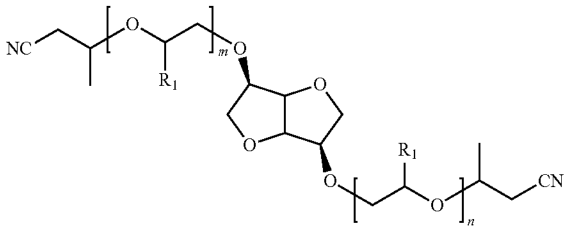

[Formula 13-3]

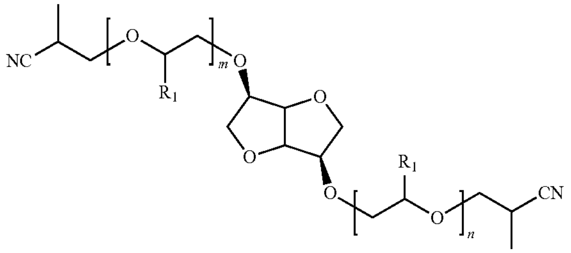

[Formula 13-4]

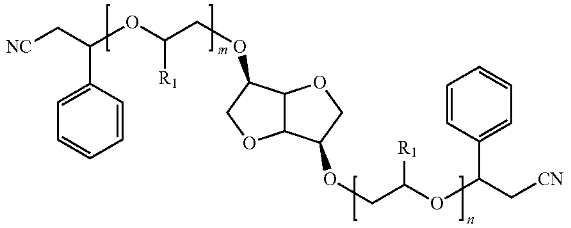

[Formula 13-5]

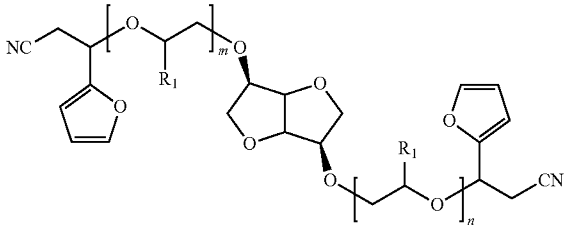

[Formula 13-6]

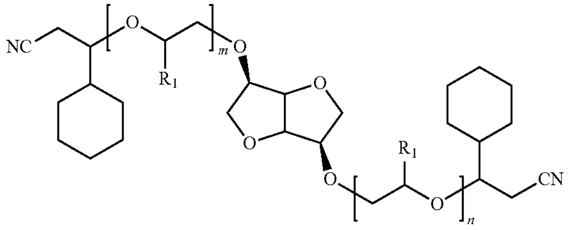

in Formulas 13-1 to 13-6, each $R_1$ is independently hydrogen, alkyl or aryl, each of m and n is independently an integer of 0 to 15, and m+n is an integer from 1 to 25.

In one embodiment, when m+n is an integer of 1 to 25, that is, when the compound represented by Formula A' of the present invention is a dinitrile compound having an anhydrosugar alcohol core and an alkylene oxide extension, the compound represented by Formula A' may be a compound represented by the following Formula 16 (isoidide-alkylene glycol-dinitrile compound):

[Formula 16]

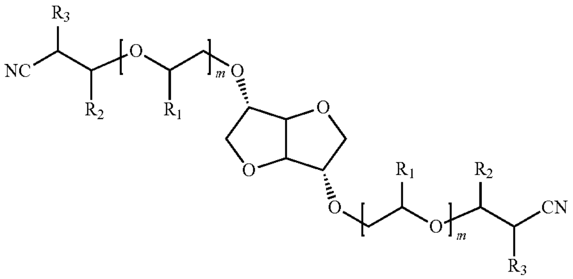

in Formula 16, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

In one embodiment, an example of the compound represented by Formula 16 may be a compound represented by Formulas 16-1 to 16-6, but it is not limited thereto.

[Formula 16-1]

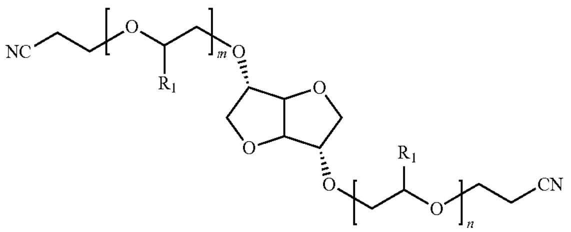

[Formula 16-2]

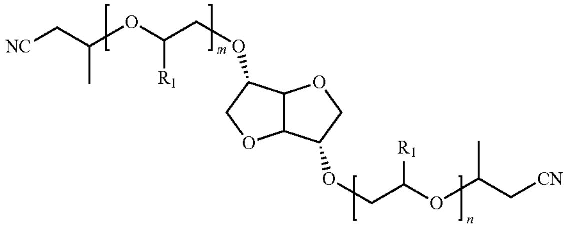

[Formula 16-3]

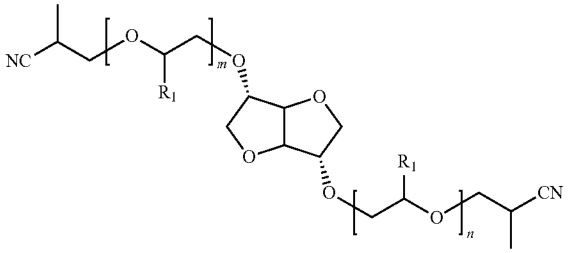

-continued

[Formula 16-4]

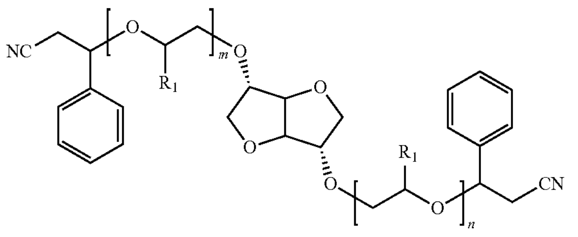

[Formula 16-5]

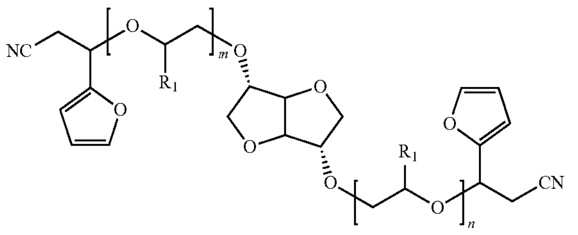

[Formula 16-6]

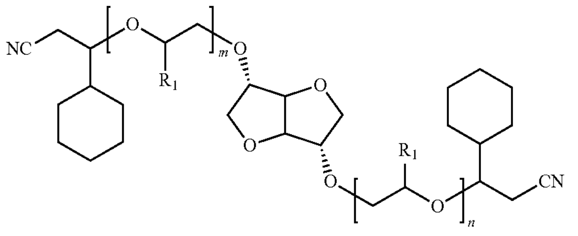

in Formulas 16-1 to 16-6.

each $R_1$ is independently hydrogen, alkyl or aryl, each of m and n is independently an integer of 0 to 15, and m+n is an integer from 1 to 25.

In the preparation method of the present invention, step (2) of adding hydrogen to the compound obtained from the Michael reaction may advantageously be performed in the presence of ammonia and may be performed under the following conditions.

Step (2) can be performed under a temperature condition of 40° C. to 180° C., preferably 50° C. to 130° C. and a hydrogen pressure condition of 5 to 30 bar, and in the presence of 0.1 to 20 parts by weight, preferably 0.5 to 10 parts by weight of a hydrogenation catalyst based on 100 parts by weight of the compound represented by Formula A'.

If the hydrogen pressure is too low, hydrogen is not sufficiently added, so that the yield of the hydrogenation reaction product may be lowered. On the other hand, if the hydrogen pressure is too high, it is difficult to expect additional effects.

Step (2) may be performed without using a solvent or may be performed in a solvent. If step (2) is performed in a solvent, the solvent may be selected from water or a linear or branched $C_1$-$C_5$ alcohol.

In the preparation method of the present invention, the compound obtained from the hydrogenation reaction in step (2) may be a compound represented by the following Formula A":

X"—Y—O—M—O—Y'—X" [Formula A"]

in Formula A", each X" is independently $-CH_2NH_2$,

Y is $-[CH_2CHR_1O]_m-CHR_2CHR_3-$, wherein each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and M is a divalent organic group derived from anhydrosugar alcohol.

In Formula A", the alkyl may be, for example, a substituted or unsubstituted linear alkyl having 1 to 10 carbon atoms (more specifically 1 to 6); or a substituted or unsubstituted branched alkyl having 3 to 10 carbon atoms (more specifically 3 to 6). The aryl may be, for example, a substituted or unsubstituted monocyclic aryl, polycyclic aryl or fused cyclic aryl having carbon number 6 to 14 (more specifically 6 to 12). In addition, the heteroaryl may be, for example, a substituted or unsubstituted 5- to 12-membered (more specifically 5- to 10-membered) monocyclic heteroaryl, polycyclic heteroaryl or fused cyclic heteroaryl comprising at least one heteroatom selected from N, O or S. The cycloalkyl may be, for example, a substituted or unsubstituted cycloalkyl having 3 to 8 carbon atoms (more specifically 3 to 6).

The groups can be substituted with, for example, one or more substituents selected from $C_1$-$C_{10}$ alkyl (e.g., methyl, ethyl, propyl, butyl, etc.) or $C_6$-$C_{10}$ aryl (e.g., phenyl, benzyl, tolyl, etc.).

In Formula A", each of m and n is independently an integer of 0 to 15, so when both m and n are 0, a renewable plant-based anhydrosugar alcohol is used as a raw material, and the compound represented by Formula A" means a compound that does not comprise an alkylene oxide extension between an anhydrosugar alcohol core and an amine group (referred to herein as a "diamine compound having an anhydrosugar alcohol core"). In addition, when m+n is an integer of 1 to 25, a renewable plant-based anhydrosugar alcohol-alkylene glycol is used as a raw material, and the compound represented by Formula A" means a compound comprising an alkylene oxide extension between the anhydrosugar alcohol core and an amine group (referred to herein as a "diamine compound having an anhydrosugar alcohol core and an alkylene oxide extension").

In one embodiment, when both m and n are 0, that is, when the compound represented by Formula A" of the present invention is a diamine compound having an anhydrosugar alcohol core, the compound represented by Formula A" may be a compound represented by the following Formula 2 (isosorbide diamine compound):

[Formula 2]

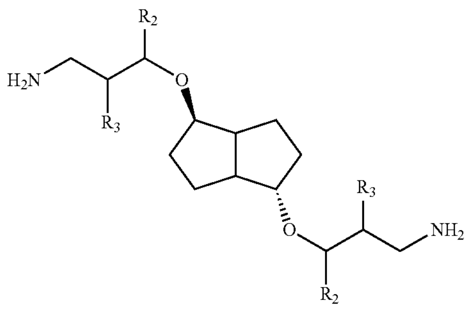

in Formula 2, each of $R_2$ and $R_3$ is independently hydrogen, alkyl, aryl, heteroaryl or cycloalkyl.

In one embodiment, an example of the compound represented by Formula 2 may be a compound represented by Formulas 2-1 to 2-6, but it is not limited thereto.

[Formula 2-1]

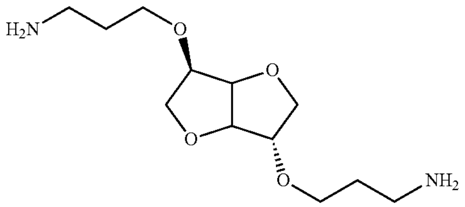

[Formula 2-2]

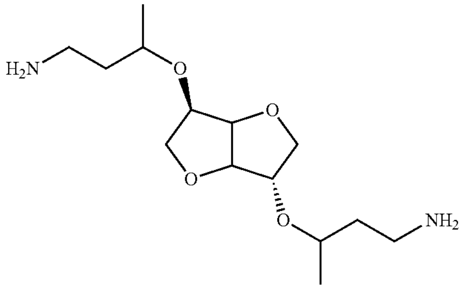

[Formula 2-3]

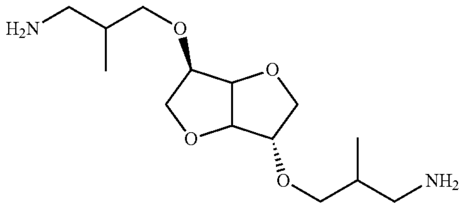

[Formula 2-4]

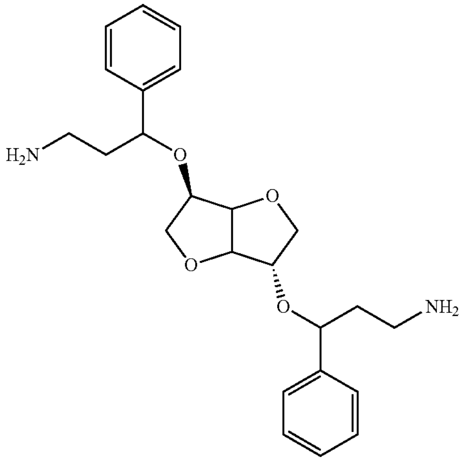

-continued

[Formula 2-5]

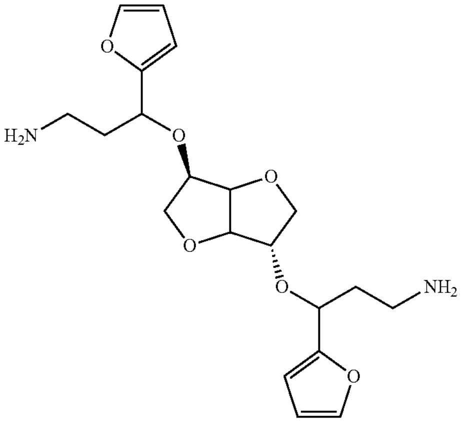

[Formula 2-6]

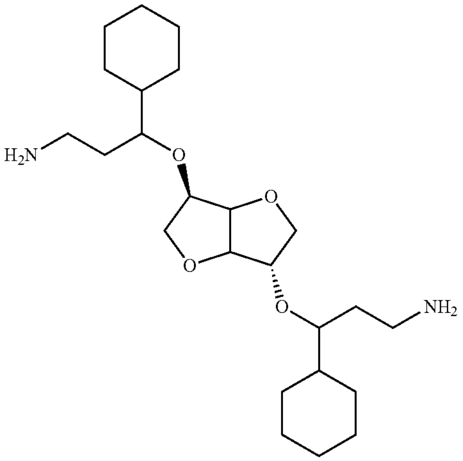

In one embodiment, when both m and n are 0, that is, when the compound represented by Formula A" of the present invention is a diamine compound having an anhydrosugar alcohol core, the compound represented by Formula A" may be a compound represented by the following Formula 5 (isomannide diamine compound):

[Formula 5]

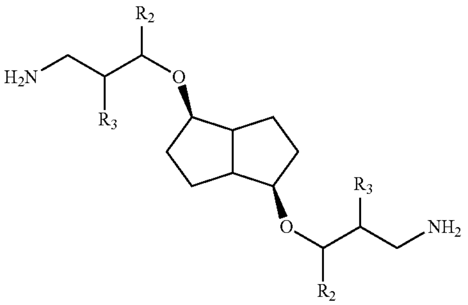

in Formula 5, each of $R_2$ and $R_3$ is independently hydrogen, alkyl, aryl, heteroaryl or cycloalkyl.

In one embodiment, an example of the compound represented by Formula 5 may be a compound represented by Formulas 5-1 to 5-6, but it is not limited thereto.

[Formula 5-1]

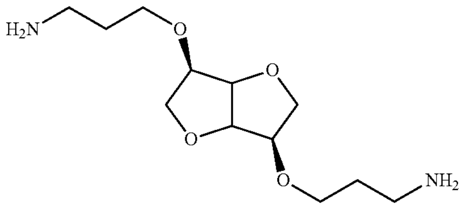

[Formula 5-2]

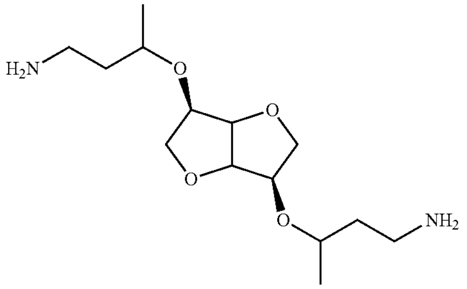

[Formula 5-3]

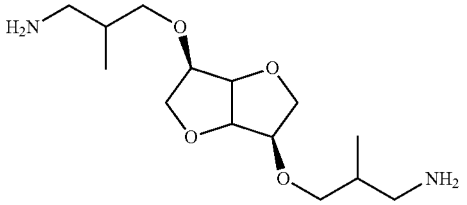

[Formula 5-4]

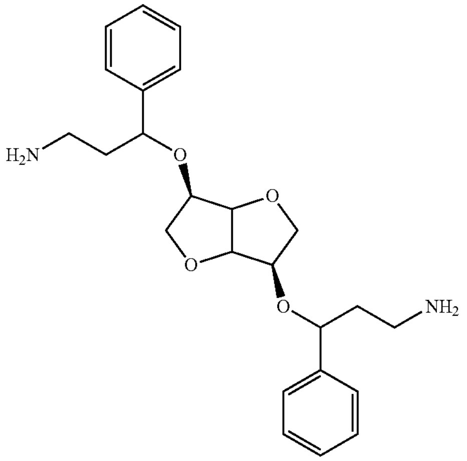

-continued

[Formula 5-5]

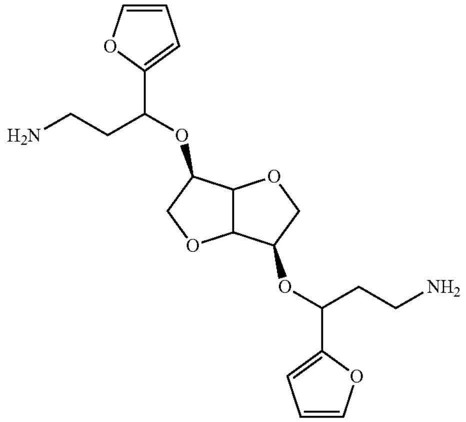

[Formula 5-6]

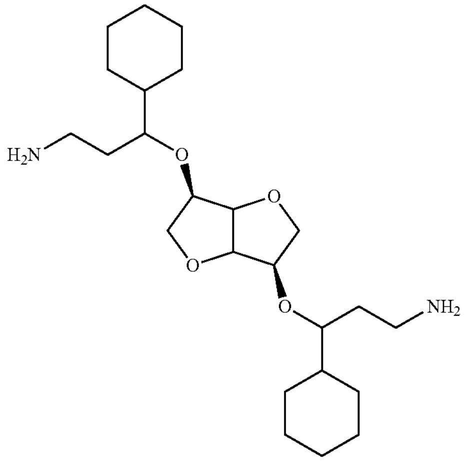

In one embodiment, when both m and n are 0, that is, when the compound represented by Formula A" of the present invention is a diamine compound having an anhydrosugar alcohol core, the compound represented by Formula A" may be a compound represented by the following Formula 8 (isoidide diamine compound):

[Formula 8]

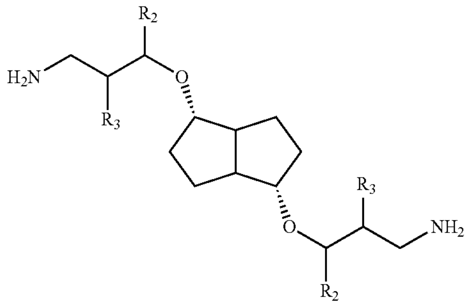

in Formula 8, each of $R_2$ and $R_3$ is independently hydrogen, alkyl, aryl, heteroaryl or cycloalkyl.

In one embodiment, an example of the compound represented by Formula 8 may be a compound represented by Formulas 8-1 to 8-6, but it is not limited thereto.

[Formula 8-1]

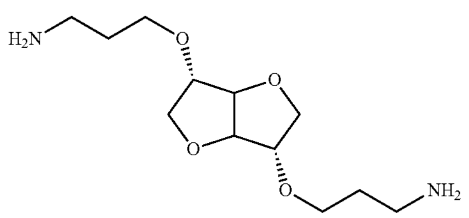

[Formula 8-2]

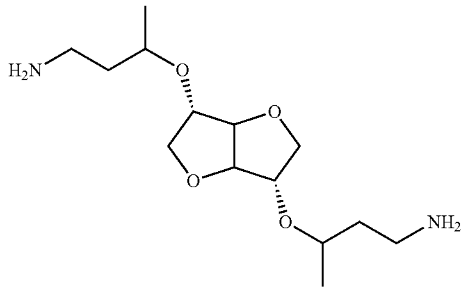

[Formula 8-3]

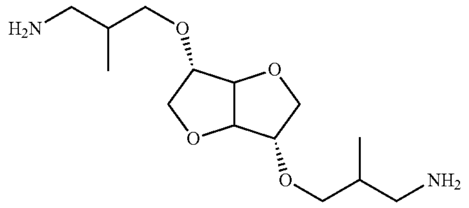

[Formula 8-4]

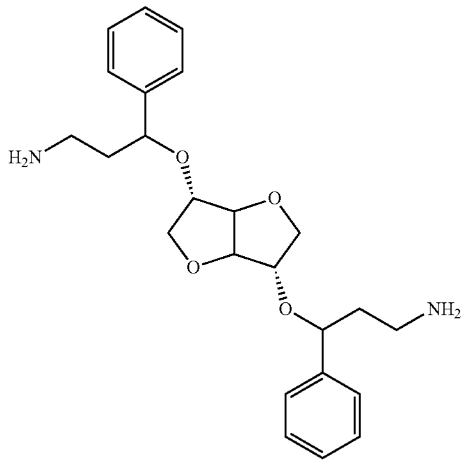

-continued

[Formula 8-5]

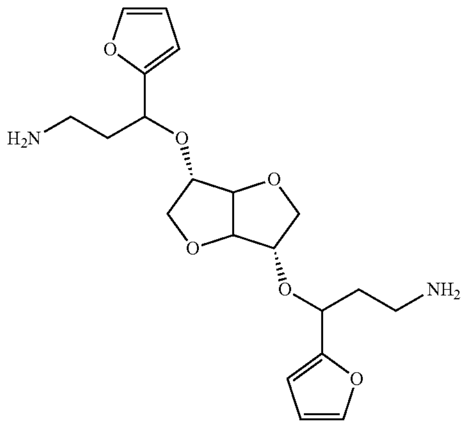

[Formula 8-6]

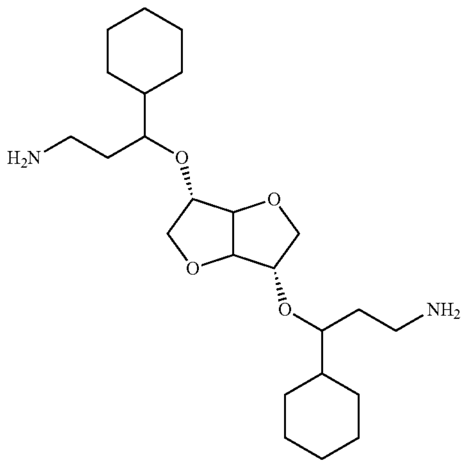

In one embodiment, when min is an integer of 1 to 25, that is, when the compound represented by Formula A" of the present invention is a diamine compound having an anhydrosugar alcohol core and an alkylene oxide extension, the compound represented by Formula A" may be a compound represented by the following Formula 11 (isosorbide-alkylene glycol-diamine compound):

[Formula 11]

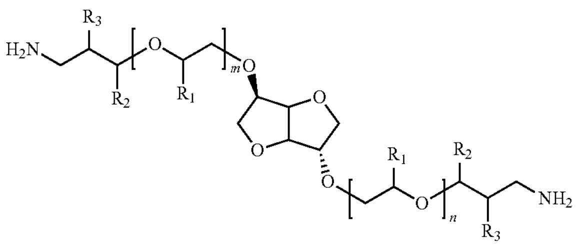

in Formula 11, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

In one embodiment, an example of the compound represented by Formula 11 may be a compound represented by Formulas 11-1 to 11-6, but it is not limited thereto.

[Formula 11-1]

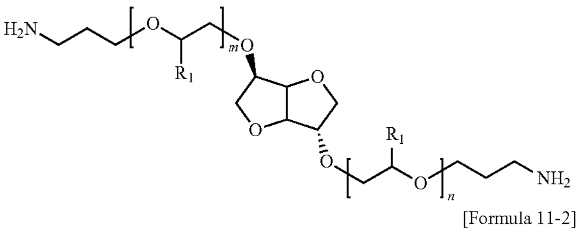

[Formula 11-2]

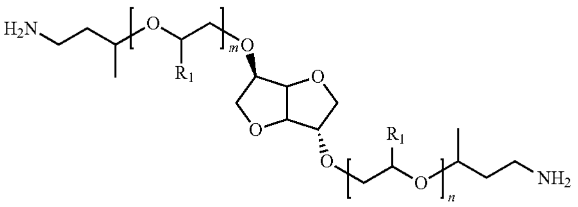

[Formula 11-3]

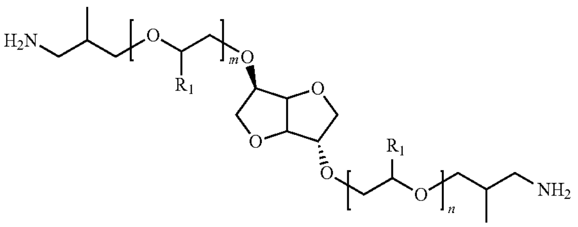

[Formula 11-4]

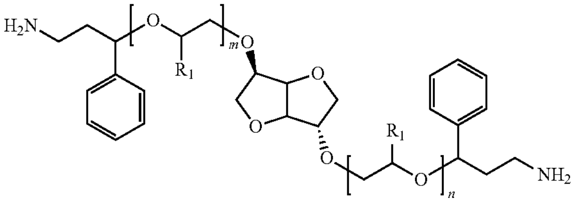

[Formula 11-5]

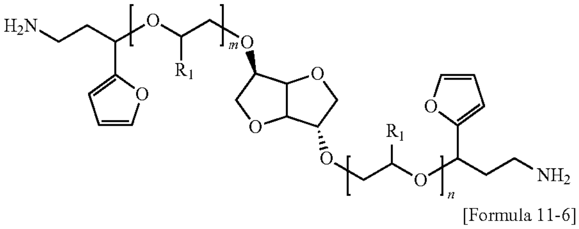

[Formula 11-6]

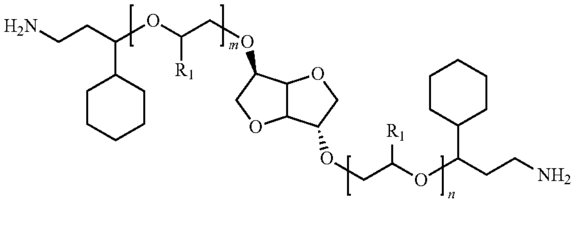

in Formulas 11-1 to 11-6, each $R_1$ is independently hydrogen, alkyl or aryl, each of m and n is independently an integer of 0 to 15, and m+n is an integer from 1 to 25.

In one embodiment, when m+n is an integer of 1 to 25, that is, when the compound represented by Formula A" of the present invention is a diamine compound having an anhydrosugar alcohol core and an alkylene oxide extension, the compound represented by Formula A" may be a compound represented by the following Formula 14 (isomannide-alkylene glycol-diamine compound):

[Formula 14]

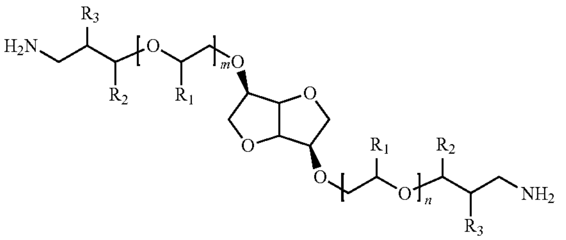

in Formula 14, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

In one embodiment, an example of the compound represented by Formula 14 may be a compound represented by Formulas 14-1 to 14-6, but it is not limited thereto.

[Formula 14-1]

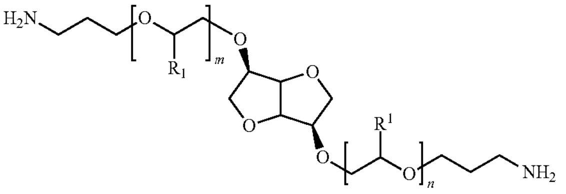

[Formula 14-2]

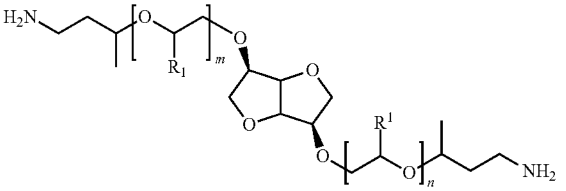

[Formula 14-3]

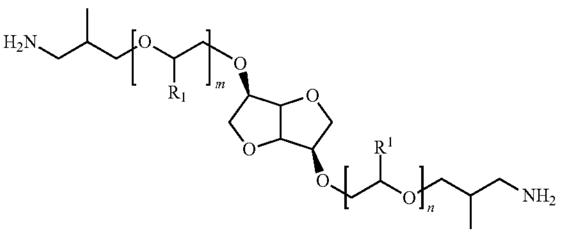

-continued

[Formula 14-4]

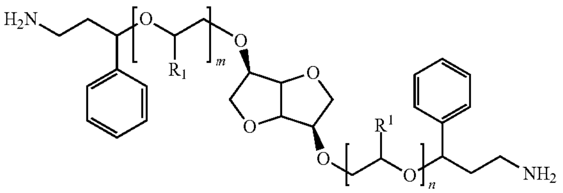

[Formula 14-5]

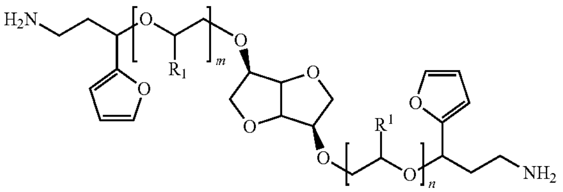

[Formula 14-6]

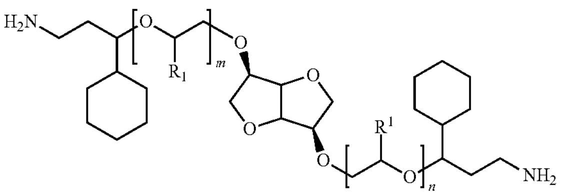

in Formulas 14-1 to 14-6.

each $R_1$ is independently hydrogen, alkyl or aryl, each of m and n is independently an integer of 0 to 15, and m+n is an integer from 1 to 25.

In one embodiment, when m+n is an integer of 1 to 25, that is, when the compound represented by Formula A" of the present invention is a diamine compound having an anhydrosugar alcohol core and an alkylene oxide extension, the compound represented by Formula A" may be a compound represented by the following Formula 17 (isoidide-alkylene glycol-diamine compound):

[Formula 17]

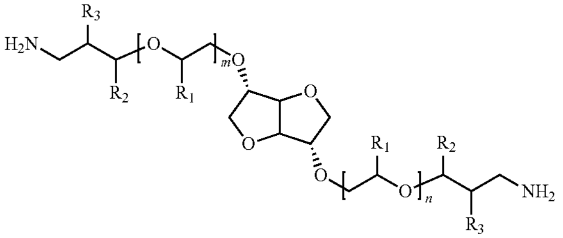

in Formula 17, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

In one embodiment, an example of the compound represented by Formula 17 may be a compound represented by Formulas 17-1 to 17-6, but it is not limited thereto.

[Formula 17-1]

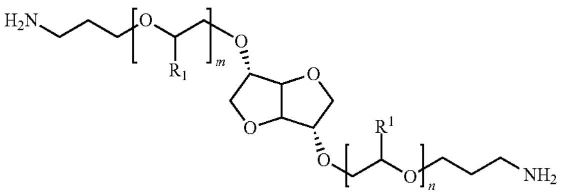

[Formula 17-2]

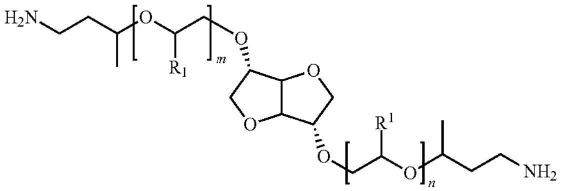

[Formula 17-3]

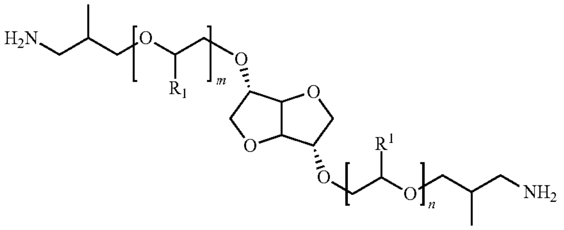

[Formula 17-4]

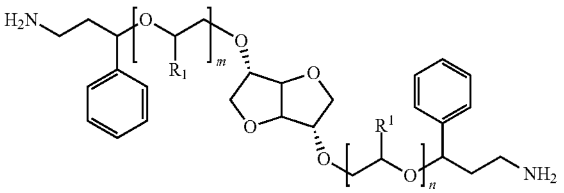

[Formula 17-5]

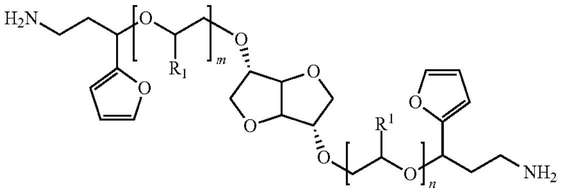

[Formula 17-6]

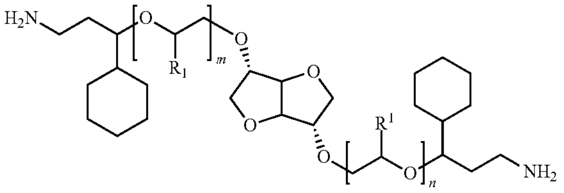

in Formulas 17-1 to 17-6, each $R_1$ is independently hydrogen, alkyl or aryl, each of m and n is independently an integer of 0 to 15, and m+n is an integer from 1 to 25.

In the preparation method of the present invention, step (3) of converting the terminal group of the compound obtained from the hydrogenation into an isocyanate can be performed by reacting the diamine compound obtained from the hydrogenation with a carbonate-based compound, a phosgene-based compound; carbon monoxide and oxygen; or carbon dioxide.

The carbonate-based compound that can be used in step (3) may be di-tert-butyl dicarbonate, dimethyl dicarbonate, diethyl dicarbonate, dibenzyl dicarbonate, dimethyl carbonate, diethyl carbonate, diphenyl carbonate, ethylmethyl carbonate or a combination thereof, but it is not limited thereto.

In step (3), when the compound obtained from the hydrogenation is reacted with a carbonate-based compound, the reaction can be performed under a temperature condition of −20° C. to 100° C., preferably 10° C. to 80° C., and the content of the carbonate-based compound may be 2 to 10 molar equivalents, preferably 2 to 5 molar equivalents, based on 1 molar equivalent of the compound obtained from the hydrogenation.

As the phosgene-based compound that can be used in step (3), one selected from phosgene, diphosgene, triphosgene or a combination thereof may be used, but it is not limited thereto.

In step (3), when the compound obtained from the hydrogenation is reacted with a phosgene-based compound, the reaction can be performed under a temperature condition of −60° C. to 200° C., preferably 0° C. to 150° C., and the content of the phosgene-based compound may be 2 to 10 molar equivalents, preferably 2 to 5 molar equivalents, based on 1 molar equivalent of the compound obtained from the hydrogenation.

The reaction of step (3) can be performed in the presence of a catalyst, and 4-dimethylaminopyridine, zinc acetate, sodium methoxide, trialkylamine (e.g., triethylamine, etc.), Group III metal halide (e.g., $AlCl_3$, etc.) or a combination thereof may be used as the catalyst, but it is not limited thereto.

When the catalyst is used in step (3), the content of the catalyst may be 0.01 to 3 molar equivalents, preferably 0.03 to 1 molar equivalent, based on 1 molar equivalent of the compound obtained from the hydrogenation.

The compound represented by Formula A according to the present invention can be used in various applications requiring an isocyanate, and the compound represented by Formula A may be used alone or mixed with a polyisocyanate of divalent or higher other than the compound represented by Formula A.

The compound represented by Formula A according to the present invention can be used in various fields such as thermoplastic polyurethane (TPU), soft or rigid polyurethane foam, soft or rigid polyurethane molded foam, coating, tackifier, adhesive, fiber and polymer synthesis.

Therefore, in still another aspect, the present invention provides a polymer comprising the above compound represented by Formula A.

Since the compound represented by Formula A according to the present invention has a high contents of raw materials derived biomass, the eco-friendliness of a polymer prepared using it can be remarkably improved.

The polymer according to the present invention may be, for example, thermoplastic polyurethane (TPU), soft or rigid polyurethane foam, polyurea, polyamide, polyimide, binder resin, thermoplastic polyester elastomer, artificial leather polyurethane or emulsion polymer, but it is not limited thereto.

In addition, the compound represented by Formula A according to the present invention may be used in a powder coating composition, a tackifier composition or an adhesive composition, etc.

Although not particularly limited, the lower limit of the content of the compound represented by Formula A comprised in the polymer according to the present invention may be, based on 100 parts by weight of the polyol, 20 parts by weight or more, 25 parts by weight or more, 30 parts by weight or more, 35 parts by weight or more, 40 parts by weight or more, 45 parts by weight or more, 50 parts by weight or more, 55 parts by weight or more or 60 parts by weight or more, and the upper limit may be 80 parts by weight or less, 75 parts by weight or less, 70 parts by weight or less, 65 parts by weight or less, 60 parts by weight or less, 55 parts by weight or less, 50 parts by weight or less, 45 parts by weight or less, 40 parts by weight or less, 35 parts by weight or less or 30 parts by weight or less. For example, the content of the compound represented by Formula A may be 20 to 80 parts by weight, 20 to 70 parts by weight, 25 to 60 parts by weight, 30 to 60 parts by weight, 34 to 55 parts by weight or 34 to 53 parts by weight based on 100 parts by weight of polyol. If the content of the compound represented by Formula A is too small, the tensile strength and elongation of the polymer may be poor. On the other hand, if the content is too high, it is difficult to expect additional effects.

In one embodiment, the content of the compound represented by Formula A comprised in the polymer according to the present invention is preferably an amount of 70 to 130, particularly preferably 80 to 120, still preferably 100 to 120 in terms of an isocyanate index. The isocyanate index is the ratio of the number of equivalents of hydroxy groups present in the polyol and the number of equivalents of isocyanate in the urethane reactant and means the ratio of the amount of isocyanate used relative to the theoretical equivalent. If the isocyanate index is less than 100, it means that an excess of polyol is present. If the isocyanate index is more than 100, it means that there is an excess of isocyanate. If the isocyanate index is less than 70, there is a problem in that the reactivity is poor, the gelling reaction is delayed and hardening is not possible. If the isocyanate index exceeds 130, the hard segment is excessively increased, causing shrinkage.

The present invention is explained in more detail through the following Examples and Comparative Examples. However, the scope of the present invention is not limited thereby in any manner.

In the following, the dianhydrohexitol-dinitrile compound and the dianhydrohexitol-diamine compound were used as intermediate compounds for preparing the dianhydrohexitol-diisocyanate compound, and the dianhydrohexitol-alkylene glycol, the dianhydrohexitol-alkylene glycol-dinitrile compound and the dianhydrohexitol-alkylene glycol-diamine compound were used as intermediate compounds for preparing the dianhydrohexitol-alkylene glycol-diisocyanate compound.

EXAMPLES

I. Preparation of Diisocyanate Compound Having Anhydrosugar Alcohol Core (when m and n are Both 0 in Formula A)

<Preparation of Dianhydrohexitol Dinitrile Compound (Compound of Formula A')>

Example I-A1: Preparation of Isosorbide Diacrylonitrile 1,000 g (6.8 mol, 1.0 equivalent) of isosorbide and 10 g (0.068 mol, 0.01 equivalent) of 1,8-diazabicyclo[5.4.0]undec-7-ene were added to a glass reactor and the internal temperature was adjusted to 70 to 75° C. After completely dissolving the isosorbide, 916 g (17 mol, 2.5 equivalents) of acrylonitrile was slowly added dropwise for about 4 hours so that the internal temperature did not exceed 80° C. After completion of the dropwise addition, the mixture was stirred for 3 hours while adjusting the internal temperature to 70 to 75° C., and then cooled to room temperature. The reaction mixture was diluted with 4 kg of ethyl acetate and then washed sequentially with 2 kg of 1-normal aqueous hydrochloric acid solution, 2 kg of 1-normal sodium hydroxide aqueous solution and 2 kg of distilled water, and then concentrated under reduced pressure to obtain 1,536 g of isosorbide diacrylonitrile, a compound of Formula 1-1. At this time, the yield was 89%.

[Formula 1-1]

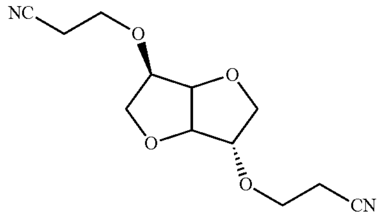

$^1$H NMR (δ ppm; DMSO-$d_6$): 2.58 (2H, d), 2.62 (2H, d), 3.48-3.51 (2H, m), 3.73-3.78 (6H, m), 3.93-3.97 (2H, m), 4.01-4.06 (2H, m)

MS(m/e): 252

Example I-A2: Preparation of Isosorbide Dicrotononitrile

Except that 1,140 g (17 mol, 2.5 equivalents) of crotononitrile was used instead of 916 g (17 mol, 2.5 equivalents) of acrylonitrile, 1,750 g of isosorbide dicrotononitrile, a compound of Formula 1-2 was obtained in the same manner as in Example I-A1. At this time, the yield was 92%.

[Formula 1-2]

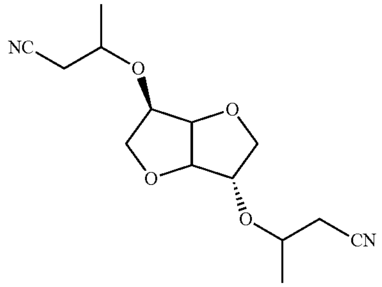

$^1$H NMR (δ ppm; DMSO-$d_6$): 1.18 (3H, d), 1.21 (3H, d), 2.35 (1H, dd), 2.39 (1H, dd), 2.66 (1H, dd), 2.70 (1H, dd), 3.00 (1H, m), 3.12 (1H, m), 3.49 (1H, m), 3.62 (1H, m), 3.67 (1H, dd), 3.77 (1H, dd), 3.94 (1H, d), 4.01 (1H, d), 4.09 (1H, dd), 4.17 (1H, dd)

MS(m/e): 280

Example I-A3: Preparation of Isosorbide Dimethacrylonitrile

Except that 1,140 g (17 mol, 2.5 equivalents) of methacrylonitrile was used instead of 916 g (17 mol, 2.5 equivalents) of acrylonitrile. 1,710 g of isosorbide dimethacrylonitrile, a compound of Formula 1-3 was obtained in the same manner as in Example I-A1. At this time, the yield was 91%.

[Formula 1-3]

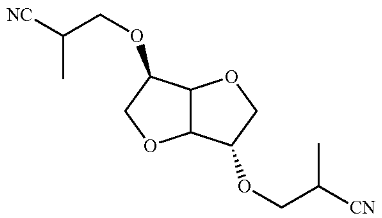

$^1$H NMR (δ ppm; DMSO-$d_6$): 1.41 (3H, d), 1.43 (3H, d), 2.99 (1H, m), 3.04 (1H, m), 3.49-3.64 (6H, m), 3.83 (1H, dd), 3.91 (1H, dd), 3.90 (1H, d), 3.99 (1H, d), 4.02 (1H, dd), 4.08 (1H, dd)

MS(m/e): 280

Example I-A4: Preparation of Isosorbide Dicinnamonitrile

Except that 2,196 g (17 mol, 2.5 equivalents) of cinnamonitrile was used instead of 916 g (17 mol, 2.5 equivalents) of acrylonitrile, and the stirring time after completion of the dropwise addition was changed from 3 hours to 6 hours, 2,500 g of isosorbide dicinnamonitrile, a compound of Formula 1-4, was obtained in the same manner as in Example I-A1. At this time, the yield was 91%.

[Formula 1-4]

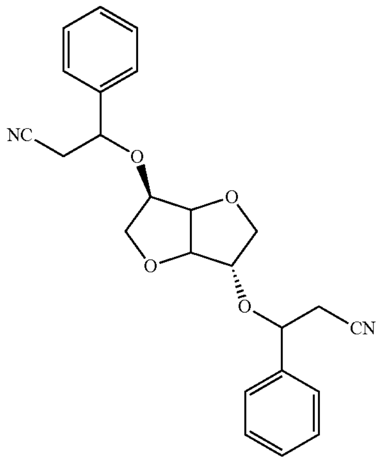

$^1$H NMR (δ ppm; DMSO-$d_6$): 2.74 (1H, dd), 2.80 (1H, dd), 2.99 (1H, dd), 3.07 (1H, dd), 3.48 (1H, m), 3.53 (1H, m), 3.76 (1H, dd), 3.80 (1H, dd), 3.93 (1H, d), 3.98 (1H, d), 4.04 (1H, dd), 4.10 (1H, dd), 4.25 (1H, t), 4.29 (1H, t), 7.18-7.40 (10H, m)

MS(m/e): 404

Example I-A5: Preparation of Isosorbide Di(3-Furyl)Acrylonitrile

Except that 2,025 g (17 moles, 2.5 equivalents) of 3-(furan-2-yl)prop-2-enenitrile was used instead of 916 g (17 moles, 2.5 equivalents) of acrylonitrile, and the stirring time after completion of the dropwise addition was changed from 3 hours to 9 hours, 2,450 g of isosorbide di(3-furyl) acrylonitrile, a compound of Formula 1-5 was obtained in the same manner as in Example I-A1. At this time, the yield was 90%.

[Formula 1-5]

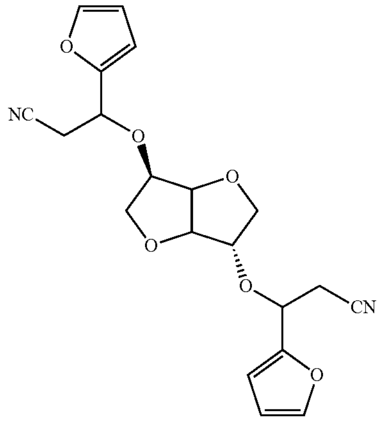

$^1H$ NMR (δ ppm; DMSO-$d_6$): 2.79 (1H, dd), 2.88 (1H, dd), 3.04 (1H, dd), 3.12 (1H, dd), 3.50 (1H, m), 3.55 (1H, m), 3.81 (1H, dd), 3.88 (1H, dd), 4.05 (1H, dd), 4.10 (1H, dd), 4.41 (1H, t), 4.45 (1H, t), 6.19-6.28 (4H, m), 7.30-7.35 (2H, m) MS(m/e): 384

Example I-A6: Preparation of Isosorbide Di(3-Cyclohexyl)Acrylonitrile

Except that 2,299 g (17 moles, 2.5 equivalents) of cyclohexane acrylonitrile was used instead of 916 g (17 moles, 2.5 equivalents) of acrylonitrile, and the stirring time after completion of the dropwise addition was changed from 3 hours to 5 hours, 2,785 g of isosorbide di(3-cyclohexyl) acrylonitrile, a compound of Formula 1-6 was obtained in the same manner as in Example I-A1. At this time, the yield was 88%.

[Formula 1-6]

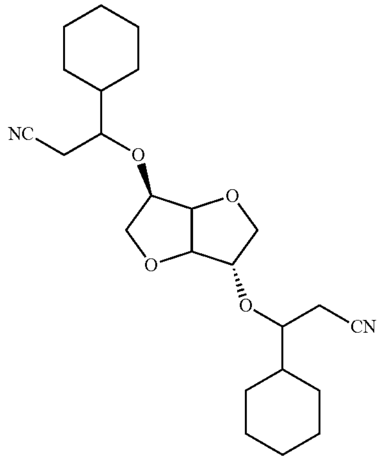

$^1H$ NMR (δ ppm; DMSO-$d_6$): 1.27-1.77 (22H, m), 2.49 (1H, dd), 2.53 (1H, dd), 2.70 (1H, dd), 2.74 (1H, dd), 2.88 (1H, m), 3.53 (1H, m), 3.55 (1H, dd), 3.59 (1H, dd), 3.62 (1H, d), 3.70 (1H, d), 3.80 (1H, dd), 3.88 (1H, dd), 4.05 (1H, t), 4.09 (1H, t) MS(m/e): 416

Example I-B1: Preparation of Isomannide Diacrylonitrile

Except that 1,000 g (6.8 mol, 1.0 equivalent) of isomannide was used instead of 1,000 g (6.8 mol, 1.0 equivalent) of isosorbide, the melting and reaction temperature was changed to 80° C. to 85° C., and the stirring time after completion of the dropwise addition was changed from 3 hours to 6 hours, 1,467 g of isomannide diacrylonitrile, a compound of Formula 4-1 was obtained in the same manner as in Example I-A1. At this time, the yield was 85%.

[Formula 4-1]

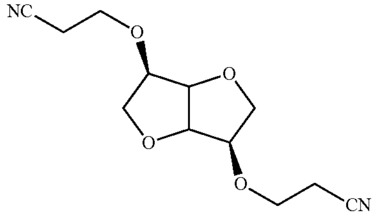

$^1H$ NMR (δ ppm; DMSO-$d_6$): 2.43 (2H, d), 2.50 (2H, d), 3.48-3.55 (2H, m), 3.69-3.81 (6H, m), 3.87-3.94 (2H, m), 4.05-4.10 (2H, m)

MS(m/e): 252

Example I-B2: Preparation of Isomannide Dicrotononitrile

Except that 1,000 g (6.8 mol, 1.0 equivalent) of isomannide was used instead of 1,000 g (6.8 mol, 1.0 equivalent) of isosorbide, 1,140 g (17 mol, 2.5 equivalents) of crotononitrile was used instead of 916 g (17 mol, 2.5 equivalents) of acrylonitrile and the melting and reaction temperature was changed to 80° C. to 85° C., 1,707 g of isomannide dicrotononitrile, a compound of Formula 4-2 was obtained in the same manner as in Example I-A1. At this time, the yield was 89%.

[Formula 4-2]

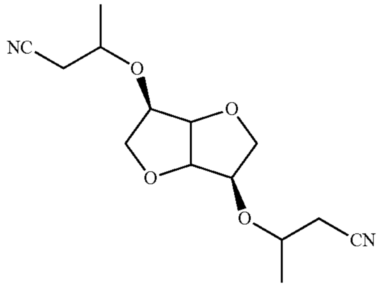

$^1H$ NMR (δ ppm; DMSO-$d_6$): 1.14 (3H, d), 1.20 (3H, d), 2.32 (1H, dd), 2.35 (1H, dd), 2.69 (1H, dd), 2.75 (1H, dd), 3.03 (1H, m), 3.10 (1H, m), 3.44 (1H, m), 3.58 (1H, m), 3.63 (1H, dd), 3.77 (1H, dd), 3.89 (1H, d), 3.96 (1H, d), 4.10 (1H, dd), 4.15 (1H, dd)

MS(m/e): 280

Example I-B3: Preparation of Isomannide Dimethacrylonitrile

Except that 1,000 g (6.8 mol, 1.0 equivalent) of isomannide was used instead of 1,000 g (6.8 mol, 1.0 equivalent) of isosorbide, 1,140 g (17 mol, 2.5 equivalents) of methacrylonitrile was used instead of 916 g (17 mol, 2.5 equivalents) of acrylonitrile and the melting and reaction temperature was changed to 80° C. to 85° C., 1,669 g of isomannide dimethacrylonitrile, a compound of Formula 4-3 was obtained in the same manner as in Example I-A1. At this time, the yield was 87%.

[Formula 4-3]

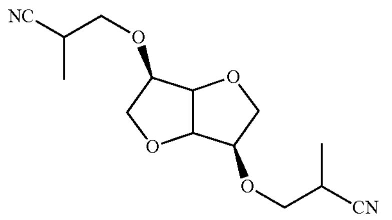

$^1$H NMR (δ ppm; DMSO-$d_6$): 1.44 (3H, d), 1.49 (3H, d), 3.04 (1H, m), 3.11 (1H, m), 3.45-3.66 (6H, m), 3.81 (1H, dd), 3.86 (1H, dd), 3.92 (1H, d), 3.99 (1H, d), 4.09 (1H, dd), 4.16 (1H, dd)

MS(m/e): 280

Example I-B4: Preparation of Isomannide Dicinnamonitrile

Except that 1,000 g (6.8 mol, 1.0 equivalent) of isomannide was used instead of 1,000 g (6.8 mol, 1.0 equivalent) of isosorbide, 2,196 g (17 mol, 2.5 equivalents) of cinnamonitrile was used instead of 916 g (17 mol, 2.5 equivalents) of acrylonitrile, the melting and reaction temperature was changed to 80° C. to 85° C. and the stirring time after completion of the dropwise addition was changed from 3 hours to 6 hours, 2,408 g of isomannide dicinnamonitrile, a compound of Formula 4-4 was obtained in the same manner as in Example I-A1. At this time, the yield was 87%.

[Formula 4-4]

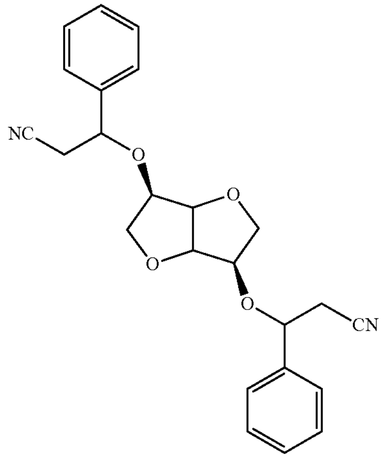

$^1$H NMR (δ ppm; DMSO-$d_6$): 2.59 (1H, dd), 2.64 (1H, dd), 2.92 (1H, dd), 3.00 (1H, dd), 3.41 (1H, m), 3.47 (1H, m), 3.66 (1H, dd), 3.78 (1H, dd), 3.90 (1H, d), 3.96 (1H, d), 4.04 (1H, dd), 4.10 (1H, dd), 4.20 (1H, t), 4.27 (1H, t), 7.15-7.36 (10H, m)

MS(m/e): 404

Example I-B5: Preparation of Isomannide Di(3-Furyl)Acrylonitrile

Except that 1,000 g (6.8 mol, 1.0 equivalent) of isomannide was used instead of 1,000 g (6.8 mol, 1.0 equivalent) of isosorbide, 2,025 g (17 moles, 2.5 equivalents) of 3-(furan-2-yl)prop-2-enenitrile was used instead of 916 g (17 moles, 2.5 equivalents) of acrylonitrile, the melting and reaction temperature was changed to 80° C. to 85° C. and the stirring time after completion of the dropwise addition was changed from 3 hours to 9 hours, 2,210 g of isomannide di(3-furyl) acrylonitrile, a compound of Formula 4-5 was obtained in the same manner as in Example I-A1. At this time, the yield was 84%.

[Formula 4-5]

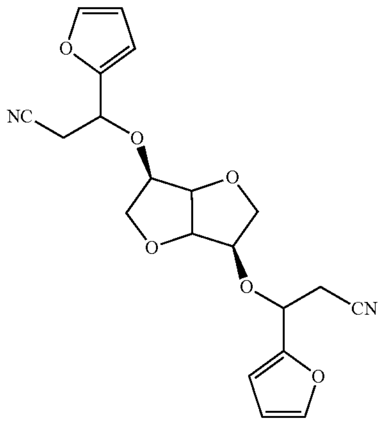

$^1$H NMR (δ ppm; DMSO-$d_6$): 2.67 (1H, dd), 2.74 (1H, dd), 3.00 (1H, dd), 3.08 (1H, dd), 3.43 (1H, m), 3.50 (1H, m), 3.75 (1H, dd), 3.87 (1H, dd), 3.99 (1H, dd), 4.07 (1H, dd), 4.40 (1H, t), 4.45 (1H, t), 6.11-6.23 (4H, m), 7.20-7.32 (2H, m) MS(m/e): 384

Example I-B6: Preparation of Isomannide Di(3-Cyclohexyl)Acrylonitrile

Except that 1,000 g (6.8 mol, 1.0 equivalent) of isomannide was used instead of 1,000 g (6.8 mol, 1.0 equivalent) of isosorbide, 2,299 g (17 moles, 2.5 equivalents) of cyclohexane acrylonitrile was used instead of 916 g (17 moles, 2.5 equivalents) of acrylonitrile, the melting and reaction temperature was changed to 80° C. to 85° C. and the stirring time after completion of the dropwise addition was changed from 3 hours to 5 hours, 2,423 g of isomannide di(3-cyclohexyl)acrylonitrile, a compound of Formula 4-6 was obtained in the same manner as in Example I-A1. At this time, the yield was 85%.

[Formula 4-6]

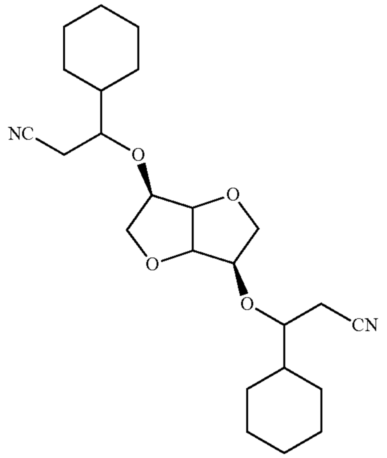

$^1$H NMR (δ ppm; DMSO-$d_6$): 1.20-1.64 (22H, m), 2.33 (1H, dd), 2.45 (1H, dd), 2.63 (1H, dd), 2.69 (1H, dd), 2.87 (1H, m), 3.46 (1H, m), 3.50 (1H, dd), 3.58 (1H, dd), 3.62 (1H, d), 3.67 (1H, d), 3.77 (1H, dd), 3.90 (1H, dd), 4.05 (1H, t), 4.11 (1H, t)

MS(m/e): 416

Example I-C1: Preparation of Isoidide Diacrylonitrile

Except that 1,000 g (6.8 mol, 1.0 equivalent) of isoidide was used instead of 1,000 g (6.8 mol, 1.0 equivalent) of isosorbide, the melting and reaction temperature was changed to 80° C. to 85° C. and the stirring time after completion of the dropwise addition was changed from 3 hours to 2 hours, 1,605 g of isoidide diacrylonitrile, a compound of Formula 7-1 was obtained in the same manner as in Example I-A1. At this time, the yield was 93%.

[Formula 7-1]

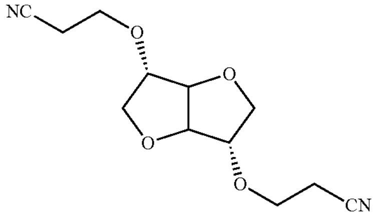

$^1$H NMR (δ ppm; DMSO-$d_6$): 2.58 (2H, d), 2.63 (2H, d), 3.47-3.52 (2H, m), 3.72-3.77 (6H, m), 3.88-3.95 (2H, m), 4.01-4.05 (2H, m)

MS(m/e): 252

Example I-C2: Preparation of Isoidide Dicrotononitrile

Except that 1,000 g (6.8 mol, 1.0 equivalent) of isoidide was used instead of 1,000 g (6.8 mol, 1.0 equivalent) of isosorbide, 1,140 g (17 mol, 2.5 equivalents) of crotononitrile was used instead of 916 g (17 mol, 2.5 equivalents) of acrylonitrile and the melting and reaction temperature was changed to 80° C. to 85° C., 1,707 g of isoidide dicrotononitrile, a compound of Formula 7-2 was obtained in the same manner as in Example I-A1. At this time, the yield was 93%.

[Formula 7-2]

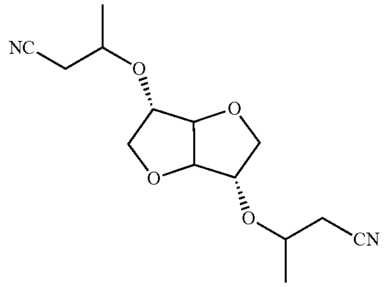

$^1$H NMR (δ ppm; DMSO-$d_6$): 1.21 (3H, d), 1.27 (3H, d), 2.39 (1H, dd), 2.44 (1H, dd), 2.70 (1H, dd), 2.76 (1H, dd), 3.03 (1H, m), 3.10 (1H, m), 3.56 (1H, m), 3.62 (1H, m), 3.701 (1H, dd), 3.77 (1H, dd), 3.99 (1H, d), 4.09 (1H, d), 4.16 (1H, dd), 4.27 (1H, dd) MS(m/e): 280

Example I-C3: Preparation of Isoidide Dimethacrylonitrile

Except that 1,000 g (6.8 mol, 1.0 equivalent) of isoidide was used instead of 1,000 g (6.8 mol, 1.0 equivalent) of isosorbide, 1,140 g (17 mol, 2.5 equivalents) of methacrylonitrile was used instead of 916 g (17 mol, 2.5 equivalents) of acrylonitrile and the melting and reaction temperature was changed to 80° C. to 85° C., 1,707 g of isoidide dimethacrylonitrile, a compound of Formula 7-3 was obtained in the same manner as in Example I-A1. At this time, the yield was 89%.

[Formula 7-3]

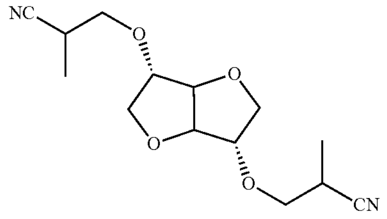

$^1$H NMR (δ ppm; DMSO-$d_6$): 1.45 (3H, d), 1.49 (3H, d), 2.99 (1H, m), 3.08 (1H, m), 3.52-3.68 (6H, m), 3.88 (1H, dd), 3.93 (1H, dd), 3.90 (1H, d), 4.00 (1H, d), 4.06 (1H, dd), 4.13 (1H, dd)

MS(m/e): 280

Example I-C4: Preparation of Isoidide Dicinnamonitrile

Except that 1,000 g (6.8 mol, 1.0 equivalent) of isoidide was used instead of 1,000 g (6.8 mol, 1.0 equivalent) of isosorbide, 2,196 g (17 mol, 2.5 equivalents) of cinnamonitrile was used instead of 916 g (17 mol, 2.5 equivalents) of acrylonitrile, the melting and reaction temperature was changed to 80° C. to 85° C. and the stirring time after completion of the dropwise addition was changed from 3 hours to 4 hours, 2,491 g of isoidide dicinnamonitrile, a compound of Formula 7-4 was obtained in the same manner as in Example I-A1. At this time, the yield was 90%.

[Formula 7-4]

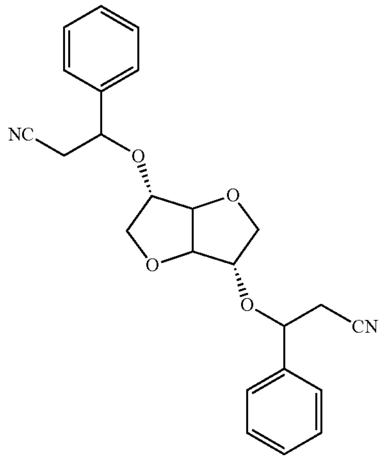

$^1H$ NMR (δ ppm; DMSO-$d_6$): 2.74 (1H, dd), 2.82 (1H, dd), 3.02 (1H, dd), 3.11 (1H, dd), 3.50 (1H, m), 3.59 (1H, m), 3.73 (1H, dd), 3.82 (1H, dd), 3.95 (1H, d), 4.01 (1H, d), 4.06 (1H, dd), 4.15 (1H, dd), 4.30 (1H, t), 4.42 (1H, t), 7.04-7.45 (10H, m)

MS(m/e): 404

Example I-C5: Preparation of Isoidide Di(3-Furyl)Acrylonitrile

Except that 1,000 g (6.8 mol, 1.0 equivalent) of isoidide was used instead of 1,000 g (6.8 mol, 1.0 equivalent) of isosorbide, 2,025 g (17 moles, 2.5 equivalents) of 3-(furan-2-yl)prop-2-enenitrile was used instead of 916 g (17 moles, 2.5 equivalents) of acrylonitrile, the melting and reaction temperature was changed to 80° C. to 85° C. and the stirring time after completion of the dropwise addition was changed from 3 hours to 5 hours, 2,288 g of isoidide di(3-furyl) acrylonitrile, a compound of Formula 7-5 was obtained in the same manner as in Example I-A1. At this time, the yield was 87%.

[Formula 7-5]

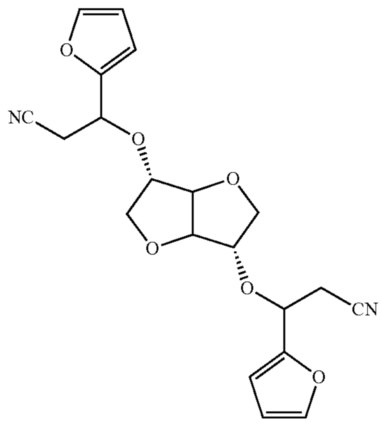

$^1H$ NMR (δ ppm; DMSO-$d_6$): 2.81 (1H, dd), 2.88 (1H, dd), 3.07 (1H, dd), 3.32 (1H, dd), 3.51 (1H, m), 3.62 (1H, m), 3.76 (1H, dd), 3.88 (1H, dd), 4.05 (1H, dd), 4.17 (1H, dd), 4.38 (1H, t), 4.57 (1H, t), 6.15-6.30 (4H, m), 7.37-7.43 (2H, m)

MS(m/e): 384

Example I-C6: Preparation of Isoidide Di(3-Cyclohexyl)Acrylonitrile

Except that 1,000 g (6.8 mol, 1.0 equivalent) of isoidide was used instead of 1,000 g (6.8 mol, 1.0 equivalent) of isosorbide, 2,299 g (17 moles, 2.5 equivalents) of cyclohexane acrylonitrile was used instead of 916 g (17 moles, 2.5 equivalents) of acrylonitrile, the melting and reaction temperature was changed to 80° C. to 85° C. and the stirring time after completion of the dropwise addition was changed from 3 hours to 4 hours, 2,423 g of isoidide di(3-cyclohexyl) acrylonitrile, a compound of Formula 7-6 was obtained in the same manner as in Example I-A1. At this time, the yield was 85%.

[Formula 7-6]

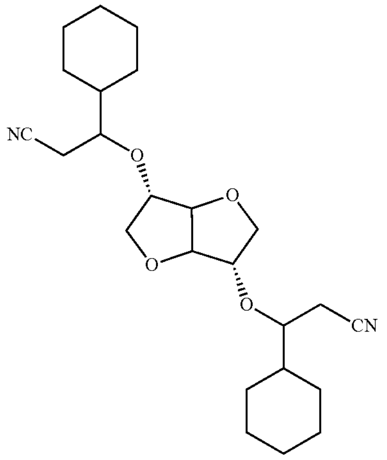

$^1H$ NMR (δ ppm; DMSO-$d_6$): 1.34-1.86 (22H, m), 2.45 (1H, dd), 2.59 (1H, dd), 2.73 (1H, dd), 2.80 (1H, dd), 2.90 (1H, m), 3.43 (1H, m), 3.52 (1H, dd), 3.59 (1H, dd), 3.62 (1H, d), 3.74 (1H, d), 3.80 (1H, dd), 3.96 (1H, dd), 4.19 (1H, t), 4.33 (1H, t)

MS(m/e): 416

<Preparation of Dianhydrohexitol Diamine Compound (Compound of Formula A")>

Example I-D1: Preparation of Isosorbide Dipropylamine 1,000 g of isosorbide diacrylonitrile, the compound of Formula 1-1 prepared in Example I-A1, 2,000 g of purified water, 50 g of Raney nickel and 300 g of ammonia water were put into a high-pressure reactor and sealed, and then the gas inside the sealed reactor was removed using nitrogen and a vacuum pump at room temperature, and then hydrogen was added at a pressure of 10 bar. While maintaining the hydrogen pressure, the internal temperature was heated to 130° C. and the mixture was stirred for 4 hours. After the reaction was completed, the Raney nickel catalyst was recovered through filtration, and remaining aqueous ammonia and water were removed as much as possible using a concentrator. The concentrated solution from which the ammonia water and water was removed were distilled using a fractional distillation apparatus to obtain 898 g of isosorbide dipropylamine, a compound of the following Formula 2-1. At this time, the yield was 87%.

[Formula 2-1]

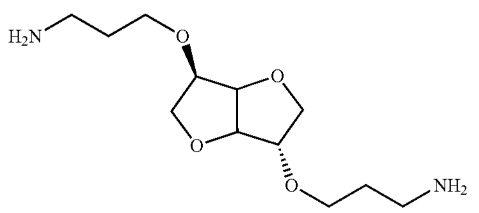

$^1$H NMR (δ ppm; methanol-$d_3$): 1.69 (2H, m), 1.73 (2H, m), 2.65 (2H, t), 2.72 (2H, t), 3.37 (2H, t), 3.41 (2H, t), 3.47-3.51 (2H, m), 3.70-3.76 (2H, m), 3.99-4.05 (2H, m), 4.07-4.11 (2H, m)

MS(m/e): 260

Example I-D2: Preparation of Isosorbide Dicrotonoamine

Except that 1,000 g of isosorbide dicrotononitrile of Example I-A2 was used instead of 1,000 g of isosorbide diacrylonitrile of Example I-A1, 875 g of isosorbide dicrotonoamine, a compound of Formula 2-2 was obtained in the same manner as in Example I-D1. At this time, the yield was 85%.

[Formula 2-2]

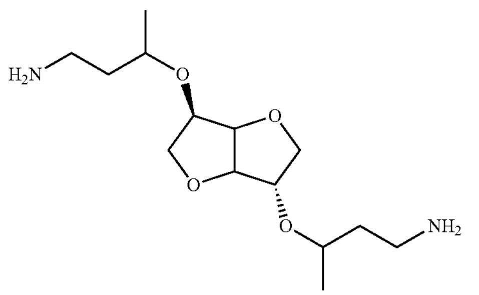

$^1$H NMR (δ ppm; DMSO-$d_6$): 1.21 (3H, d), 1.23 (3H, d), 1.68 (2H, m), 1.72 (2H, m), 2.65 (2H, t), 2.70 (2H, t), 3.01 (1H, m), 3.14 (1H, m), 3.52 (1H, m), 3.58 (1H, m), 3.76 (1H, dd), 3.79 (1H, dd), 3.93 (1H, d), 3.99 (1H, d), 4.02 (1H, dd), 4.08 (1H, dd)

MS(m/e): 288

Example I-D3: Preparation of Isosorbide Dimethacryloamine

Except that 1,000 g of isosorbide dimethacrylonitrile of Example I-A3 was used instead of 1,000 g of isosorbide diacrylonitrile of Example I-A1, 905 g of isosorbide dimethacryloamine, a compound of Formula 2-3 was obtained in the same manner as in Example I-D1. At this time, the yield was 88%.

[Formula 2-3]

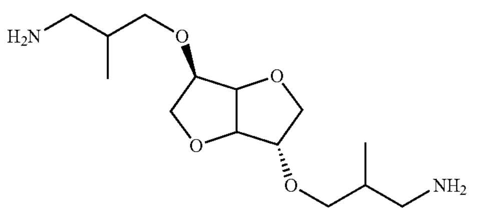

$^1$H NMR (δ ppm; DMSO-$d_6$): 1.06 (3H, d), 1.09 (3H, d), 2.22 (2H, m), 2.25 (2H, m), 2.48 (1H, dd), 2.54 (1H, dd), 2.73 (1H, dd), 2.77 (1H, dd), 3.20 (1H, dd), 3.28 (1H, dd), 3.45 (1H, dd), 3.49 (1H, dd), 3.51 (1H, m), 3.57 (1H, m), 3.74 (1H, dd), 3.79 (1H, dd), 3.94 (1H, d), 4.00 (1H, d), 4.01 (1H, dd), 4.03 (1H, dd)

MS(m/e): 288

Example I-D4: Preparation of Isosorbide Dicinnamoamine

Except that 1,000 g of isosorbide dicinnamonitrile of Example I-A4 was used instead of 1,000 g of isosorbide diacrylonitrile of Example I-A1, 815 g of isosorbide dicinnamoamine, a compound of Formula 2-4 was obtained in the same manner as in Example I-D1. At this time, the yield was 80%.

[Formula 2-4]

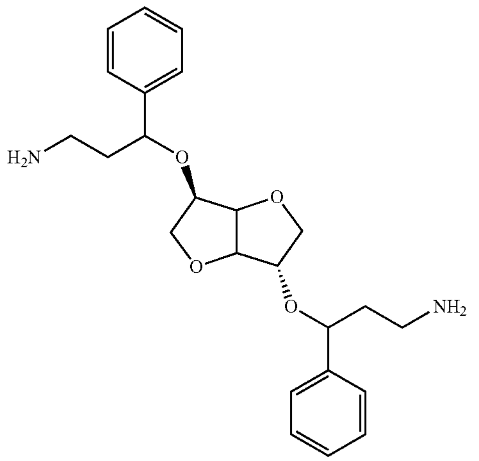

$^1$H NMR (δ ppm; DMSO-$d_6$): 2.01 (4H, m), 2.67 (4H, m), 3.50-3.62 (4H, m), 3.81 (1H, dd), 3.88 (1H, dd), 4.05 (1H, dd), 4.10 (1H, dd), 4.38 (1H, t), 4.42 (1H, t), 6.14-6.24 (4H, m), 7.25-7.35 (2H, m)

MS(m/e): 412

Example I-D5: Preparation of Isosorbide Di(3-Furyl)Acryloamine

Except that 1,000 g of isosorbide di(3-furyl)acrylonitrile of Example I-A5 was used instead of 1,000 g of isosorbide diacrylonitrile of Example I-A1, 815 g of isosorbide di(3-furyl)acryloamine, a compound of Formula 2-5 was obtained in the same manner as in Example I-D1. At this time, the yield was 83%.

[Formula 2-5]

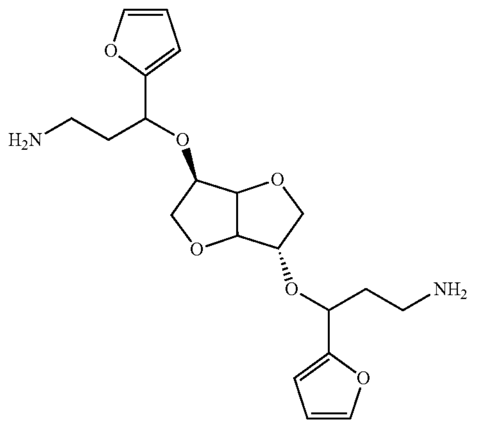

$^1$H NMR (δ ppm; DMSO-$d_6$): 2.01 (4H, m), 2.67 (4H, m), 3.50-3.62 (4H, m), 3.81 (1H, dd), 3.88 (1H, dd), 4.05 (1H, dd), 4.10 (1H, dd), 4.38 (1H, t), 4.42 (1H, t), 6.14-6.24 (4H, m), 7.25-7.35 (2H, m)

MS(m/e): 392

Example I-D6: Preparation of Isosorbide Di(3-Cyclohexyl)Acryloamine

Except that 1,000 g of isosorbide di(3-cyclohexyl)acrylonitrile of Example I-A6 was used instead of 1,000 g of isosorbide diacrylonitrile of Example I-A1, 803 g of isosorbide di(3-cyclohexyl)acryloamine, a compound of Formula 2-6 was obtained in the same manner as in Example I-D1. At this time, the yield was 79%.

[Formula 2-6]

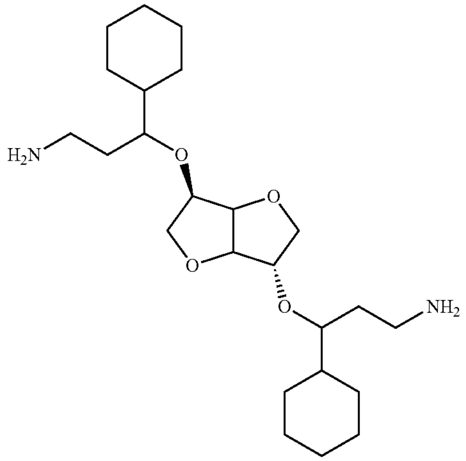

$^1$H NMR (δ ppm; DMSO-$d_6$): 1.24-1.78 (26H, m), 2.65 (4H, m), 2.79 (1H, m), 2.88 (1H, m), 3.51-3.59 (4H, m), 3.62 (1H, d), 3.70 (1H, dd), 3.75 (1H, dd), 3.96 (1H, dd), 3.88 (1H, dd)

MS(m/e): 424

Example I-E1: Preparation of Isomannide Dipropylamine

Except that 1,000 g of isomannide diacrylonitrile of Example I-B1 was used instead of 1,000 g of isosorbide diacrylonitrile of Example I-A1, 857 g of isomannide dipropylamine, a compound of Formula 5-1 was obtained in the same manner as in Example I-D1. At this time, the yield was 83%.

[Formula 5-1]

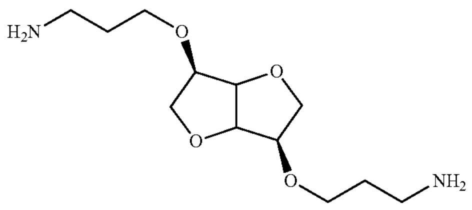

$^1$H NMR (δ ppm; DMSO-$d_6$): 1.66 (2H, m), 1.71 (2H, m), 2.60 (2H, t), 2.66 (2H, t), 3.35 (2H, t), 3.41 (2H, t), 3.49-3.55 (2H, m), 3.69-3.76 (2H, m), 3.94-3.98 (2H, m), 4.01-4.06 (2H, m)

MS(m/e): 260

Example I-E2: Preparation of Isomannide Dicrotonoamine

Except that 1,000 g of isomannide dicrotononitrile of Example I-B2 was used instead of 1,000 g of isosorbide diacrylonitrile of Example I-A1, 875 g of isomannide dicrotonoamine, a compound of Formula 5-2 was obtained in the same manner as in Example I-D1. At this time, the yield was 85%.

[Formula 5-2]

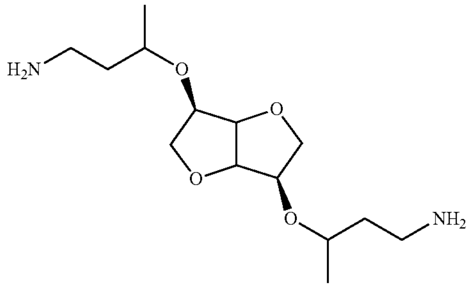

$^1$H NMR (δ ppm; DMSO-$d_6$): 1.17 (3H, d), 1.21 (3H, d), 1.68-1.72 (4H, m), 2.58 (2H, t), 2.64 (2H, t), 2.97 (1H, m), 3.09 (1H, m), 3.50-3.56 (2H, m), 3.70 (1H, dd), 3.76 (1H, dd), 3.90 (1H, d), 3.98-4.02 (2H, m), 4.08 (1H, dd)

MS(m/e): 288

Example I-E3: Preparation of Isomannide Dimethacryloamine

Except that 1,000 g of isomannide dimethacrylonitrile of Example I-B3 was used instead of 1,000 g of isosorbide diacrylonitrile of Example I-A1, 854 g of isomannide dimethacryloamine, a compound of Formula 5-3 was obtained in the same manner as in Example I-D1. At this time, the yield was 83%.

[Formula 5-3]

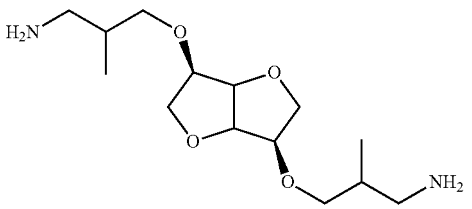

$^1$H NMR (δ ppm; DMSO-$d_6$): 1.03 (3H, d), 1.08 (3H, d), 2.17-2.23 (4H, m), 2.41 (1H, dd), 2.48 (1H, dd), 2.70 (1H, dd), 2.76 (1H, dd), 3.14 (1H, dd), 3.21 (1H, dd), 3.37 (1H, dd), 3.45 (1H, dd), 3.49-3.55 (2H, m), 3.67 (1H, dd), 3.75 (1H, dd), 3.94-4.00 (2H, m), 4.04 (1H, dd), 4.09 (1H, dd)

MS(m/e): 288

Example I-E4: Preparation of Isomannide Dicinnamoamine

Except that 1,000 g of isomannide dicinnamonitrile of Example I-B4 was used instead of 1,000 g of isosorbide diacrylonitrile of Example I-A1, 846 g of isomannide dicinnamoamine, a compound of Formula 5-4 was obtained in the same manner as in Example I-D1. At this time, the yield was 83%.

[Formula 5-4]

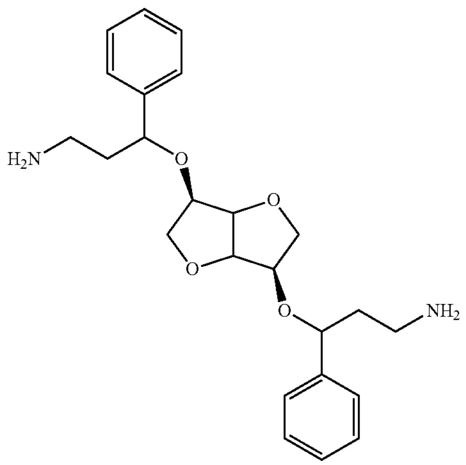

$^1$H NMR (δ ppm; DMSO-$d_6$): 1.94 (4H, m), 2.52 (3H, t), 2.66 (3H, t), 3.41 (1H, m), 3.57 (1H, m), 3.73 (1H, dd), 3.80 (1H, dd), 3.88 (1H, d), 3.98-4.01 (2H, m), 4.08 (1H, dd), 4.13 (1H, t), 4.22 (1H, t), 7.11-7.36 (10H, m)

MS(m/e): 412

Example I-E5: Preparation of Isomannide Di(3-Furyl)Acryloamine

Except that 1,000 g of isomannide di(3-furyl)acrylonitrile of Example I-B5 was used instead of 1,000 g of isosorbide diacrylonitrile of Example I-A1, 807 g of isomannide di(3-furyl)acryloamine, a compound of Formula 5-5 was obtained in the same manner as in Example I-D1. At this time, the yield was 79%.

[Formula 5-5]

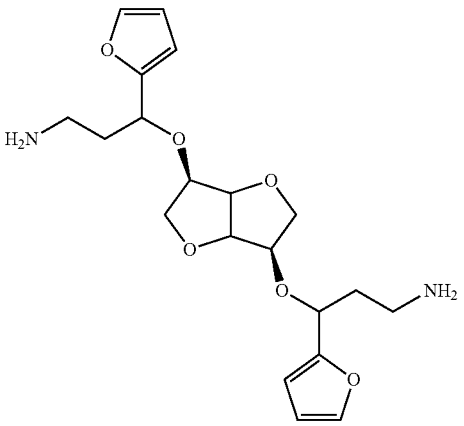

$^1$H NMR (δ ppm; DMSO-$d_6$): 1.89 (4H, m), 2.42 (4H, m), 3.50-3.62 (4H, m), 3.75 (1H, dd), 3.83 (1H, dd), 4.05-4.10 (2H, m), 4.28 (1H, t), 4.35 (1H, t), 6.08-6.20 (4H, m), 7.01-7.24 (2H, m)

MS(m/e): 392

Example I-E6: Preparation of Isomannide Di(3-Cyclohexyl)Acryloamine

Except that 1,000 g of isomannide di(3-cyclohexyl)acrylonitrile of Example I-B6 was used instead of 1,000 g of isosorbide diacrylonitrile of Example I-A1, 856 g of isomannide di(3-cyclohexyl)acryloamine, a compound of Formula 5-6 was obtained in the same manner as in Example I-D1. At this time, the yield was 84%.

[Formula 5-6]

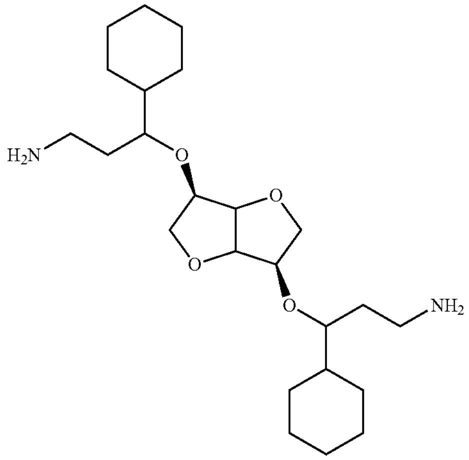

$^1$H NMR (δ ppm; DMSO-$d_6$): 1.11-1.64 (26H, m), 2.35 (4H, m), 2.69 (1H, m), 2.80 (1H, m), 3.44-3.52 (4H, m), 3.57 (1H, d), 3.65 (1H, dd), 3.75 (1H, dd), 3.84 (1H, dd), 4.08 (1H, dd)

MS(m/e): 424

Example I-F1: Preparation of Isoidide Dipropylamine

Except that 1,000 g of isoidide diacrylonitrile of Example I-C1 was used instead of 1,000 g of isosorbide diacrylonitrile of Example I-A1, 918 g of isoidide dipropylamine, a compound of Formula 8-1 was obtained in the same manner as in Example I-D1. At this time, the yield was 89%.

[Formula 8-1]

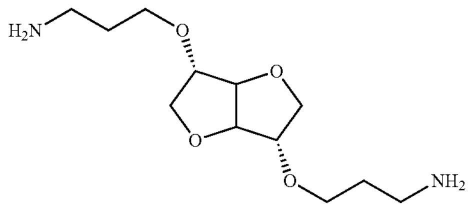

$^1H$ NMR (δ ppm; DMSO-$d_6$): 1.72 (2H, m), 1.76 (2H, m), 2.65 (2H, t), 2.71 (2H, t), 3.31 (2H, t), 3.35 (2H, t), 3.50-3.53 (2H, m), 3.68-3.76 (2H, m), 3.90-3.99 (2H, m), 4.04-4.10 (2H, m)

MS(m/e): 260

Example I-F2: Preparation of Isoidide Dicrotonoamine

Except that 1,000 g of isoidide dicrotononitrile of Example I-C2 was used instead of 1,000 g of isosorbide diacrylonitrile of Example I-A1, 833 g of isoidide dicrotonoamine, a compound of Formula 8-2 was obtained in the same manner as in Example I-D1. At this time, the yield was 81%.

[Formula 8-2]

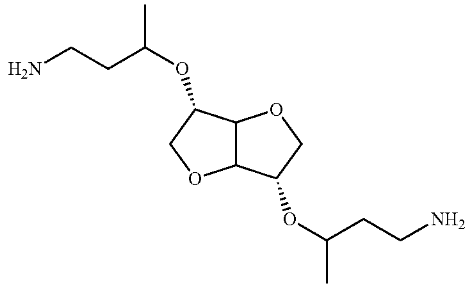

$^1H$ NMR (δ ppm; DMSO-$d_6$): 1.29-1.43 (6H, m), 1.76-1.84 (4H, m), 2.73 (2H, t), 2.87 (2H, t), 3.15 (1H, m), 3.29 (1H, m), 3.64 (1H, m), 3.71 (1H, m), 3.80-3.86 (2H, m), 3.97 (1H, d), 4.02 (1H, d), 4.08 (1H, dd), 4.27 (1H, dd)

MS(m/e): 288

Example I-F3: Preparation of Isoidide Dimethacryloamine

Except that 1,000 g of isoidide dimethacrylonitrile of Example I-C3 was used instead of 1,000 g of isosorbide diacrylonitrile of Example I-A1, 895 g of isoidide dimethacryloamine, a compound of Formula 8-3 was obtained in the same manner as in Example I-D1. At this time, the yield was 87%.

[Formula 8-3]

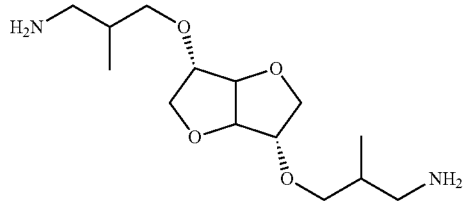

$^1H$ NMR (δ ppm; DMSO-$d_6$): 1.15 (3H, d), 1.23 (3H, d), 2.30 (2H, m), 2.35 (2H, m), 2.60 (1H, dd), 2.69 (1H, dd), 2.77 (1H, dd), 2.89 (1H, dd), 3.20-3.28 (2H, m), 3.56 (1H, dd), 3.52 (1H, dd), 3.60-3.64 (2H, m), 3.77 (1H, dd), 3.88 (1H, dd), 4.01 (1H, d), 4.08 (1H, d), 4.19 (1H, dd), 4.33 (1H, dd)

MS(m/e): 288

Example I-F4: Preparation of Isoidide Dicinnamoamine

Except that 1,000 g of isoidide dicinnamonitrile of Example I-C4 was used instead of 1,000 g of isosorbide diacrylonitrile of Example I-A1, 836 g of isoidide dicinnamoamine, a compound of Formula 8-4 was obtained in the same manner as in Example I-D1. At this time, the yield was 82%.

[Formula 8-4]

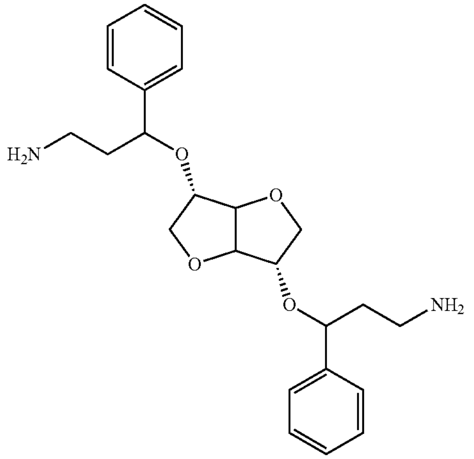

$^1H$ NMR (δ ppm; DMSO-$d_6$): 2.21 (4H, m), 2.53 (3H, t), 2.77 (3H, t), 3.67 (1H, m), 3.74 (1H, m), 3.85 (1H, dd), 3.94 (1H, dd), 4.01-4.14 (2H, m), 4.21 (1H, dd), 4.31 (1H, dd), 4.36 (1H, t), 4.62 (1H, t), 7.44-7.60 (10H, m)

MS(m/e): 412

Example I-F5: Preparation of Isoidide Di(3-Furyl)Acryloamine

Except that 1,000 g of isoidide di(3-furyl)acrylonitrile of Example I-C5 was used instead of 1,000 g of isosorbide diacrylonitrile of Example I-A1, 786 g of isoidide di(3-furyl)acryloamine, a compound of Formula 8-5 was obtained in the same manner as in Example I-D1. At this time, the yield was 77%.

[Formula 8-5]

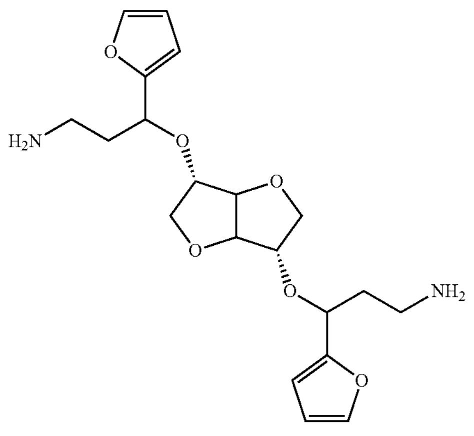

$^1H$ NMR (δ ppm; DMSO-$d_6$): 2.10 (4H, m), 2.92 (4H, m), 3.53-3.74 (4H, m), 3.80 (1H, dd), 3.91 (1H, dd), 4.09 (1H, dd), 4.24 (1H, dd), 4.38-4.42 (2H, m), 6.34-6.59 (4H, m), 7.33-7.43 (2H, m)
MS(m/e): 392

Example I-F6: Preparation of Isoidide Di(3-Cyclohexyl)Acryloamine

Except that 1,000 g of isoidide di(3-cyclohexyl)acrylonitrile of Example I-C6 was used instead of 1,000 g of isosorbide diacrylonitrile of Example I-A1, 826 g of isoidide di(3-cyclohexyl)acryloamine, a compound of Formula 8-6 was obtained in the same manner as in Example I-D1. At this time, the yield was 81%.

[Formula 8-6]

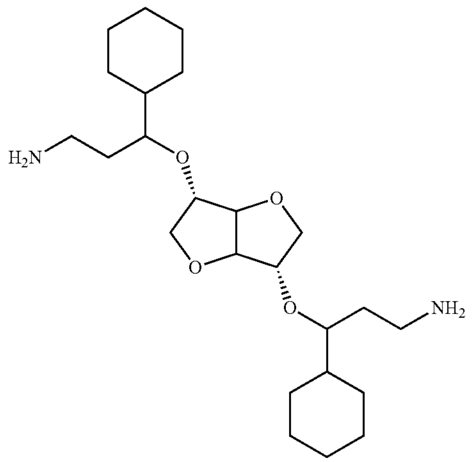

$^1H$ NMR (δ ppm; DMSO-$d_6$): 1.19-1.88 (26H, m), 2.81 (4H, m), 2.97-3.13 (2H, m), 3.49-3.61 (4H, m), 3.74 (1H, d), 3.79 (1H, dd), 3.83 (1H, dd), 3.94 (1H, dd), 4.18 (1H, dd)
MS(m/e): 424

<Preparation of dianhydrohexitol diisocyanate compound (compound of Formula A)>

Example I-G1: Isosorbide Dipropylisocyanate (Using Carbonate)

After adding 300 ml of methylene chloride to a 4-neck reactor equipped with a condenser, an internal thermometer and a nitrogen injection line, 2.4 g of 4-dimethylaminopyridine (DMAP: 0.02 mol, 0.05 equivalent) and 366.7 g of di-tert-butyldicarbonate (DBDC: 1.2 mol, 3.0 equivalent) were added and dissolved in methylene chloride. Subsequently, the temperature inside the reactor was maintained at 0° C. to 5° C. using an ice bath under a nitrogen atmosphere. A solution prepared by dissolving 100 g (0.4 mol, 1 equivalent) of isosorbide dipropylamine prepared in Example I-D1 in 200 ml of methylene chloride was added dropwise to the reactor, at which time the temperature inside the reactor was kept at 0° C. to 5° C. After the dropwise addition was completed, the temperature inside the reactor was raised to 25° C., and the reaction was performed for 3 hours.

Methylene chloride was removed from the obtained reaction product using a concentrator, and isosorbide dipropylisocyanate was extracted from the reaction product using hexane and tertiary distilled water. After removing moisture from the extract using magnesium sulfate, hexane was removed from the extract using a concentrator.

By fractional distillation of the extract from which the moisture and hexane were removed, isosorbide dipropylisocyanate was purified, and 85 g of isosorbide dipropylisocyanate of Formula 3-1, which is a pale-yellow product, was obtained. At this time, the yield was 71%.

As a result of confirming the isocyanate content in the obtained isosorbide dipropylisocyanate through the method of measuring the potential difference of ISO 14896, it was confirmed to be at the level of 26.8+0.2 mass $\%_{NCO}$ (theoretical value=26.9 mass % NCO). The mass $\%_{NCO}$, which is a unit of the isocyanate content, refers to the mass % of the NCO group present in the sample, isosorbide dipropylisocyanate.

Example I-G1-1: Isosorbide Dipropylisocyanate (Using Triphosgene)

After adding 30 ml of methylene chloride into a reactor equipped with a phosgene gas inlet, an internal thermometer, a dropping funnel, a dry ice cooling condenser and a gas discharge line connected to a hood line, the temperature inside the reactor is cooled to −50° C. using dry ice and maintained. Then, after connecting the phosgene generating device comprising 11.4 g (0.04 mol, 1 equivalent) of triphosgene and the reactor with a hose, the phosgene generating device was heated to 100° C. using an oil bath, and 10 g (0.04 mol, 1 equivalent) of isosorbide dipropylamine prepared in Example I-D1 was slowly added dropwise and stirred vigorously, and the temperature inside the reactor was maintained at −30° C. Thereafter, a mixed solution obtained by dissolving 11.7 g (0.12 mol, 3 equivalents) of triethylamine in 20 ml of methylene chloride was slowly added dropwise so that the temperature inside the reactor was maintained at −25° C. to −30° C. After the dropwise addition was completed, the temperature inside the reactor was raised and reacted at 0° C. for 30 minutes.

Methylene chloride was removed from the reaction product obtained by using a concentrator, and the reaction product was dissolved in hexane and washed 3 times with IN HCl (10 mL) solution, 1 time with IN NaOH (10 mL) solution and 3 times with tertiary distilled water (20 ml). Then, water in the organic layer was removed using magnesium sulfate, and hexane was removed from the extract using a concentrator.

By fractional distillation of the extract from which the moisture and hexane were removed, isosorbide dipropylisocyanate was purified, and 9.6 g of isosorbide dipropylisocyanate of Formula 3-1, which is a pale-yellow product, was obtained. At this time, the yield was 88%.

As a result of confirming the isocyanate content in the obtained isosorbide dipropylisocyanate through the method of measuring the potential difference of ISO 14896, it was confirmed to be at the level of 27.0+0.3 mass $\%_{NCO}$ (theoretical value=26.9 mass % NCO).

[Formula 3-1]

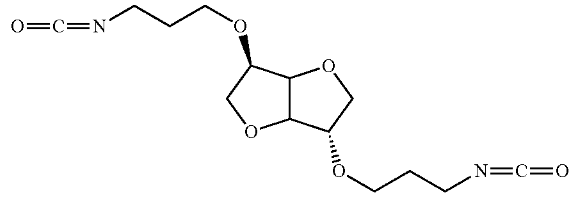

$^{1}H$ NMR (δ ppm; $CDCl_3$): 1.68 (2H, m), 1.77 (2H, m), 3.31 (2H, t), 3.35 (2H, t), 3.37 (2H, t), 3.44 (2H, t), 3.51-3.59 (2H, m), 3.65-3.72 (2H, m), 3.94 (1H, dd), 3.99 (1H, dd), 4.05-4.12 (2H, m)

MS(m/e): 312

Example I-G2: Preparation of Isosorbide Dicrotonoisocyanate

Except that 100 g of isosorbide dicrotonoamine of Example I-D2 was used instead of 100 g of isosorbide dipropylamine of Example I-D1, 81 g of isosorbide dicrotonoisocyanate, the compound of Formula 3-2 was obtained in the same manner as in Example I-G1. At this time, the yield was 69%.

As a result of confirming the isocyanate content in the obtained isosorbide dicrotonoisocyanate through the method of measuring the potential difference of ISO 14896, it was confirmed to be at the level of 24.8+0.3 mass $\%_{NCO}$ (theoretical value=24.7 mass % NCO).

[Formula 3-2]

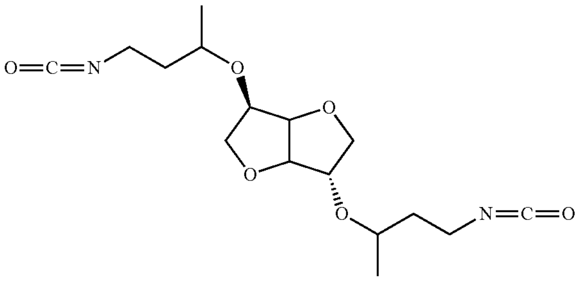

$^{1}H$ NMR (δ ppm; $CDCl_3$): 1.21 (3H, dd), 1.28 (3H, dd), 1.51-1.60 (4H,m), 2.86-2.99 (2H, m), 3.30 (2H, d), 3.34 (2H, d), 3.50-3.56 (2H, m), 3.73-3.80 (2H, m), 3.90-3.94 (2H, m), 4.03 (1H, dd), 4.09 (1H, dd) MS(m/e): 340

Example I-G3: Preparation of Isosorbide Dimethacryloisocyanate

Except that 100 g of isosorbide dimethacryloamine of Example I-D3 was used instead of 100 g of isosorbide dipropylamine of Example I-D1 and the reaction time after completion of the dropwise addition was changed from 3 hours to 5 hours, 60 g of isosorbide dimethacryloisocyanate, the compound of Formula 3-3 was obtained in the same manner as in Example I-G1. At this time, the yield was 51%.

As a result of confirming the isocyanate content in the obtained isosorbide dimethacryloisocyanate through the method of measuring the potential difference of ISO 14896, it was confirmed to be at the level of 24.1+0.4 mass $\%_{NCO}$ (theoretical value=24.7 mass $\%_{NCO}$).

[Formula 3-3]

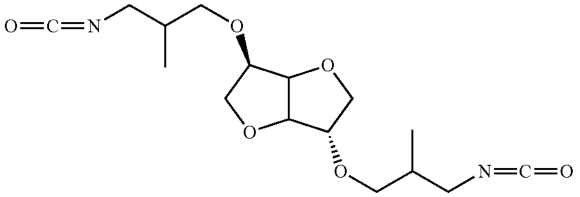

$^{1}H$ NMR (δ ppm; $CDCl_3$): 1.01 (3H, dd), 1.10 (3H, dd), 1.94-2.01 (2H, m), 3.11-3.18 (4H, m), 3.35-3.41 (4H, m), 3.50-3.54 (2H, m), 3.79-3.84 (2H, m), 3.94-4.04 (4H, m)

MS(m/e): 340

Example I-G4: Preparation of Isosorbide Dicinnamoisocyanate

Except that 100 g of isosorbide dicinnamoamine of Example I-D4 was used instead of 100 g of isosorbide dipropylamine of Example I-D1, 72 g of isosorbide dicinnamoisocyanate, the compound of Formula 3-4 was obtained in the same manner as in Example I-G1. At this time, the yield was 64%.

As a result of confirming the isocyanate content in the obtained isosorbide dicinnamoisocyanate through the method of measuring the potential difference of ISO 14896, it was confirmed to be at the level of 18.3+0.1 mass $\%_{NCO}$ (theoretical value=18.1 mass % NCO).

[Formula 3-4]

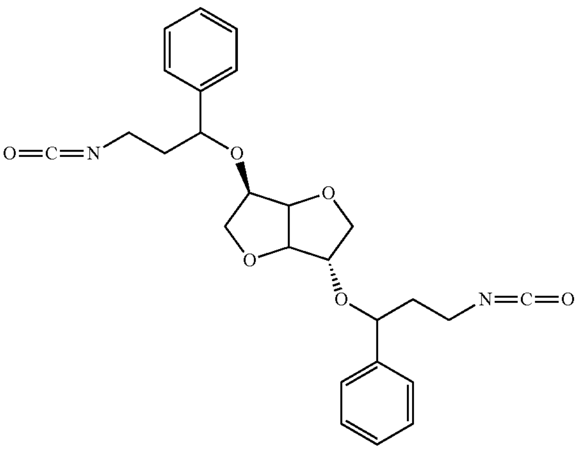

$^{1}H$ NMR (δ ppm; $CDCl_3$): 1.71-1.80 (4H, m), 3.35-3.41 (4H, m), 3.48-3.52 (2H, m), 3.74-3.78 (2H, m), 3.96-4.03 (4H, m), 4.32 (1H, dd), 4.52 (1H, dd), 7.20-7.41 (10H, m)

MS(m/e): 464

Example I-G5: Preparation of Isosorbide Di(3-Furyl)Acryloisocyanate

Except that 100 g of isosorbide di(3-furyl)acryloamine of Example I-D5 was used instead of 100 g of isosorbide dipropylamine of Example I-D1, 76 g of isosorbide di(3-furyl)acryloisocyanate, the compound of Formula 3-5 was obtained in the same manner as in Example I-G1. At this time, the yield was 67%.

As a result of confirming the isocyanate content in the obtained isosorbide di(3-furyl)acryloisocyanate through the method of measuring the potential difference of ISO 14896, it was confirmed to be at the level of 19.3+0.3 mass $\%_{NCO}$ (theoretical value=18.9 mass $\%_{NCO}$).

[Formula 3-5]

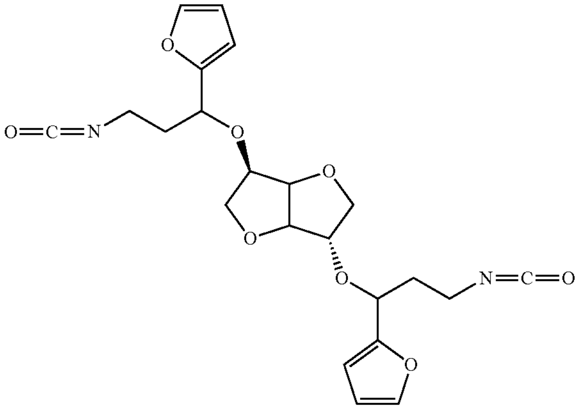

$^1$H NMR (δ ppm; $CDCl_3$): 1.81 (2H, m), 1.86 (2H, m), 3.20 (2H, t), 3.27 (2H, t), 3.41-3.48 (2H, m), 3.74-3.78 (2H, m), 3.96-4.03 (4H, m), 4.42 (1H, t), 4.51 (1H, t), 6.20-6.27 (4H, m), 7.34 (1H, dd), 7.45 (1H, dd)

MS(m/e): 444

Example I-G6: Preparation of Isosorbide Di(3-Cyclohexyl)Acryloisocyanate

Except that 100 g of isosorbide di(3-cyclohexyl)acryloamine of Example I-D6 was used instead of 100 g of isosorbide dipropylamine of Example I-D1, 82 g of isosorbide di(3-cyclohexyl)acryloisocyanate, the compound of Formula 3-6 was obtained in the same manner as in Example I-G1. At this time, the yield was 73%.

As a result of confirming the isocyanate content in the obtained isosorbide di(3-cyclohexyl)acryloisocyanate through the method of measuring the potential difference of ISO 14896, it was confirmed to be at the level of 17.9+0.1 mass $\%_{NCO}$ (theoretical value=17.6 mass $\%_{NCO}$).

[Formula 3-6]

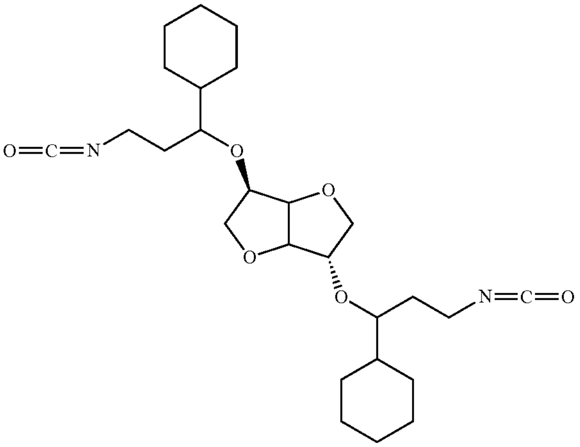

$^1$H NMR (δ ppm; $CDCl_3$): 0.92-1.78 (26H, m), 2.74 (1H, m), 2.82 (1H, m), 3.24 (2H, t), 3.31 (2H, t), 3.43-3.50 (2H, m), 3.71-3.77 (2H, m), 3.94-4.01 (4H, m)

MS(m/e): 477

Example I-H1: Preparation of Isomannide Dipropylisocyanate

Except that 100 g of isomannide dipropylamine of Example I-E1 was used instead of 100 g of isosorbide dipropylamine of Example I-D1, 89 g of isomannide dipropylisocyanate, the compound of Formula 6-1 was obtained in the same manner as in Example I-G1. At this time, the yield was 74%.

As a result of confirming the isocyanate content in the obtained isomannide dipropylisocyanate through the method of measuring the potential difference of ISO 14896, it was confirmed to be at the level of 26.8+0.1 mass $\%_{NCO}$ (theoretical value=26.9 mass % NCO).

[Formula 6-1]

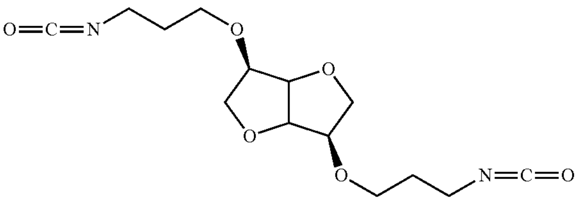

$^1$H NMR (δ ppm; $CDCl_3$): 1.62 (2H, m), 1.73 (2H, m), 3.25 (2H, t), 3.31 (2H, t), 3.38 (2H, t), 3.46 (2H, t), 3.54-3.61 (2H, m), 3.69-3.74 (2H, m), 3.90 (1H, dd), 3.98 (1H, dd), 4.09-17 (2H, m)

MS(m/e): 312

Example I-H2: Preparation of Isomannide Dicrotonoisocyanate

Except that 100 g of isomannide dicrotonoamine of Example I-E2 was used instead of 100 g of isosorbide dipropylamine of Example I-D1, 84 g of isomannide dicrotonoisocyanate, the compound of Formula 6-2 was obtained in the same manner as in Example I-G1. At this time, the yield was 71%.

As a result of confirming the isocyanate content in the obtained isomannide dicrotonoisocyanate through the method of measuring the potential difference of ISO 14896, it was confirmed to be at the level of 24.4+0.2 mass $\%_{NCO}$ (theoretical value=24.7 mass $\%_{NCO}$).

[Formula 6-2]

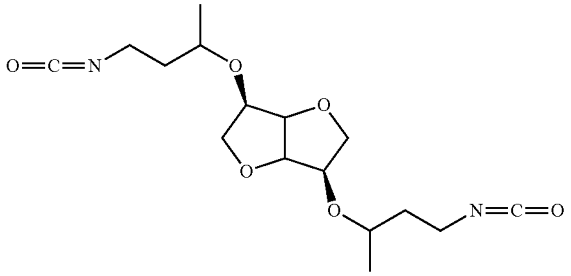

$^1$H NMR (δ ppm; $CDCl_3$): 1.14 (3H, dd), 1.23 (3H, dd), 1.46-1.52 (4H, m), 2.80-2.87 (2H, m), 3.19 (2H, d), 3.27 (2H, d), 3.48-3.54 (2H, m), 3.66-3.76 (2H, m), 3.87-3.91 (2H, m), 4.04 (1H, dd), 4.12 (1H, dd)

MS(m/e): 340

Example I-H3: Preparation of Isomannide Dimethacryloisocyanate

Except that 100 g of isomannide dimethacryloamine of Example I-E3 was used instead of 100 g of isosorbide dipropylamine of Example I-D1 and the reaction time after completion of the dropwise addition was changed from 3 hours to 5 hours, 51 g of isomannide dimethacryloisocyanate, the compound of Formula 6-3 was obtained in the same manner as in Example I-G1. At this time, the yield was 43%.

As a result of confirming the isocyanate content in the obtained isomannide dimethacryloisocyanate through the method of measuring the potential difference of ISO 14896, it was confirmed to be at the level of 25.1+0.3 mass $\%_{NCO}$ (theoretical value=24.7 mass $\%_{NCO}$).

[Formula 6-3]

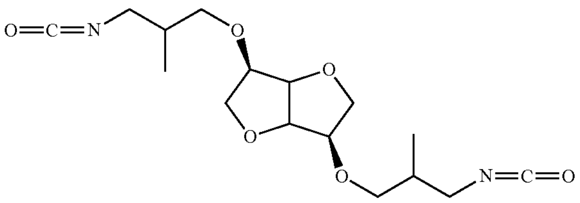

$^1$H NMR (δ ppm; $CDCl_3$): 0.94 (3H, dd), 1.07 (3H, dd), 1.88-2.00 (2H, m), 3.02-3.19 (4H, m), 3.37-3.45 (4H, m), 3.52-3.59 (2H, m), 3.71-3.80 (2H, m), 4.01-4.06 (4H, m)

MS(m/e): 340

Example I-H4: Preparation of Isomannide Dicinnamoisocyanate

Except that 100 g of isomannide dicinnamoamine of Example I-E4 was used instead of 100 g of isosorbide dipropylamine of Example I-D1, 78 g of isomannide dicinnamoisocyanate, the compound of Formula 6-4 was obtained in the same manner as in Example I-G1. At this time, the yield was 69%.

As a result of confirming the isocyanate content in the obtained isomannide dicinnamoisocyanate through the method of measuring the potential difference of ISO 14896, it was confirmed to be at the level of 18.0+0.1 mass $\%_{NCO}$ (theoretical value=18.1 mass $\%_{NCO}$).

[Formula 6-4]

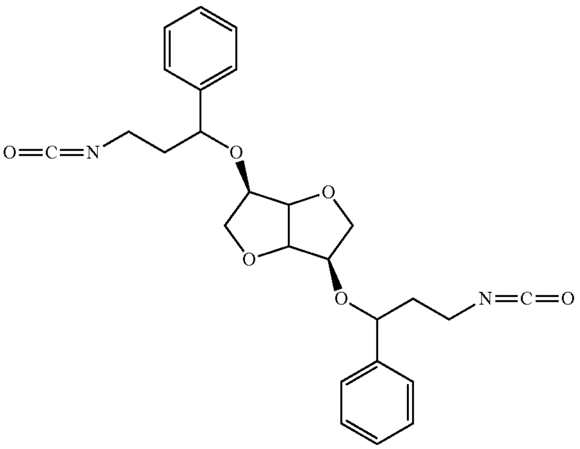

$^1$H NMR (δ ppm; $CDCl_3$): 1.63-1.74 (4H, m), 3.25-3.32 (4H, m), 3.50-3.57 (2H, m), 3.71-3.75 (2H, m), 3.92-3.98 (4H, m), 4.23 (1H, dd), 4.44 (1H, dd), 7.19-7.40 (10H, m)

MS(m/e): 464

Example I-H5: Preparation of Isomannide Di(3-Furyl)Acryloisocyanate

Except that 100 g of isomannide di(3-furyl)acryloamine of Example I-E5 was used instead of 100 g of isosorbide dipropylamine of Example I-D1, 75 g of isomannide di(3-furyl)acryloisocyanate, the compound of Formula 6-5 was obtained in the same manner as in Example I-G1. At this time, the yield was 66%.

As a result of confirming the isocyanate content in the obtained isomannide di(3-furyl)acryloisocyanate through the method of measuring the potential difference of ISO 14896, it was confirmed to be at the level of 18.8+0.4 mass $\%_{NCO}$ (theoretical value=18.9 mass $\%_{NCO}$).

[Formula 6-5]

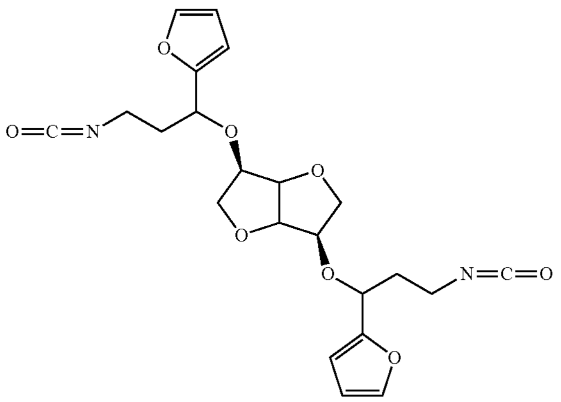

$^1$H NMR (δ ppm; $CDCl_3$): 1.77 (2H, m), 1.85 (2H, m), 3.15 (2H, t), 3.23 (2H, t), 3.34-3.40 (2H, m), 3.64-3.68 (2H, m), 3.93-3.99 (4H, m), 4.35 (1H, t), 4.46 (1H, t), 6.19-6.25 (4H, m), 7.28 (1H, dd), 7.38 (1H, dd)

MS(m/e): 444

Example I-H6: Preparation of Isomannide Di(3-Cyclohexyl)Acryloisocyanate

Except that 100 g of isomannide di(3-cyclohexyl)acryloamine of Example I-E6 was used instead of 100 g of isosorbide dipropylamine of Example I-D1, 70 g of isomannide di(3-cyclohexyl)acryloisocyanate, the compound of Formula 6-6 was obtained in the same manner as in Example I-G1. At this time, the yield was 62%.

As a result of confirming the isocyanate content in the obtained isomannide di(3-cyclohexyl)acryloisocyanate through the method of measuring the potential difference of ISO 14896, it was confirmed to be at the level of 17.4+0.4 mass $\%_{NCO}$ (theoretical value=17.6 mass $\%_{NCO}$).

[Formula 6-6]

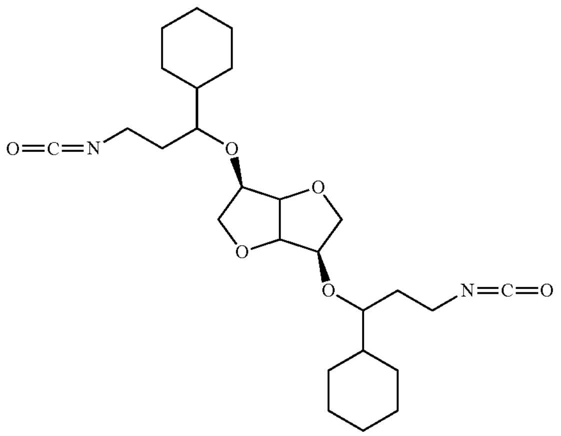

$^1$H NMR (δ ppm; $CDCl_3$): 0.89-1.81 (26H, m), 2.53 (1H, m), 2.70 (1H, m), 3.16 (2H, t), 3.28 (2H, t), 3.40-3.45 (2H, m), 3.68-3.74 (2H, m), 3.91-3.99 (4H, m)

MS(m/e): 477

Example I-11: Preparation of Isoidide Dipropylisocyanate

Except that 100 g of isoidide dipropylamine of Example I-F1 was used instead of 100 g of isosorbide dipropylamine of Example I-D1, 90 g of isoidide dipropylisocyanate, the compound of Formula 9-1 was obtained in the same manner as in Example I-G1. At this time, the yield was 75%.

As a result of confirming the isocyanate content in the obtained isoidide dipropylisocyanate through the method of measuring the potential difference of ISO 14896, it was confirmed to be at the level of 26.9+0.3 mass % NO (theoretical value=26.9 mass % NCO).

[Formula 9-1]

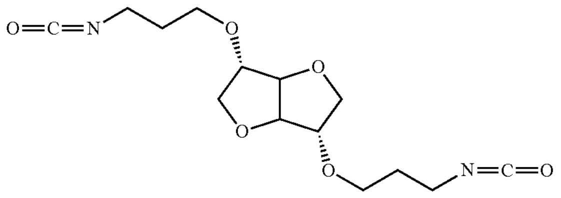

$^1$H NMR (δ ppm; $CDCl_3$): 1.79 (2H, m), 1.91 (2H, m), 3.31 (2H, t), 3.39 (2H, t), 3.52 (2H, t), 3.58 (2H, t), 3.62-3.68 (2H, m), 3.75-3.81 (2H, m), 3.96 (1H, dd), 4.08 (1H, dd), 4.16-4.25 (2H, m)

MS(m/e): 312

Example I-12: Preparation of Isoidide Dicrotonoisocyanate

Except that 100 g of isoidide dicrotonoamine of Example I-F2 was used instead of 100 g of isosorbide dipropylamine of Example I-D1, 77 g of isoidide dicrotonoisocyanate, the compound of Formula 9-2 was obtained in the same manner as in Example I-G1. At this time, the yield was 65%.

As a result of confirming the isocyanate content in the obtained isoidide dicrotonoisocyanate through the method of measuring the potential difference of ISO 14896, it was confirmed to be at the level of 24.9+0.2 mass $\%_{NCO}$ (theoretical value=24.7 mass % NCO).

[Formula 9-2]

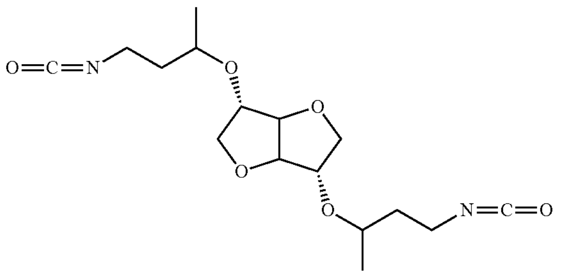

$^1$H NMR (δ ppm; $CDCl_3$): 1.19 (3H, dd), 1.32 (3H, dd), 1.56-1.63 (4H, m), 2.90-2.98 (2H, m), 3.37 (2H, d), 3.43 (2H, d), 3.61-3.68 (2H, m), 3.83-3.90 (2H, m), 3.97-4.05 (2H, m), 4.21 (1H, dd), 4.39 (1H, dd)

MS(m/e): 340

Example I-13: Preparation of Isoidide Dimethacryloisocyanate

Except that 100 g of isoidide dimethacryloamine of Example I-F3 was used instead of 100 g of isosorbide dipropylamine of Example I-D1 and the reaction time after completion of the dropwise addition was changed from 3 hours to 5 hours, 65 g of isoidide dimethacryloisocyanate, the compound of Formula 9-3 was obtained in the same manner as in Example I-G1. At this time, the yield was 55%.

As a result of confirming the isocyanate content in the obtained isoidide dimethacryloisocyanate through the method of measuring the potential difference of ISO 14896, it was confirmed to be at the level of 24.5+0.2 mass $\%_{NCO}$ (theoretical value=24.7 mass $\%_{NCO}$).

[Formula 9-3]

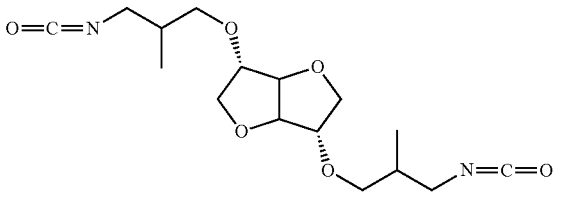

$^1H$ NMR (δ ppm; $CDCl_3$): 0.97 (3H, dd), 1.14 (3H, dd), 1.99-2.15 (2H, m), 3.26-3.37 (4H, m), 3.43-3.50 (4H, m), 3.58-3.64 (2H, m), 3.85-3.90 (2H, m), 4.06-4.13 (4H, m)

MS(m/e): 340

Example I-14: Preparation of Isoidide Dicinnamoisocyanate

Except that 100 g of isoidide dicinnamoamine of Example I-F4 was used instead of 100 g of isosorbide dipropylamine of Example I-D1, 82 g of isoidide dicinnamoisocyanate, the compound of Formula 9-4 was obtained in the same manner as in Example I-G1. At this time, the yield was 73%.

As a result of confirming the isocyanate content in the obtained isoidide dicinnamoisocyanate through the method of measuring the potential difference of ISO 14896, it was confirmed to be at the level of 18.3+0.4 mass $\%_{NCO}$ (theoretical value=18.1 mass $\%_{NCO}$).

[Formula 9-4]

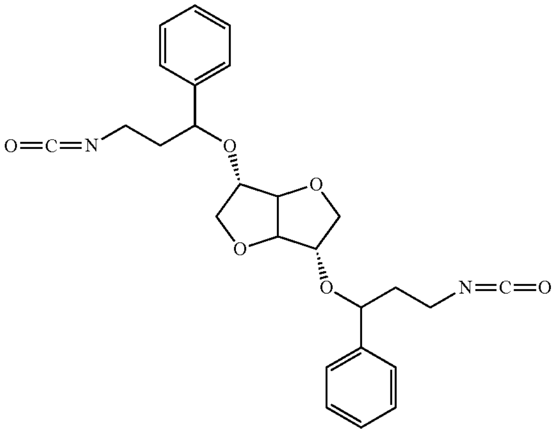

$^1H$ NMR (δ ppm; $CDCl_3$): 1.64-1.77 (4H, m), 3.45-3.51 (4H, m), 3.57-3.63 (2H, m), 3.41-3.74 (2H, m), 4.02-4.11 (4H, m), 4.48 (1H, dd), 4.63 (1H, dd), 7.17-7.36 (10H, m)

MS(m/e): 464

Example I-15: Preparation of Isoidide Di(3-Furyl)Acryloisocyanate

Except that 100 g of isoidide di(3-furyl)acryloamine of Example I-F5 was used instead of 100 g of isosorbide dipropylamine of Example I-D1, 69 g of isoidide di(3-furyl) acryloisocyanate, the compound of Formula 9-5 was obtained in the same manner as in Example I-G1. At this time, the yield was 61%.

As a result of confirming the isocyanate content in the obtained isoidide di(3-furyl)acryloisocyanate through the method of measuring the potential difference of ISO 14896, it was confirmed to be at the level of 19.1+0.3 mass $\%_{NCO}$ (theoretical value=18.9 mass $\%_{NCO}$).

[Formula 9-5]

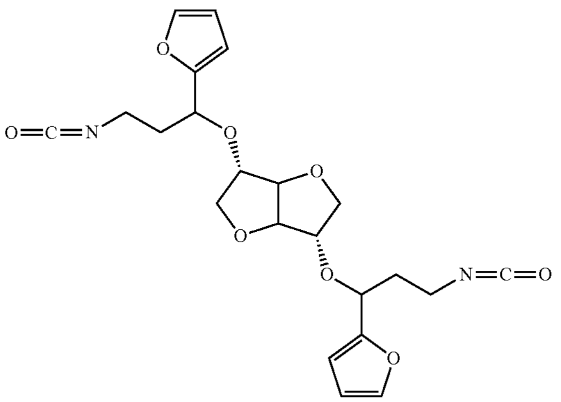

$^1H$ NMR (δ ppm; $CDCl_3$): 1.77 (2H, m), 1.90 (2H, m), 3.18 (2H, t), 3.25 (2H, t), 3.45-3.52 (2H, m), 3.77-3.82 (2H, m), 3.99-4.11 (4H, m), 4.49 (1H, t), 4.63 (1H, t), 6.23-6.34 (4H, m), 7.25 (1H, dd), 7.48 (1H, dd)

MS(m/e): 444

Example I-16: Preparation of Isoidide Di(3-Cyclohexyl)Acryloisocyanate

Except that 100 g of isoidide di(3-cyclohexyl)acryloamine of Example I-F6 was used instead of 100 g of isosorbide dipropylamine of Example I-D1, 64 g of isoidide di(3-cyclohexyl)acryloisocyanate, the compound of Formula 9-6 was obtained in the same manner as in Example I-G1. At this time, the yield was 57%.

As a result of confirming the isocyanate content in the obtained isoidide di(3-cyclohexyl)acryloisocyanate through the method of measuring the potential difference of ISO 14896, it was confirmed to be at the level of 18.0+0.1 mass $\%_{NCO}$ (theoretical value=17.6 mass $\%_{NCO}$).

[Formula 9-6]

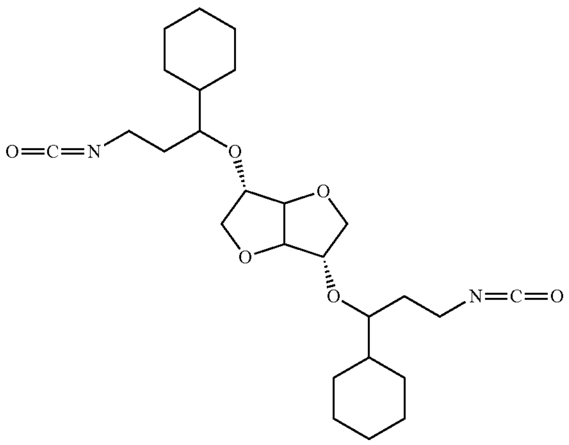

$^1H$ NMR (δ ppm; $CDCl_3$): 0.90-1.77 (26H, m), 2.59 (1H, m), 2.81 (1H, m), 3.24 (2H, t), 3.28 (2H, t), 3.47-3.55 (2H, m), 3.72-3.76 (2H, m), 4.00-4.04 (4H, m)

MS(m/e): 477

<Preparation of Polymer Comprising Dianhydrohexitol Diisocyanate Compound (Compound of Formula A)>

Examples I-J1 to I-J6: Preparation of Polyurethane Foam Using Compounds of Formulas 3-1 to 3-6

According to the components and content ratios shown in Table 1 below, a polyol, a surfactant, a catalyst and a blowing agent were mixed and sufficiently stirred at a stirring speed of 3,000 rpm for 1 to 3 minutes to prepare a polyol premix composition (first component).

To the prepared polyol premix composition (first component), the compounds of Formulas 3-1 to 3-6 prepared in Examples I-G1 to I-G6, respectively, were added as a polyisocyanate component (second component), and the mixtures were stirred for 7 seconds to 10 seconds at a stirring speed of 3,000 rpm to prepare a composition for forming a two-component polyurethane foam.

Subsequently, a polyethylene film was coated on a square box mold of 250 mm×250 mm in a square shape, and the prepared composition for forming a two-component polyurethane foam was poured thereon. At this time, the reaction initiation time (cream time), the maximum volume arrival time (rise time) and the gel time were measured and recorded using a second clock, and it was observed whether or not health bubbles were generated. As a result of checking the heat of curing reaction of the polyurethane foam with a bar thermometer, it was confirmed that it was 120° C. to 130° C. Thereafter, physical properties of the prepared polyurethane foam specimens were measured by the following evaluation method, and the results are shown in Table 1 below.

Comparative Example I-J1: Preparation of Polyurethane Foam Using Toluene Diisocyanate (TDI)

Except that toluene diisocyanate (TDI) was used as the polyisocyanate component (second component), a polyurethane foam specimen was prepared in the same manner as in Examples I-J1 to I-J6. Physical properties of the prepared polyurethane foam specimen were measured by the following evaluation method, and the results are shown in Table 1 below.

Comparative Example I-J2: Preparation of Polyurethane Foam Using 4,4-Diphenylmethylene Diisocyanate (MDI)

Except that 4,4'-diphenylmethylene diisocyanate (MDI) was used as the polyisocyanate component (second component), a polyurethane foam specimen was prepared in the same manner as in Examples I-J1 to 1-J6. Physical properties of the prepared polyurethane foam specimen were measured by the following evaluation method, and the results are shown in Table 1 below.

<Used Ingredients >

1) Polyol

PPG-3022: Trifunctional polyether polyol with an active hydrogen equivalent of 3,000 and a hydroxyl value of 54 to 58 mgKOH/g (PPG-3022 from Kumho Petrochemical)

2) Silicone surfactant

L-580K: Polyalkylene oxide methylsiloxane copolymer (Niax L-580K from Momentive)

3) Amine catalyst

-L-33: Triethylenediamine/dipropylene glycol solution at a concentration of 67% by weight (TEDA L-33 from Tosoh Corporation)

-A-1: Bis-(20dimethylaminoethyl)ether/propylene glycol solution at a concentration of 70% by weight (Niax Catalyst A-1 from Momentive)

4) Organometallic catalyst

DBTDL: organometallic catalyst (DBTDL from Sigma Aldrich)

5) Blowing agent

Water

6) Polyisocyanate component

① T-80: Toluene diisocyanate (TDI) (2,4-/2,6-isomer ratio=80:20) (Lupranate T-80 from BASF Korea)

② ME: 4,4-diphenylmethylene diisocyanate (MDI) (Lupranate ME product from BASF Korea)

③ SYC-ISO1.1: Diisocyanate compound of Formula 3-1 prepared in Example I-G1

④ SYC-ISO1.2: Diisocyanate compound of Formula 3-2 prepared in Example I-G2

⑤ SYC-ISO1.3: Diisocyanate compound of Formula 3-3 prepared in Example I-G3

⑥ SYC-ISO1.4: Diisocyanate compound of Formula 3-4 prepared in Example I-G4

⑦ SYC-ISO1.5: Diisocyanate compound of Formula 3-5 prepared in Example I-G5

⑧ SYC-ISO1.6: Diisocyanate compound of Formula 3-6 prepared in Example I-G6

Method of Measuring Physical Properties

A description of the physical properties described in Table 1 is as follows.

1) Cream time (seconds): shows the time taken from when the polyurethane foam stock solution is mixed until the stock solution starts to swell, and it is important to find a balance because this is the part that finds optimum reactivity. The fast and slow of the cream time is not important, but the short cream time is preferable because the longer cream time can result in irregular foam formation (or cell formation). However, too short a cream time may result in poor mixing, so a suitable cream time (e.g., 7 to 14 seconds) is required.

2) Rise time (seconds): shows the time taken from when polyurethane foam stock solution is mixed until the stock solution reaches to the maximum swelling of the foam. Rise time is the part that finds optimum reactivity, and it is important to balance between gelling and blowing, so it is hard to say good or bad just because of the fast and slow rise time. If the rise time is fast, the foam collapses (decayed before the foamed foam hardens, usually due to an incorrect stock solution ratio or insufficient mixing of raw materials), and if it is too slow, foaming may not be possible due to gelling (foaming of foam is stopped) during foaming. Therefore, a suitable rise time (e.g., 108 seconds to 124 seconds) is required. "Unmeasurable" of rise time means that the composition (stock solution) does not swell and no foam is formed.

3) Gel time: shows the time taken from the time when the polyurethane stock solution is mixed to the time when the stock solution has a gel strength that can withstand a light impact and has a stable spatial shape-specifically, the time when at least three or four urethane fibers come out when a foam in reaction is poked with wooden chopsticks.

4) Health bubbles: shows small bubbles that burst on the surface of the foam immediately after swelling to the maximum, and the presence of health bubbles means that foam foaming is correct.

O: Health bubbles exist x: Health bubbles do not exist

5) Foam state:

Good: The foam is blown (swollen), and it refers to a condition in which no collapse, cracks (cracking inside the foam due to external conditions during the formation of the foam or after the formation of the foam) or shrinkages (a phenomenon wherein the size of the foam is smaller than its original size by being cooled the gas trapped inside the foam) are apparent due to the gelling.

Bad: The foam does not form due to the bursting of cells while the foam is blowing.

6) Molding density: Measured according to ASTM D 1621.

7) Hardness: Measured according to KS M 6672.

8) Tensile strength: Measured according to KS M 6518.

9) Elongation: Measured according to KS M 6518.

TABLE 1

| | Categories | | Comparative Example I-J1 | Comparative Example I-J2 | Example I-J1 | Example I-J2 | Example I-J3 | Example I-J4 | Example I-J5 | Example I-J6 |
|---|---|---|---|---|---|---|---|---|---|---|
| Component (parts by weight) | Polyol | PPG-3022 | 100 | 100 | 100 | 100 | 100 | 100 | 100 | 100 |
| | Surfactant | L-580 | 1.2 | 1.2 | 1.2 | 1.2 | 1.2 | 1.2 | 1.2 | 1.2 |
| | Catalyst | A-1 | 0.13 | 0.13 | 0.11 | 0.20 | 0.18 | 0.19 | — | — |
| | | L-33 | 0.5 | 0.5 | 0.5 | 0.5 | 0.5 | 0.5 | 0.5 | 0.5 |
| | | DBTDL | 0.12 | 0.12 | 0.14 | 0.16 | 0.16 | 0.19 | 0.18 | 0.17 |
| | Blowing agent | Water | 0.9 | 0.9 | 0.9 | 0.9 | 0.9 | 0.9 | 0.9 | 0.9 |
| | Polyisocyanate | T-80 | 19.2 | — | — | — | — | — | — | — |
| | | ME | — | 27.5 | — | — | — | — | — | — |
| | | SYC-ISO1.1 | — | — | 34.3 | — | — | — | — | — |
| | | SYC-ISO1.2 | — | — | — | 37.4 | — | — | — | — |
| | | SYC-ISO1.3 | — | — | — | — | 37.4 | — | — | — |
| | | SYC-ISO1.4 | — | — | — | — | — | 51.1 | — | — |
| | | SYC-ISO1.5 | — | — | — | — | — | — | 48.9 | — |
| | | SYC-ISO1.6 | — | — | — | — | — | — | — | 52.4 |
| Properties | Isocyanate index | | 110 | 110 | 110 | 110 | 110 | 110 | 110 | 110 |
| | Cream time (sec) | | 11 | 10 | 12 | 13 | 12 | 14 | 14 | 13 |
| | Rise time (sec) | | 116 | 106 | 113 | 118 | 121 | 123 | 123 | 119 |
| | Gel time (sec) | | 89 | 80 | 93 | 94 | 92 | 100 | 96 | 94 |
| | Molding density ($kg/m^3$) | | 34.7 | 35.3 | 34.3 | 34.5 | 34.6 | 35.1 | 34.9 | 34.5 |
| | Hardness (25%, CLD)(kgf) | | 7.2 | 8.5 | 6.0 | 7.5 | 8.3 | 9.3 | 8.4 | 7.8 |
| | Health bubble | | ○ | ○ | ○ | ○ | ○ | ○ | ○ | ○ |
| | Tensile strength ($kg/cm^3$) | | 1.65 | 1.29 | 1.33 | 1.25 | 1.27 | 1.74 | 1.62 | 1.70 |
| | Elongation (%) | | 130 | 140 | 180 | 190 | 190 | 160 | 170 | 180 |
| | Foam state | | Good | Good | Good | Good | Good | Good | Good | Good |

As shown in Table 1, in the case of the polyurethane foams of Examples I-J1 to I-J6 prepared using the diisocyanate compound represented by Formula A according to the present invention as a polyisocyanate component, the molding density was about 35 $kg/m^3$, the tensile strength was 1.2 $kg/cm^3$ or more and the elongation was 160% or more, indicating excellent foam properties.

On the other hand, in the case of the polyurethane foams of Comparative Examples I-J1 and I-J2 prepared using TDI and MIDI, which are diisocyanate compounds commonly used as polyisocyanate components in the manufacture of polyurethane foams, the molding density was 35 $kg/m^3$ and the tensile strength was 1.2 $kg/cm^3$ or more, but the elongation was 130% to 140%, which was inferior to that of the polyurethane foams of Examples I-J1 to I-J6.

In particular, in the case of the polyurethane foams of Examples I-J4 and I-J6, the elongation was 160% or more, and the tensile strength was 1.70 $kg/cm^3$ or more, which was very excellent. In the case of the polyurethane foams of Examples I-J1 to I-J3, the tensile strength was 1.2 $kg/cm^3$ or more, and the elongation was 180% or more, which was very excellent.

In addition, when comparing Examples I-J4 to I-J6 and Comparative Example I-J1 having similar tensile strengths of 1.6 $kg/cm^3$ to 1.7 $kg/cm^3$, the elongation of polyurethane foams of Examples I-J4 to I-J6 was 160% to 180%, which showed a remarkably higher elongation than 130% of Comparative Example I-J1. From this, in terms of toughness in proportion to the elongation and tensile strength, it can be seen that the polyurethane foam of the Example exhibits higher toughness than the polyurethane foam of the Comparative Example.

In addition, even when comparing Examples I-J1 to I-J3 and Comparative Example I-J2 having a similar tensile strength of 1.2 $kg/cm^3$ to 1.3 $kg/cm^3$, the elongation of the polyurethane foam of Examples I-J1 to I-J3 was 180% to 190%, which was significantly higher than the 140% of Comparative Example I-J2. From this, it can also be seen that the polyurethane foam of the Example exhibits higher toughness than the polyurethane foam of the Comparative Example.

II. Preparation of Diisocyanate Compounds Having Anhydrosugar Alcohol Core and Alkylene Oxide Extensions (when m+n is 1 to 25 in Formula A)

<Preparation of Dianhydrohexitol-Alkylene Glycol>

Preparation Examples 1-1 to 1-4: Preparation of Isosorbide-Ethylene Glycol (m+n=3, 5, 10 or 25 in Formulas 10 and 11)

1 mole of isosorbide (146 g); 3, 5, 10 or 25 moles of ethylene oxide (132 g, 220 g, 441 g or 1,101 g); and sodium hydroxide (0.4 g) as a catalyst were placed in a reaction apparatus which is capable of pressurizing and has a column equipped with a nitrogen gas pipe and a cooling device, a stirrer, a thermometer and a heater, and gradually heated up. By reacting the mixture while maintaining at a temperature of 120° C. to 160°C for 2 to 4 hours, isosorbide-ethylene glycol (Preparation Example I-1: ethylene oxide 3 mole adduct), isosorbide-ethylene glycol (Preparation Example I-2: ethylene oxide 5 mole adduct), isosorbide-ethylene glycol (Preparation Example I-3: ethylene oxide 10 mole adduct) and isosorbide-ethylene glycol (Preparation Example I-4: ethylene oxide 25 mole adduct), which are in a form in which hydrogen of the hydroxy groups at both ends of isosorbide is substituted with 3 mole, 5 mole, 10 mole or 25 mole ethylene oxide groups, were prepared, respectively.

Preparation Examples 2-1 to 2-4: Preparation of Isosorbide-Propylene Glycol (m+n=3, 5, 10 or 25 in Formulas 10 and 11)

1 mole of isosorbide (146 g); 3, 5, 10 or 25 moles of propylene oxide (174 g, 290 g, 581 g or 1,452 g); and sodium hydroxide (0.4 g) as a catalyst were placed in a reaction apparatus which is capable of pressurizing and has a column equipped with a nitrogen gas pipe and a cooling device, a stirrer, a thermometer and a heater, and gradually heated up. By reacting the mixture while maintaining at a temperature of 120° C. to 160°C for 2 to 4 hours, isosorbide-propylene glycol (Preparation Example 2-1: propylene oxide 3 mole adduct), isosorbide-propylene glycol (Preparation Example 2-2: propylene oxide 5 mole adduct), isosorbide-propylene glycol (Preparation Example 2-3: propylene oxide 10 mole adduct) and isosorbide-propylene glycol (Preparation Example 2-4: propylene oxide 25 mole adduct), which are in a form in which hydrogen of the hydroxy groups at both ends of isosorbide is substituted with 3 mole, 5 mole, 10 mole or 25 mole propylene oxide groups, were prepared, respectively.

<Preparation of Dianhydrohexitol-Alkylene Glycol-Dinitrile Compound (compound of Formula A')>

Examples II-A1-1 to II-A1-4: Preparation of Diacrylonitrile of Isosorbide-Ethylene Glycol Each of isosorbide-ethylene glycol (Preparation Example I-1: ethylene oxide 3 mole adduct) 1 mol, isosorbide-ethylene glycol (Preparation Example I-2: ethylene oxide 5 mole adduct) 1 mol, isosorbide-ethylene glycol (Preparation Example I-3: ethylene oxide 10 mole adduct) 1 mol and isosorbide-ethylene glycol (Preparation Example I-4: ethylene oxide 25 mole adduct) 1 mol prepared in Preparation Examples 1-1 to 1-4 was put into a glass reactor with 1.5 g (0.01 mol) of 1,8-diazabicyclo[5.4.0]undec-7-ene and the internal temperature was raised to 70° C. to 75° C., and then 159 g (3 mol) of acrylonitrile was slowly added dropwise for about 4 hours so that the internal temperature did not exceed 80° C. After completion of the dropwise addition, the mixture was stirred for 3 hours while adjusting the internal temperature to 70° C. to 75° C., and then cooled to room temperature. The reaction mixture was diluted with 500 g of ethyl acetate, washed sequentially with 250 g of 1-normal aqueous hydrochloric acid solution, 250 g of 1-normal sodium hydroxide aqueous solution and 250 g of distilled water, and then concentrated under reduced pressure to obtain diacrylonitrile (Example II-A1-1, when m+n=3 and $R_1$, $R_2$ and $R_3$ are all hydrogen atoms in Formula 10) of isosorbide-ethylene glycol (Preparation Example I-1: ethylene oxide 3 mole adduct), diacrylonitrile (Example II-A1-2, when m+n=5 and $R_1$, $R_2$ and $R_5$ are all hydrogen atoms in Formula 10) of isosorbide-ethylene glycol (Preparation Example I-2: ethylene oxide 5 mole adduct), diacrylonitrile (Example II-A1-3, when m+n=10 and $R_1$, $R_2$ and $R_5$ are all hydrogen atoms in Formula 10) of isosorbide-ethylene glycol (Preparation Example I-3: ethylene oxide 10 mole adduct) and diacrylonitrile (Example II-A1-4, when m+n=25 and $R_1$, $R_2$ and $R_3$ are all hydrogen atoms in Formula 10) of isosorbide-ethylene glycol (Preparation Example I-4: ethylene oxide 25 mole adduct), respectively, in a yield of 85% to 95%.

Examples II-A2-1 to II-A2-4: Preparation of Diacrylonitrile of Isosorbide-Propylene Glycol Each of isosorbide-propylene glycol (Preparation Example 2-1: propylene oxide 3 mole adduct) 1 mol, isosorbide-propylene glycol (Preparation Example 2-2: propylene oxide 5 mole adduct) 1 mol, isosorbide-propylene glycol (Preparation Example 2-3: propylene oxide 10 mole adduct) 1 mol and isosorbide-propylene glycol (Preparation Example 2-4: propylene oxide 25 mole adduct) 1 mol prepared in Preparation Examples 2-1 to 2-4 was put into a glass reactor with 1.5 g (0.01 mol) of 1,8-diazabicyclo[5.4.0]undec-7-ene and the internal temperature was raised to 70° C. to 75° C., and then 159 g (3 mol) of acrylonitrile was slowly added dropwise for about 4 hours so that the internal temperature did not exceed 80° C. After completion of the dropwise addition, the mixture was stirred for 3 hours while adjusting the internal temperature to 70° C. to 75° C., and then cooled to room temperature. The reaction mixture was diluted with 500 g of ethyl acetate, washed sequentially with 250 g of 1-normal aqueous hydrochloric acid solution, 250 g of 1-normal sodium hydroxide aqueous solution and 250 g of distilled water, and then concentrated under reduced pressure to obtain diacrylonitrile (Example II-A2-1, when m+n=3, $R_1$ is methyl and both of $R_2$ and $R_3$ are hydrogen atoms in Formula 10) of isosorbide-propylene glycol (Preparation Example 2-1: propylene oxide 3 mole adduct), diacrylonitrile (Example II-A2-2, when m+n=5, $R_1$ is methyl and both of $R_2$ and $R_3$ are hydrogen atoms in Formula 10) of isosorbide-propylene glycol (Preparation Example 2-2: propylene oxide 5 mole adduct), diacrylonitrile (Example II-A2-3, when m+n=10, $R_1$ is methyl and both of $R_2$ and $R_3$ are hydrogen atoms in Formula 10) of isosorbide-propylene glycol (Preparation Example 2-3: propylene oxide 10 mole adduct) and diacrylonitrile (Example II-A2-4, when m+n=25, $R_1$ is methyl and both of $R_2$ and $R_3$ are hydrogen atoms in Formula 10) of isosorbide-propylene glycol (Preparation Example 2-4: propylene oxide 25 mole adduct), respectively, in a yield of 85% to 95%.

Examples II-A3-1 to II-A3-4: Preparation of Dicrotononitrile of Isosorbide-Ethylene Glycol Each of isosorbide-ethylene glycol (Preparation Example I-1: ethylene oxide 3 mole adduct) 1 mol, isosorbide-ethylene glycol (Preparation Example I-2: ethylene oxide 5 mole adduct) 1 mol, isosorbide-ethylene glycol (Preparation Example I-3: ethylene oxide 10 mole adduct) 1 mol and isosorbide-ethylene glycol (Preparation Example I-4: ethylene oxide 25 mole adduct) 1 mol prepared in Preparation Examples 1-1 to 1-4 was put into a glass reactor with 1.5 g (0.01 mol) of 1,8-diazabicyclo[5.4.0]undec-7-ene and the internal temperature was raised to 70° C. to 75° C., and then 201 g (3 mol) of crotononitrile was slowly added dropwise for about 4 hours so that the internal temperature did not exceed 80° C. After completion of the dropwise addition, the mixture was stirred for 3 hours while adjusting the internal temperature to 70° C. to 75° C., and then cooled to room temperature. The reaction mixture was diluted with 500 g of ethyl acetate, washed sequentially with 250 g of 1-normal aqueous hydrochloric acid solution, 250 g of 1-normal sodium hydroxide aqueous solution and 250 g of distilled water, and then concentrated under reduced pressure to obtain dicrotononitrile (Example II-A3-1, when m+n=3, $R_1$ and $R_3$ are all hydrogen atoms and $R_2$ is methyl in Formula 10) of isosorbide-ethylene glycol (Preparation Example I-1: ethylene oxide 3 mole adduct), dicrotononitrile (Example II-A3-2, when m+n=5, $R_1$ and $R_3$ are all hydrogen atoms and $R_2$ is methyl in Formula 10) of isosorbide-ethylene glycol (Preparation Example I-2: ethylene oxide 5 mole adduct), dicrotononitrile (Example II-A3-3, when m+n=10, $R_1$ and $R_3$ are all hydrogen atoms and $R_2$ is methyl in Formula 10) of isosorbide-ethylene glycol (Preparation Example I-3: ethylene oxide 10 mole adduct) and dicrotononitrile (Example II-A3-4, when m+n=25, $R_1$ and $R_3$ are all hydrogen atoms and $R_2$ is methyl in Formula 10) of isosorbide-ethylene glycol (Preparation Example I-4: ethylene oxide 25 mole adduct), respectively, in a yield of 85% to 95%.

Examples II-A4-1 to II-A4-4: Preparation of Dimethacrylonitrile of Isosorbide-Ethylene Glycol Each of isosorbide-ethylene glycol (Preparation Example I-1: ethylene oxide 3 mole adduct) 1 mol, isosorbide-ethylene glycol (Preparation Example I-2: ethylene oxide 5 mole adduct) 1 mol, isosorbide-ethylene glycol (Preparation Example I-3: ethylene oxide 10 mole adduct) 1 mol and isosorbide-ethylene glycol (Preparation Example I-4: ethylene oxide 25 mole adduct) 1 mol prepared in Preparation Examples 1-1 to 1-4 was put into a glass reactor with 1.5 g (0.01 mol) of 1,8-diazabicyclo[5.4.0]undec-7-ene and the internal temperature was raised to 70° C. to 75° C., and then 201 g (3 mol) of methacrylonitrile was slowly added dropwise for about 4 hours so that the internal temperature did not exceed 80° C. After completion of the dropwise addition, the mixture was stirred for 3 hours while adjusting the internal temperature to 70° C. to 75° C., and then cooled to room temperature. The reaction mixture was diluted with 500 g of ethyl acetate, washed sequentially with 250 g of 1-normal aqueous hydrochloric acid solution, 250 g of 1-normal sodium hydroxide aqueous solution and 250 g of distilled water, and then concentrated under reduced pressure to obtain dimethacrylonitrile (Example II-A4-1, when m+n=3, $R_1$ and $R_2$ are all hydrogen atoms and $R_3$ is methyl in Formula 10) of isosorbide-ethylene glycol (Preparation Example I-1: ethylene oxide 3 mole adduct), dimethacrylonitrile (Example II-A4-2, when m+n=5, $R_1$ and $R_2$ are all hydrogen atoms and $R_3$ is methyl in Formula 10) of isosorbide-ethylene glycol (Preparation Example I-2: ethylene oxide 5 mole adduct), dimethacrylonitrile (Example II-A4-3, when m+n=10, $R_1$ and $R_2$ are all hydrogen atoms and $R_3$ is methyl in Formula 10) of isosorbide-ethylene glycol (Preparation Example I-3: ethylene oxide 10 mole adduct) and dimethacrylonitrile (Example II-A4-4, when m+n=25, $R_1$ and $R_2$ are all hydrogen atoms and $R_3$ is methyl in Formula 10) of isosorbide-ethylene glycol (Preparation Example I-4: ethylene oxide 25 mole adduct), respectively, in a yield of 85% to 95%.

Examples II-A5-1 to II-A5-4: Preparation of Dicinnamonitrile of Isosorbide-Propylene Glycol Each of isosorbide-propylene glycol (Preparation Example 2-1: propylene oxide 3 mole adduct) 1 mol, isosorbide-propylene glycol (Preparation Example 2-2: propylene oxide 5 mole adduct) 1 mol, isosorbide-propylene glycol (Preparation Example 2-3: propylene oxide 10 mole adduct) 1 mol and isosorbide-propylene glycol (Preparation Example 2-4: propylene oxide 25 mole adduct) 1 mol prepared in Preparation Examples 2-1 to 2-4 was put into a glass reactor with 1.5 g (0.01 mol) of 1,8-diazabicyclo[5.4.0]undec-7-ene and the internal temperature was raised to 70° C. to 75° C., and then 387 g (3 mol) of cinnamonitrile was slowly added dropwise for about 4 hours so that the internal temperature did not exceed 80° C. After completion of the dropwise addition, the mixture was stirred for 5 hours while adjusting the internal temperature to 70° C. to 75° C., and then cooled to room temperature. The reaction mixture was diluted with 500 g of ethyl acetate, washed sequentially with 250 g of 1-normal aqueous hydrochloric acid solution, 250 g of 1-normal sodium hydroxide aqueous solution and 250 g of distilled water, and then concentrated under reduced pressure to obtain dicinnamonitrile (Example II-A5-1, when m+n=3, $R_1$ is methyl, $R_2$ is phenyl and $R_3$ is hydrogen atom in Formula 10) of isosorbide-propylene glycol (Preparation Example 2-1: propylene oxide 3 mole adduct), dicinnamonitrile (Example II-A5-2, when m+n=5, $R_1$ is methyl, $R_2$ is phenyl and $R_3$ is hydrogen atom in Formula 10) of isosorbide-propylene glycol (Preparation Example 2-2: propylene oxide 5 mole adduct), dicinnamonitrile (Example II-A5-3, when m+n=10, $R_1$ is methyl, $R_2$ is phenyl and $R_3$ is hydrogen atom in Formula 10) of isosorbide-propylene glycol (Preparation Example 2-3: propylene oxide 10 mole adduct) and dicinnamonitrile (Example II-A5-4, when m+n=25, $R_1$ is methyl, $R_2$ is phenyl and $R_3$ is hydrogen atom in Formula 10) of isosorbide-propylene glycol (Preparation Example 2-4: propylene oxide 25 mole adduct), respectively, in a yield of 80% to 90%.

Examples II-A6-1 to II-A6-4: Preparation of Di(3-Furyl)Acrylonitrile of Isosorbide-Ethylene Glycol Each of isosorbide-ethylene glycol (Preparation Example I-1: ethylene oxide 3 mole adduct) 1 mol, isosorbide-ethylene glycol (Preparation Example I-2: ethylene oxide 5 mole adduct) 1 mol, isosorbide-ethylene glycol (Preparation Example I-3: ethylene oxide 10 mole adduct) 1 mol and isosorbide-ethylene glycol (Preparation Example I-4: ethylene oxide 25 mole adduct) 1 mol prepared in Preparation Examples 1-1 to 1-4 was put into a glass reactor with 1.5 g (0.01 mol) of 1,8-diazabicyclo[5.4.0]undec-7-ene and the internal temperature was raised to 70° C. to 75° C., and then 357 g (3 mol) of 3-(furan-2-yl)prop-2-enenitrile was slowly added dropwise for about 4 hours so that the internal temperature did not exceed 80° C. After completion of the dropwise addition, the mixture was stirred for 12 hours while adjusting the internal temperature to 70° C. to 75° C., and then cooled to room temperature. The reaction mixture was diluted with 500 g of ethyl acetate, washed sequentially with 250 g of 1-normal aqueous hydrochloric acid solution, 250 g of 1-normal sodium hydroxide aqueous solution and 250 g of distilled water, and then concentrated under reduced pressure to obtain di(3-furyl)acrylonitrile (Example II-A6-1, when m+n=3, $R_1$ and $R_3$ are all hydrogen atoms and $R_2$ is furyl in Formula 10) of isosorbide-ethylene glycol (Preparation Example I-1: ethylene oxide 3 mole adduct), di(3-furyl)acrylonitrile (Example II-A6-2, when m+n=5, $R_1$ and $R_3$ are all hydrogen atoms and $R_2$ is furyl in Formula 10) of isosorbide-ethylene glycol (Preparation Example I-2: ethylene oxide 5 mole adduct), di(3-furyl)acrylonitrile (Example II-A6-3, when m+n=10, $R_1$ and $R_3$ are all hydrogen atoms and $R_2$ is furyl in Formula 10) of isosorbide-ethylene glycol (Preparation Example I-3: ethylene oxide 10 mole adduct) and di(3-furyl)acrylonitrile (Example II-A6-4, when m+n=25, $R_1$ and $R_3$ are all hydrogen atoms and $R_2$ is furyl in Formula 10) of isosorbide-ethylene glycol (Preparation Example I-4: ethylene oxide 25 mole adduct), respectively, in a yield of 80% to 90%.

Examples II-A7-1 to II-A7-4: Preparation of Di(3-Cyclohexyl)Acrylonitrile of Isosorbide-Propylene Glycol Each of isosorbide-propylene glycol (Preparation Example 2-1: propylene oxide 3 mole adduct) 1 mol, isosorbide-propylene glycol (Preparation Example 2-2: propylene oxide 5 mole adduct) 1 mol, isosorbide-propylene glycol (Preparation Example 2-3: propylene oxide 10 mole adduct) 1 mol and isosorbide-propylene glycol (Preparation Example 2-4: propylene oxide 25 mole adduct) 1 mol prepared in Preparation Examples 2-1 to 2-4 was put into a glass reactor with 1.5 g (0.01 mol) of 1,8-diazabicyclo [5.4.0]undec-7-ene and the internal temperature was raised to 70° C. to 75° C., and then 405 g (3 mol) of cyclohexane acrylonitrile was slowly added dropwise for about 4 hours so that the internal temperature did not exceed 80° C. After completion of the dropwise addition, the mixture was stirred for 6 hours while adjusting the internal temperature to 70° C. to 75° C., and then cooled to room temperature. The reaction mixture was diluted with 500 g of ethyl acetate, washed sequentially with 250 g of 1-normal aqueous hydrochloric acid solution, 250 g of 1-normal sodium hydroxide aqueous solution and 250 g of distilled water, and then concentrated under reduced pressure to obtain di(3-cyclohexyl)acrylonitrile (Example II-A7-1, when m+n=3, $R_1$ is methyl, $R_2$ is cyclohexyl and $R_3$ is hydrogen atom in Formula 10) of isosorbide-propylene glycol (Preparation Example 2-1: propylene oxide 3 mole adduct), di(3-cyclohexyl)acrylonitrile (Example II-A7-2, when m+n=5, $R_1$ is methyl, $R_2$ is cyclohexyl and $R_3$ is hydrogen atom in Formula 10) of isosorbide-propylene glycol (Preparation Example 2-2: propylene oxide 5 mole adduct), di(3-cyclohexyl)acrylonitrile (Example II-A7-3, when m+n=10, $R_1$ is methyl, $R_2$ is cyclohexyl and $R_3$ is hydrogen atom in Formula 10) of isosorbide-propylene glycol (Preparation Example 2-3: propylene oxide 10 mole adduct) and di(3-cyclohexyl)acrylonitrile (Example II-A7-4, when m+n=25, $R_1$ is methyl, $R_2$ is cyclohexyl and $R_3$ is hydrogen atom in Formula 10) of isosorbide-propylene glycol (Preparation Example 2-4: propylene oxide 25 mole adduct), respectively, in a yield of 80% to 90%.

<Preparation of Dianhydrohexitol-Alkylene Glycol-Diamine Compound (Compound of Formula A")>

Examples II-B1-1 to II-B1-4: Preparation of Diacryloamine of Isosorbide-Ethylene Glycol 1,000 g of each of diacrylonitrile (Example II-A1-1, m+n=3, $R_1$, $R_2$ and $R_3$ are all hydrogen atoms in Formula 10) of the isosorbide-ethylene glycol (Preparation Example I-1: ethylene oxide 3 mole adduct), diacrylonitrile (Example II-A1-2, m+n=5, $R_1$, $R_2$ and $R_3$ are all hydrogen atoms in Formula 10) of the isosorbide-ethylene glycol (Preparation Example I-2: ethylene oxide 5 mole adduct), diacrylonitrile (Example II-A1-3, m+n=10, $R_1$, $R_2$ and $R_3$ are all hydrogen atoms in Formula 10) of the isosorbide-ethylene glycol (Preparation Example I-3: ethylene oxide 10 mole adduct) and diacrylonitrile (Example II-A1-4, m+n=25, $R_1$, $R_2$ and $R_3$ are all hydrogen atoms in Formula 10) of the isosorbide-ethylene glycol (Preparation Example I-4: ethylene oxide 25 mole adduct) prepared in Examples II-A1-1 to II-A1-4 was put into a high-pressure reactor with 2,000 g of purified water, 50 g of Raney nickel and 300 g of ammonia water and sealed, and then hydrogen was added at 10 bar. While maintaining the hydrogen pressure, the internal temperature was heated to 130° C. and stirred for 4 hours. After the reaction was completed, the catalyst was recovered through filtration, and the filtrate was concentrated to obtain diacryloamine (Example II-B1-1, m+n=3, $R_1$, $R_2$ and $R_3$ are all hydrogen atoms in Formula 11) of isosorbide-ethylene glycol (Preparation Example I-1: ethylene oxide 3 mole adduct), diacryloamine (Example II-B1-2, m+n=5, $R_1$, $R_2$ and $R_3$ are all hydrogen atoms in Formula 11) of isosorbide-ethylene glycol (Preparation Example I-2: ethylene oxide 5 mole adduct), diacryloamine (Example II-B1-3, m+n=10, $R_1$, $R_2$ and $R_5$ are all hydrogen atoms in Formula 11) of isosorbide-ethylene glycol (Preparation Example I-3: ethylene oxide 10 mole adduct) and diacryloamine (Example II-B1-4, m+n=25, $R_1$, $R_2$ and $R_3$ are all hydrogen atoms in Formula 11) of isosorbide-ethylene glycol (Preparation Example I-4: ethylene oxide 25 mole adduct), respectively, in a yield of 75% to 85%.

Examples II-B2-1 to II-B2-4: Preparation of Diacryloamine of Isosorbide-Propylene Glycol 1,000 g of each of diacrylonitrile (Example II-A2-1, m+n=3, $R_1$ is methyl, and $R_2$ and $R_3$ are all hydrogen atoms in Formula 10) of the isosorbide-propylene glycol (Preparation Example 2-1: propylene oxide 3 mole adduct), diacrylonitrile (Example II-A2-2, m+n=5, $R_1$ is methyl, and $R_2$ and $R_3$ are all hydrogen atoms in Formula 10) of the isosorbide-propylene glycol (Preparation Example 2-2: propylene oxide 5 mole adduct), diacrylonitrile (Example II-A2-3, m+n=10, $R_1$ is methyl, and $R_2$ and $R_3$ are all hydrogen atoms in Formula 10) of the isosorbide-propylene glycol (Preparation Example 2-3: propylene oxide 10 mole adduct) and diacrylonitrile (Example II-A2-4, m+n=25, $R_1$ is methyl, and $R_2$ and $R_3$ are all hydrogen atoms in Formula 10) of the isosorbide-propylene glycol (Preparation Example 2-4: propylene oxide 25 mole adduct) prepared in Examples II-A2-1 to II-A2-4 was put into a high-pressure reactor with 2,000 g of purified water, 50 g of Raney nickel and 300 g of ammonia water and sealed, and then hydrogen was added at 10 bar. While maintaining the hydrogen pressure, the internal temperature was heated to 130° C. and stirred for 4 hours. After the reaction was completed, the catalyst was recovered through filtration, and the filtrate was concentrated to obtain diacryloamine (Example II-B2-1, m+n=3, $R_1$ is methyl, and $R_2$ and $R_3$ are all hydrogen atoms in Formula 11) of isosorbide-propylene glycol (Preparation Example 2-1: propylene oxide 3 mole adduct), diacryloamine (Example II-B2-2, m+n=5, $R_1$ is methyl, and $R_2$ and $R_3$ are all hydrogen atoms in Formula 11) of isosorbide-propylene glycol (Preparation Example 2-2: propylene oxide 5 mole adduct), diacryloamine (Example II-B2-3, m+n=10, $R_1$ is methyl, and $R_2$ and $R_3$ are all hydrogen atoms in Formula 11) of isosorbide-propylene glycol (Preparation Example 2-3: propylene oxide 10 mole adduct) and diacryloamine (Example II-B2-4, m+n=25, $R_1$ is methyl, and $R_2$ and $R_3$ are all hydrogen atoms in Formula 11) of isosorbide-propylene glycol (Preparation Example 2-4: propylene oxide 25 mole adduct), respectively, in a yield of 75% to 85%.

Examples II-B3-1 to II-B3-4: Preparation of Dicrotonoamine of Isosorbide-Ethylene Glycol 1,000 g of each of dicrotononitrile (Example II-A3-1, m+n=3, $R_1$ and $R_3$ are all hydrogen atoms, and $R_2$ is methyl in Formula 10) of the isosorbide-ethylene glycol (Preparation Example I-1: ethylene oxide 3 mole adduct), dicrotononitrile (Example II-A3-2, m+n=5, $R_1$ and $R_3$ are all hydrogen atoms, and $R_2$ is methyl in Formula 10) of the isosorbide-ethylene glycol (Preparation Example I-2: ethylene oxide 5 mole adduct), dicrotononitrile (Example II-A3-3, m+n=10, $R_1$ and $R_3$ are all hydrogen atoms, and $R_2$ is methyl in Formula 10) of the isosorbide-ethylene glycol (Preparation Example I-3: ethylene oxide 10 mole adduct) and dicrotononitrile (Example II-A3-4, m+n=25, $R_1$ and $R_3$ are all hydrogen atoms, and $R_2$ is methyl in Formula 10) of the isosorbide-ethylene glycol (Preparation Example I-4: ethylene oxide 25 mole adduct) prepared in Examples II-A3-1 to II-A3-4 was put into a high-pressure reactor with 2,000 g of purified water, 50 g of Raney nickel and 300 g of ammonia water and sealed, and then hydrogen was added at 10 bar. While maintaining the hydrogen pressure, the internal temperature was heated to 130° C. and stirred for 4 hours. After the reaction was completed, the catalyst was recovered through filtration, and the filtrate was concentrated to obtain dicrotonoamine (Example II-B3-1, m+n=3, $R_1$ and $R_3$ are all hydrogen atoms, and $R_2$ is methyl in Formula 11) of isosorbide-ethylene glycol (Preparation Example 1-1: ethylene oxide 3 mole adduct), dicrotonoamine (Example II-B3-2, m+n=5, $R_1$ and $R_3$ are all hydrogen atoms, and $R_2$ is methyl in Formula 11) of isosorbide-ethylene glycol (Preparation Example I-2: ethylene oxide 5 mole adduct), dicrotonoamine (Example II-B3-3, m+n=10, $R_1$ and $R_3$ are all hydrogen atoms, and $R_2$ is methyl in Formula 11) of isosorbide-ethylene glycol (Preparation Example I-3: ethylene oxide 10 mole adduct) and dicrotonoamine (Example II-B3-4, m+n=25, $R_1$ and $R_3$ are all hydrogen atoms, and $R_2$ is methyl in Formula 11) of isosorbide-ethylene glycol (Preparation Example I-4: ethylene oxide 25 mole adduct), respectively, in a yield of 75% to 85%.

Examples II-B4-1 to II-B4-4: Preparation of Dimethacryloamine of Isosorbide-Ethylene Glycol 1,000 g of each of dimethacrylonitrile (Example II-A4-1, m+n=3, $R_1$ and $R_2$ are all hydrogen atoms, and $R_3$ is methyl in Formula 10) of the isosorbide-ethylene glycol (Preparation Example I-1: ethylene oxide 3 mole adduct), dimethacrylonitrile (Example II-A4-2, m+n=5, $R_1$ and $R_2$ are all hydrogen atoms, and $R_3$ is methyl in Formula 10) of the isosorbide-ethylene glycol (Preparation Example I-2: ethylene oxide 5 mole adduct), dimethacrylonitrile (Example II-A4-3, m+n=10, $R_1$ and $R_2$ are all hydrogen atoms, and $R_3$ is methyl in Formula 10) of the isosorbide-ethylene glycol (Preparation Example I-3: ethylene oxide 10 mole adduct) and dimethacrylonitrile (Example II-A4-4, m+n=25, $R_1$ and $R_2$ are all hydrogen atoms, and $R_3$ is methyl in Formula 10) of the isosorbide-ethylene glycol (Preparation Example I-4: ethylene oxide 25 mole adduct) prepared in Examples II-A4-1 to II-A4-4 was put into a high-pressure reactor with 2,000 g of purified water, 50 g of Raney nickel and 300 g of ammonia water and sealed, and then hydrogen was added at 10 bar. While maintaining the hydrogen pressure, the internal temperature was heated to 130° C. and stirred for 4 hours. After the reaction was completed, the catalyst was recovered through filtration, and the filtrate was concentrated to obtain dimethacryloamine (Example II-B4-1, m+n=3, $R_1$ and $R_2$ are all hydrogen atoms, and $R_3$ is methyl in Formula 11) of isosorbide-ethylene glycol (Preparation Example I-1: ethylene oxide 3 mole adduct), dimethacryloamine (Example II-B4-2, m+n=5, $R_1$ and $R_2$ are all hydrogen atoms, and $R_3$ is methyl in Formula 11) of isosorbide-ethylene glycol (Preparation Example I-2: ethylene oxide 5 mole adduct), dimethacryloamine (Example II-B4-3, m+n=10, $R_1$ and $R_2$ are all hydrogen atoms, and $R_3$ is methyl in Formula 11) of isosorbide-ethylene glycol (Preparation Example I-3: ethylene oxide 10 mole adduct) and dimethacryloamine (Example II-B4-4, m+n=25, $R_1$ and $R_2$ are all hydrogen atoms, and $R_3$ is methyl in Formula 11) of isosorbide-ethylene glycol (Preparation Example I-4: ethylene oxide 25 mole adduct), respectively, in a yield of 75% to 85%.

Examples II-B5-1 to II-B5-4: Preparation of Dicinnamoamine of Isosorbide-Propylene Glycol 1,000 g of each of dicinnamonitrile (Example II-A5-1, m+n=3, $R_1$ is methyl, $R_2$ is phenyl and $R_3$ is hydrogen atom in Formula 10) of the isosorbide-propylene glycol (Preparation Example 2-1: propylene oxide 3 mole adduct), dicinnamonitrile (Example II-A5-2, m+n=5, $R_1$ is methyl, $R_2$ is phenyl, and $R_3$ is hydrogen atom in Formula 10) of the isosorbide-propylene glycol (Preparation Example 2-2: propylene oxide 5 mole adduct), dicinnamonitrile (Example II-A5-3, m+n=10, $R_1$ is methyl, $R_2$ is phenyl, and $R_3$ is hydrogen atom in Formula 10) of the isosorbide-propylene glycol (Preparation Example 2-3: propylene oxide 10 mole adduct), dicinnamonitrile (Example II-A5-4, m+n=25, $R_1$ is methyl, $R_2$ is phenyl, and $R_3$ is hydrogen atom in Formula 10) of the isosorbide-propylene glycol (Preparation Example 2-4: propylene oxide 25 mole adduct) prepared in Examples II-A5-1 to II-A5-4 was put into a high-pressure reactor with 2,000 g of purified water, 50 g of Raney nickel and 300 g of ammonia water and sealed, and then hydrogen was added at 10 bar. While maintaining the hydrogen pressure, the internal temperature was heated to 130° C. and stirred for 4 hours. After the reaction was completed, the catalyst was recovered through filtration, and the filtrate was concentrated to obtain dicinnamoamine (Example II-B5-1, m+n=3, $R_1$ is methyl, $R_2$ is phenyl, and $R_3$ is hydrogen atom in Formula 11) of isosorbide-propylene glycol (Preparation Example 2-1: propylene oxide 3 mole adduct), dicinnamoamine (Example II-B5-2, m+n=5, $R_1$ is methyl, $R_2$ is phenyl, and $R_3$ is hydrogen atom in Formula 11) of isosorbide-propylene glycol (Preparation Example 2-2: propylene oxide 5 mole adduct), dicinnamoamine (Example II-B5-3, m+n=10, $R_1$ is methyl, $R_2$ is phenyl, and $R_3$ is hydrogen atom in Formula 11) of isosorbide-propylene glycol (Preparation Example 2-3: propylene oxide 10 mole adduct) and dicinnamoamine (Example II-B5-4, m+n=25, $R_1$ is methyl, $R_2$ is phenyl, and $R_3$ is hydrogen atom in Formula 11) of isosorbide-propylene glycol (Preparation Example 2-4: propylene oxide 25 mole adduct), respectively, in a yield of 70% to 80%.

Examples II-B6-1 to II-B6-4: Preparation of Di(3-Furyl)Acryloamine of Isosorbide-Ethylene Glycol 1,000 g of each of di(3-furyl)acrylonitrile (Example II-A6-1, m+n=3, $R_1$ and $R_3$ are all hydrogen atoms, and $R_2$ is furyl in Formula 10) of the isosorbide-ethylene glycol (Preparation Example I-1: ethylene oxide 3 mole adduct), di(3-furyl)acrylonitrile (Example II-A6-2, m+n=5, $R_1$ and $R_3$ are all hydrogen atoms, and $R_2$ is furyl in Formula 10) of the isosorbide-ethylene glycol (Preparation Example I-2: ethylene oxide 5 mole adduct), di(3-furyl)acrylonitrile (Example II-A6-3, m+n=10, $R_1$ and $R_3$ are all hydrogen atoms, and $R_2$ is furyl in Formula 10) of the isosorbide-ethylene glycol (Preparation Example I-3: ethylene oxide 10 mole adduct) and di(3-furyl)acrylonitrile (Example II-A6-4, m+n=25, $R_1$ and $R_3$ are all hydrogen atoms, and $R_2$ is furyl in Formula 10) of the isosorbide-ethylene glycol (Preparation Example I-4: ethylene oxide 25 mole adduct) prepared in Examples II-A6-1 to II-A6-4 was put into a high-pressure reactor with 2,000 g of purified water, 50 g of Raney nickel and 300 g of ammonia water and sealed, and then hydrogen was added at 10 bar. While maintaining the hydrogen pressure, the internal temperature was heated to 130° C. and stirred for 4 hours. After the reaction was completed, the catalyst was recovered through filtration, and the filtrate was concentrated to obtain di(3-furyl)acryloamine (Example II-B6-1, m+n=3, $R_1$ and $R_3$ are all hydrogen atoms, and $R_2$ is furyl in Formula 11) of isosorbide-ethylene glycol (Preparation Example I-1: ethylene oxide 3 mole adduct), di(3-furyl)acryloamine (Example II-B6-2, m+n=5, $R_1$ and $R_3$ are all hydrogen atoms, and $R_2$ is furyl in Formula 11) of isosorbide-ethylene glycol (Preparation Example I-2: ethylene oxide 5 mole adduct), di(3-furyl)acryloamine (Example II-B6-3, m+n=10, $R_1$ and $R_3$ are all hydrogen atoms, and $R_2$ is furyl in Formula 11) of isosorbide-ethylene glycol (Preparation Example I-3: ethylene oxide 10 mole adduct) and di(3-furyl)acryloamine (Example II-B6-4, m+n=25, $R_1$ and $R_3$ are all hydrogen atoms, and $R_2$ is furyl in Formula 11) of isosorbide-ethylene glycol (Preparation Example I-4: ethylene oxide 25 mole adduct), respectively, in a yield of 70% to 80%.

Examples II-B7-1 to II-B7-4: Preparation of Di(3-Cyclohexyl)Acryloamine of Isosorbide-Propylene Glycol 1,000 g of each of di(3-cyclohexyl)acrylonitrile (Example II-A7-1, m+n=3, $R_1$ is methyl, $R_2$ is cyclohexyl, and $R_3$ is hydrogen atom in Formula 10) of the isosorbide-propylene glycol (Preparation Example 2-1: propylene oxide 3 mole adduct), di(3-cyclohexyl)acrylonitrile (Example II-A7-2, m+n=5, $R_1$ is methyl, $R_2$ is cyclohexyl, and $R_3$ is hydrogen atom in Formula 10) of the isosorbide-propylene glycol (Preparation Example 2-2: propylene oxide 5 mole adduct), di(3-cyclohexyl)acrylonitrile (Example II-A7-3, m+n=10, $R_1$ is methyl, $R_2$ is cyclohexyl, and $R_3$ is hydrogen atom in Formula 10) of the isosorbide-propylene glycol (Preparation Example 2-3: propylene oxide 10 mole adduct) and di(3-cyclohexyl)acrylonitrile (Example II-A7-4, m+n=25, $R_1$ is methyl, $R_2$ is cyclohexyl, and $R_3$ is hydrogen atom in Formula 10) of the isosorbide-propylene glycol (Preparation Example 2-4: propylene oxide 25 mole adduct) prepared in Examples II-A7-1 to II-A7-4 was put into a high-pressure reactor with 2,000 g of purified water, 50 g of Raney nickel and 300 g of ammonia water and sealed, and then hydrogen was added at 10 bar. While maintaining the hydrogen pressure, the internal temperature was heated to 130° C. and stirred for 4 hours. After the reaction was completed, the catalyst was recovered through filtration, and the filtrate was concentrated to obtain di(3-cyclohexyl)acryloamine (Example II-B7-1, m+n=3, $R_1$ is methyl, $R_2$ is cyclohexyl, and $R_3$ is hydrogen atom in Formula 11) of isosorbide-propylene glycol (Preparation Example 2-1: propylene oxide 3 mole adduct), di(3-cyclohexyl)acryloamine (Example II-B7-2, m+n=5, $R_1$ is methyl, $R_2$ is cyclohexyl, and $R_3$ is hydrogen atom in Formula 11) of isosorbide-propylene glycol (Preparation Example 2-2: propylene oxide 5 mole adduct), di(3-cyclohexyl)acryloamine (Example II-B7-3, m+n=10, $R_1$ is methyl, $R_2$ is cyclohexyl, and $R_3$ is hydrogen atom in Formula 11) of isosorbide-propylene glycol (Preparation Example 2-3: propylene oxide 10 mole adduct) and di(3-cyclohexyl)acryloamine (Example II-B7-4, m+n=25, $R_1$ is methyl, $R_2$ is cyclohexyl, and $R_3$ is hydrogen atom in Formula 11) of isosorbide-propylene glycol (Preparation Example 2-4: propylene oxide 25 mole adduct), respectively, in a yield of 75% to 85%.

<Preparation of Isosorbide-Alkylene Glycol-Diisocyanate Compound (Compound of Formula A)>

Examples II-C1-1 to II-C1-4: Preparation of Dipropylisocyanate of Isosorbide-Ethylene Glycol (Using Carbonate)

After adding 300 ml of methylene chloride to a 4-neck reactor equipped with a condenser, an internal thermometer and a nitrogen injection line, 0.05 molar equivalent of 4-dimethylaminopyridine (DMAP) and 3.0 molar equivalent of di-tert-butyldicarbonate (DBDC) were added and dissolved in methylene chloride. Subsequently, the temperature inside the reactor was maintained at 0° C. to 5° C. using an ice bath under a nitrogen atmosphere. A solution prepared by dissolving 1.0 molar equivalent of each of diacryloamine (Example II-B1-1, m+n=3, $R_1$, $R_2$ and $R_3$ are all hydrogen atoms in Formula 11) of isosorbide-ethylene glycol (Preparation Example I-1: ethylene oxide 3 mole adduct), diacryloamine (Example II-B1-2, m+n=5, $R_1$, $R_2$ and $R_3$ are all hydrogen atoms in Formula 11) of isosorbide-ethylene glycol (Preparation Example I-2: ethylene oxide 5 mole adduct), diacryloamine (Example II-B1-3, m+n=10, $R_1$, $R_2$ and $R_5$ are all hydrogen atoms in Formula 11) of isosorbide-ethylene glycol (Preparation Example I-3: ethylene oxide 10 mole adduct) and diacryloamine (Example II-B1-4, m+n=25, $R_1$, $R_2$ and $R_3$ are all hydrogen atoms in Formula 11) of isosorbide-ethylene glycol (Preparation Example I-4: ethylene oxide 25 mole adduct) prepared in Examples II-B1-1 to II-B1-4 in 200 ml of methylene chloride was added dropwise to the reactor, at which time the temperature inside the reactor was kept at 0° C. to 5° C. After the dropwise addition was completed, the temperature inside the reactor was raised to 25° C., and the reaction was performed for 3 hours.

Methylene chloride was removed from the obtained reaction products using a concentrator, and the reaction products were extracted using hexane and tertiary distilled water. After removing moisture from the extract using magnesium sulfate, hexane was removed from the extract using a concentrator to obtain dipropylisocyanate (Example II-C1-1, m+n=3, $R_1$, $R_2$ and $R_3$ are all hydrogen atoms in Formula 12) of isosorbide-ethylene glycol (Preparation Example I-1: ethylene oxide 3 mole adduct), dipropylisocyanate (Example II-$C_1$-2, m+n=5, $R_1$, $R_2$ and $R_5$ are all hydrogen atoms in Formula 12) of isosorbide-ethylene glycol (Preparation Example I-2: ethylene oxide 5 mole adduct), dipropylisocyanate (Example II-C1-3, m+n=10, $R_1$, $R_2$ and $R_3$ are all hydrogen atoms in Formula 12) of isosorbide-ethylene glycol (Preparation Example I-3: ethylene oxide 10 mole adduct) and dipropylisocyanate (Example II-C1-4, m+n=25, $R_1$, $R_2$ and $R_5$ are all hydrogen atoms in Formula 12) of isosorbide-ethylene glycol (Preparation Example I-4: ethylene oxide 25 mole adduct), respectively, in a yield of 80% to 90%.

As a result of confirming the isocyanate content in the dipropylisocyanate of isosorbide-ethylene glycol obtained in Examples II-C1-1 to II-C1-4 through the method of measuring the potential difference of ISO 14896, it was confirmed that Example II-C1-1 is at the level of 19.1+0.2 mass $\%_{NCO}$ (theoretical value=18.9 mass $\%_{NCO}$), Example II-C1-2 is at the level of 16.0+0.2 mass $\%_{NCO}$ (theoretical value=15.8 mass $\%_{NCO}$), Example II-C1-3 is at the level of 11.0+0.2 mass $\%_{NCO}$ (theoretical value=11.1 mass $\%_{NCO}$) and Example II-C1-4 is at the level of 6.1+0.2 mass $\%_{NCO}$ (theoretical value=5.9 mass $\%_{NCO}$). The mass $\%_{NCO}$, which is a unit of the isocyanate content, refers to the mass % of the NCO group present in the sample, dipropylisocyanate of isosorbide-ethylene glycol.

Examples II-C2-1 to II-C2-4: Preparation of Dipropylisocyanate of Isosorbide-Propylene Glycol After adding 300 ml of methylene chloride to a 4-neck reactor equipped with a condenser, an internal thermometer and a nitrogen injection line, 0.05 molar equivalent of 4-dimethylaminopyridine (DMAP) and 3.0 molar equivalent of di-tert-butyldicarbonate (DBDC) were added and dissolved in methylene chloride. Subsequently, the temperature inside the reactor was maintained at 0° C. to 5° C. using an ice bath under a nitrogen atmosphere. A solution prepared by dissolving 1.0 molar equivalent of each of diacryloamine (Example II-B2-1, m+n=3, $R_1$ is methyl, and $R_2$ and $R_3$ are all hydrogen atoms in Formula 11) of isosorbide-propylene glycol (Preparation Example 2-1: propylene oxide 3 mole adduct), diacryloamine (Example II-B2-2, m+n=5, $R_1$ is methyl, and $R_2$ and $R_3$ are all hydrogen atoms in Formula 11) of isosorbide-propylene glycol (Preparation Example 2-2: propylene oxide 5 mole adduct), diacryloamine (Example II-B2-3, m+n=10, $R_1$ is methyl, and $R_2$ and $R_3$ are all hydrogen atoms in Formula 11) of isosorbide-propylene glycol (Preparation Example 2-3: propylene oxide 10 mole adduct) and diacryloamine (Example II-B2-4, m+n=25, $R_1$ is methyl, and $R_2$ and $R_3$ are all hydrogen atoms in Formula 11) of isosorbide-propylene glycol (Preparation Example 2-4: propylene oxide 25 mole adduct) prepared in Examples II-B2-1 to II-B2-4 in 200 ml of methylene chloride was added dropwise to the reactor, at which time the temperature inside the reactor was kept at 0° C. to 5° C. After the dropwise addition was completed, the temperature inside the reactor was raised to 25° C., and the reaction was performed for 3 hours.

Methylene chloride was removed from the obtained reaction products using a concentrator, and the reaction products were extracted using hexane and tertiary distilled water. After removing moisture from the extract using magnesium sulfate, hexane was removed from the extract using a concentrator to obtain dipropylisocyanate (Example II-C2-1, m+n=3, $R_1$ is methyl, and $R_2$ and $R_3$ are all hydrogen atoms in Formula 12) of isosorbide-propylene glycol (Preparation Example 2-1: propylene oxide 3 mole adduct), dipropylisocyanate (Example II-C2-2, m+n=5, $R_1$ is methyl, and $R_2$ and $R_5$ are all hydrogen atoms in Formula 12) of isosorbide-propylene glycol (Preparation Example 2-2: propylene oxide 5 mole adduct), dipropylisocyanate (Example II-C2-3, m+n=10, $R_1$ is methyl, and $R_2$ and $R_3$ are all hydrogen atoms in Formula 12) of isosorbide-propylene glycol (Preparation Example 2-3: propylene oxide 10 mole adduct) and dipropylisocyanate (Example II-C2-4, m+n=25, $R_1$ is methyl, and $R_2$ and $R_3$ are all hydrogen atoms in Formula 12) of isosorbide-propylene glycol (Preparation Example 2-4: propylene oxide 25 mole adduct), respectively, in a yield of 70% to 80%.

As a result of confirming the isocyanate content in the dipropylisocyanate of isosorbide-propylene glycol obtained in Examples II-C2-1 to II-C2-4 through the method of measuring the potential difference of ISO 14896, it was confirmed that Example II-C2-1 is at the level of 17.1+0.3 mass $\%_{NCO}$ (theoretical value=17.3 mass $\%_{NCO}$), Example II-C2-2 is at the level of 13.9+0.1 mass $\%_{NCO}$ (theoretical value=13.9 mass $\%_{NCO}$), Example II-C2-3 is at the level of 9.6+0.2 mass $\%_{NCO}$ (theoretical value=9.4 mass $\%_{NCO}$) and Example II-C2-4 is at the level of 4.8+0.1 mass $\%_{NCO}$ (theoretical value=4.8 mass $\%_{NCO}$). The mass $\%_{NCO}$, which is a unit of the isocyanate content, refers to the mass % of the NCO group present in the sample, dipropylisocyanate of isosorbide-propylene glycol.

Examples II-C3-1 to II-C3-4: Preparation of Dicrotonoisocyanate of Isosorbide-Ethylene Glycol After adding 300 ml of methylene chloride to a 4-neck reactor equipped with a condenser, an internal thermometer and a nitrogen injection line, 0.05 molar equivalent of 4-dimethylaminopyridine (DMAP) and 3.0 molar equivalent of di-tert-butyldicarbonate (DBDC) were added and dissolved in methylene chloride. Subsequently, the temperature inside the reactor was maintained at 0° C. to 5° C. using an ice bath under a nitrogen atmosphere. A solution prepared by dissolving 1.0 molar equivalent of each of dicrotonoamine (Example II-B3-1, m+n=3, $R_1$ and $R_3$ are all hydrogen atoms, and $R_2$ is methyl in Formula 11) of isosorbide-ethylene glycol (Preparation Example I-1: ethylene oxide 3 mole adduct), dicrotonoamine (Example II-B3-2, m+n=5, $R_1$ and $R_3$ are all hydrogen atoms, and $R_2$ is methyl in Formula 11) of isosorbide-ethylene glycol (Preparation Example 1-2: ethylene oxide 5 mole adduct), dicrotonoamine (Example II-B3-3, m+n=10, $R_1$ and $R_3$ are all hydrogen atoms, and $R_2$ is methyl in Formula 11) of isosorbide-ethylene glycol (Preparation Example I-3: ethylene oxide 10 mole adduct) and dicrotonoamine (Example II-B3-4, m+n=25, $R_1$ and $R_3$ are all hydrogen atoms, and $R_2$ is methyl in Formula 11) of isosorbide-ethylene glycol (Preparation Example I-4: ethylene oxide 25 mole adduct) prepared in Examples II-B3-1 to II-B3-4 in 200 ml of methylene chloride was added dropwise to the reactor, at which time the temperature inside the reactor was kept at 0° C. to 5° C. After the dropwise addition was completed, the temperature inside the reactor was raised to 25° C., and the reaction was performed for 3 hours.

Methylene chloride was removed from the obtained reaction products using a concentrator, and the reaction products were extracted using hexane and tertiary distilled water. After removing moisture from the extract using magnesium sulfate, hexane was removed from the extract using a concentrator to obtain dicrotonoisocyanate (Example II-C3-1, m+n=3, $R_1$ and $R_3$ are all hydrogen atoms, and $R_2$ is methyl in Formula 12) of isosorbide-ethylene glycol (Preparation Example I-1: ethylene oxide 3 mole adduct), dicrotonoisocyanate (Example II-C3-2, m+n=5, $R_1$ and $R_3$ are all hydrogen atoms, and $R_2$ is methyl in Formula 12) of isosorbide-ethylene glycol (Preparation Example I-2: ethylene oxide 5 mole adduct), dicrotonoisocyanate (Example II-C3-3, m+n=10, $R_1$ and $R_3$ are all hydrogen atoms, and $R_2$ is methyl in Formula 12) of isosorbide-ethylene glycol (Preparation Example I-3: ethylene oxide 10 mole adduct) and dicrotonoisocyanate (Example II-C3-4, m+n=25, $R_1$ and $R_3$ are all hydrogen atoms, and $R_2$ is methyl in Formula 12) of isosorbide-ethylene glycol (Preparation Example I-4: ethylene oxide 25 mole adduct), respectively, in a yield of 80% to 90%.

As a result of confirming the isocyanate content in the dicrotonoisocyanate of isosorbide-ethylene glycol obtained in Examples II-C3-1 to II-C3-4 through the method of measuring the potential difference of ISO 14896, it was confirmed that Example II-C3-1 is at the level of 17.8+0.1 mass $\%_{NCO}$ (theoretical value=17.8 mass $\%_{NCO}$), Example II-C3-2 is at the level of 14.9+0.1 mass $\%_{NCO}$ (theoretical value=15.0 mass $\%_{NCO}$), Example II-C3-3 is at the level of 10.5+0.3 mass $\%_{NCO}$ (theoretical value=10.8 mass $\%_{NCO}$) and Example II-C3-4 is at the level of 5.7+0.1 mass $\%_{NCO}$ (theoretical value=5.8 mass $\%_{NCO}$). The mass $\%_{NCO}$, which is a unit of the isocyanate content, refers to the mass % of the NCO group present in the sample, dicrotonoisocyanate of isosorbide-ethylene glycol.

Examples II-C4-1 to II-C4-4: Preparation of Dimethacryloisocyanate of Isosorbide-Ethylene Glycol After adding 300 ml of methylene chloride to a 4-neck reactor equipped with a condenser, an internal thermometer and a nitrogen injection line, 0.05 molar equivalent of 4-dimethylaminopyridine (DMAP) and 3.0 molar equivalent of di-tert-butyldicarbonate (DBDC) were added and dissolved in methylene chloride. Subsequently, the temperature inside the reactor was maintained at 0° C. to 5° C. using an ice bath under a nitrogen atmosphere. A solution prepared by dissolving 1.0 molar equivalent of each of dimethacryloamine (Example II-B4-1, m+n=3, $R_1$ and $R_2$ are all hydrogen atoms, and $R_3$ is methyl in Formula 11) of isosorbide-ethylene glycol (Preparation Example I-1: ethylene oxide 3 mole adduct), dimethacryloamine (Example II-B4-2, m+n=5, $R_1$ and $R_2$ are all hydrogen atoms, and $R_3$ is methyl in Formula 11) of isosorbide-ethylene glycol (Preparation Example I-2: ethylene oxide 5 mole adduct), dimethacryloamine (Example II-B4-3, m+n=10, $R_1$ and $R_2$ are all hydrogen atoms, and $R_3$ is methyl in Formula 11) of isosorbide-ethylene glycol (Preparation Example I-3: ethylene oxide 10 mole adduct) and dimethacryloamine (Example II-B4-4, m+n=25, $R_1$ and $R_2$ are all hydrogen atoms, and $R_3$ is methyl in Formula 11) of isosorbide-ethylene glycol (Preparation Example I-4: ethylene oxide 25 mole adduct) prepared in Examples II-B4-1 to II-B4-4 in 200 ml of methylene chloride was added dropwise to the reactor, at which time the temperature inside the reactor was kept at 0° C. to 5° C. After the dropwise addition was completed, the temperature inside the reactor was raised to 25° C., and the reaction was performed for 3 hours.

Methylene chloride was removed from the obtained reaction products using a concentrator, and the reaction products were extracted using hexane and tertiary distilled water. After removing moisture from the extract using magnesium sulfate, hexane was removed from the extract using a concentrator to obtain dimethacryloisocyanate (Example II-$C_4$-1, m+n=3, $R_1$ and $R_2$ are all hydrogen atoms, and $R_3$ is methyl in Formula 12) of isosorbide-ethylene glycol (Preparation Example I-1: ethylene oxide 3 mole adduct), dimethacryloisocyanate (Example II-C4-2, m+n=5, $R_1$ and $R_2$ are all hydrogen atoms, and $R_3$ is methyl in Formula 12) of isosorbide-ethylene glycol (Preparation Example I-2: ethylene oxide 5 mole adduct), dimethacryloisocyanate (Example II-C4-3, m+n=10, $R_1$ and $R_2$ are all hydrogen atoms, and $R_3$ is methyl in Formula 12) of isosorbide-ethylene glycol (Preparation Example I-3: ethylene oxide 10 mole adduct) and dimethacryloisocyanate (Example II-C4-4, m+n=25, $R_1$ and $R_2$ are all hydrogen atoms, and $R_3$ is methyl in Formula 12) of isosorbide-ethylene glycol (Preparation Example I-4: ethylene oxide 25 mole adduct), respectively, in a yield of 75% to 85%.

As a result of confirming the isocyanate content in the dimethacryloisocyanate of isosorbide-ethylene glycol obtained in Examples II-C4-1 to II-C4-4 through the method of measuring the potential difference of ISO 14896, it was confirmed that Example II-C4-1 is at the level of 17.5+0.3 mass $\%_{NCO}$ (theoretical value=17.8 mass $\%_{NCO}$), Example II-C4-2 is at the level of 15.0+0.2 mass $\%_{NCO}$ (theoretical value=15.0 mass $\%_{NCO}$), Example II-C4-3 is at the level of 10.9+0.3 mass $\%_{NCO}$ (theoretical value=10.8 mass $\%_{NCO}$) and Example II-C4-4 is at the level of 5.9+0.2 mass % NO (theoretical value=5.8 mass $\%_{NCO}$). The mass $\%_{NCO}$, which is a unit of the isocyanate content, refers to the mass % of the NCO group present in the sample, dimethacryloisocyanate of isosorbide-ethylene glycol.

Examples II-C5-1 to II-C5-4: Preparation of Dicinnamoisocyanate of Isosorbide-Propylene Glycol After adding 300 ml of methylene chloride to a 4-neck reactor equipped with a condenser, an internal thermometer and a nitrogen injection line, 0.05 molar equivalent of 4-dimethylaminopyridine (DMAP) and 3.0 molar equivalent of di-tert-butyldicarbonate (DBDC) were added and dissolved in methylene chloride. Subsequently, the temperature inside the reactor was maintained at 0° C. to 5° C. using an ice bath under a nitrogen atmosphere. A solution prepared by dissolving 1.0 molar equivalent of each of dicinnamoamine (Example II-B5-1, m+n=3, $R_1$ is methyl, $R_2$ is phenyl, and $R_3$ is hydrogen atom in Formula 11) of isosorbide-propylene glycol (Preparation Example 2-1: propylene oxide 3 mole adduct), dicinnamoamine (Example II-B5-2, m+n=5, $R_1$ is methyl, $R_2$ is phenyl, and $R_3$ is hydrogen atom in Formula 11) of isosorbide-propylene glycol (Preparation Example 2-2: propylene oxide 5 mole adduct), dicinnamoamine (Example II-B5-3, m+n=10, $R_1$ is methyl, $R_2$ is phenyl, and $R_3$ is hydrogen atom in Formula 11) of isosorbide-propylene glycol (Preparation Example 2-3: propylene oxide 10 mole adduct) and dicinnamoamine (Example II-B5-4, m+n=25, $R_1$ is methyl, $R_2$ is phenyl, and $R_3$ is hydrogen atom in Formula 11) of isosorbide-propylene glycol (Preparation Example 2-4: propylene oxide 25 mole adduct) prepared in Examples II-B5-1 to II-B5-4 in 200 ml of methylene chloride was added dropwise to the reactor, at which time the temperature inside the reactor was kept at 0° C. to 5° C. After the dropwise addition was completed, the temperature inside the reactor was raised to 25° C., and the reaction was performed for 4 hours.

Methylene chloride was removed from the obtained reaction products using a concentrator, and the reaction products were extracted using hexane and tertiary distilled water. After removing moisture from the extract using magnesium sulfate, hexane was removed from the extract using a concentrator to obtain dicinnamoisocyanate (Example II-C5-1, m+n=3, $R_1$ is methyl, $R_2$ is phenyl, and $R_3$ is hydrogen atom in Formula 12) of isosorbide-propylene glycol (Preparation Example 2-1: propylene oxide 3 mole adduct), dicinnamoisocyanate (Example II-C5-2, m+n=5, $R_1$ is methyl, $R_2$ is phenyl, and $R_3$ is hydrogen atom in Formula 12) of isosorbide-propylene glycol (Preparation Example 2-2: propylene oxide 5 mole adduct), dicinnamoisocyanate (Example II-C5-3, m+n=10, $R_1$ is methyl, $R_2$ is phenyl, and $R_3$ is hydrogen atom in Formula 12) of isosorbide-propylene glycol (Preparation Example 2-3: propylene oxide 10 mole adduct) and dicinnamoisocyanate (Example II-C5-4, m+n=25, $R_1$ is methyl, $R_2$ is phenyl, and $R_3$ is hydrogen atom in Formula 12) of isosorbide-propylene glycol (Preparation Example 2-4: propylene oxide 25 mole adduct), respectively, in a yield of 75% to 80%.

As a result of confirming the isocyanate content in the dicinnamoisocyanate of isosorbide-propylene glycol obtained in Examples II-C5-1 to II-C5-4 through the method of measuring the potential difference of ISO 14896, it was confirmed that Example II-C5-1 is at the level of 13.5+0.3 mass $\%_{NCO}$ (theoretical value=13.2 mass $\%_{NCO}$), Example II-C5-2 is at the level of 11.3+0.2 mass $\%_{NCO}$ (theoretical value=11.1 mass $\%_{NCO}$), Example II-C5-3 is at the level of 8.0+0.3 mass $\%_{NCO}$ (theoretical value=8.0 mass $\%_{NCO}$) and Example II-C5-4 is at the level of 4.2+0.2 mass $\%_{NCO}$ (theoretical value=4.4 mass $\%_{NCO}$). The mass $\%_{NCO}$, which is a unit of the isocyanate content, refers to the mass % of the NCO group present in the sample, dicinnamoisocyanate of isosorbide-propylene glycol.

Examples II-C6-1 to II-C6-4: Preparation of Di(3-Furyl)Acryloisocyanate of Isosorbide-Ethylene Glycol After adding 300 ml of methylene chloride to a 4-neck reactor equipped with a condenser, an internal thermometer and a nitrogen injection line, 0.05 molar equivalent of 4-dimethylaminopyridine (DMAP) and 3.0 molar equivalent of di-tert-butyldicarbonate (DBDC) were added and dissolved in methylene chloride. Subsequently, the temperature inside the reactor was maintained at 0° C. to 5° C. using an ice bath under a nitrogen atmosphere. A solution prepared by dissolving 1.0 molar equivalent of each of di(3-furyl)acryloamine (Example II-B6-1, m+n=3, $R_1$ and $R_3$ are all hydrogen atoms, and $R_2$ is furyl in Formula 11) of isosorbide-ethylene glycol (Preparation Example I-1: ethylene oxide 3 mole adduct), di(3-furyl)acryloamine (Example II-B6-2, m+n=5, $R_1$ and $R_3$ are all hydrogen atoms, and $R_2$ is furyl in Formula 11) of isosorbide-ethylene glycol (Preparation Example I-2: ethylene oxide 5 mole adduct), di(3-furyl) acryloamine (Example II-B6-3, m+n=10, $R_1$ and $R_3$ are all hydrogen atoms, and $R_2$ is furyl in Formula 11) of isosorbide-ethylene glycol (Preparation Example I-3: ethylene oxide 10 mole adduct) and di(3-furyl)acryloamine (Example II-B6-4, m+n=25, $R_1$ and $R_3$ are all hydrogen atoms, and $R_2$ is furyl in Formula 11) of isosorbide-ethylene glycol (Preparation Example I-4: ethylene oxide 25 mole adduct) prepared in Examples II-B6-1 to II-B6-4 in 200 ml of methylene chloride was added dropwise to the reactor, at which time the temperature inside the reactor was kept at 0° C. to 5° C. After the dropwise addition was completed, the temperature inside the reactor was raised to 25° C., and the reaction was performed for 3 hours.

Methylene chloride was removed from the obtained reaction products using a concentrator, and the reaction products were extracted using hexane and tertiary distilled water. After removing moisture from the extract using magnesium sulfate, hexane was removed from the extract using a concentrator to obtain di(3-furyl)acryloisocyanate (Example II-C6-1, m+n=3, $R_1$ and $R_3$ are all hydrogen atoms, and $R_2$ is furyl in Formula 12) of isosorbide-ethylene glycol (Preparation Example I-1: ethylene oxide 3 mole adduct), di(3-furyl)acryloisocyanate (Example II-C6-2, m+n=5, $R_1$ and $R_3$ are all hydrogen atoms, and $R_2$ is furyl in Formula 12) of isosorbide-ethylene glycol (Preparation Example I-2: ethylene oxide 5 mole adduct), di(3-furyl)acryloisocyanate (Example II-C6-3, m+n=10, $R_1$ and $R_3$ are all hydrogen atoms, and $R_2$ is furyl in Formula 12) of isosorbide-ethylene glycol (Preparation Example I-3: ethylene oxide 10 mole adduct) and di(3-furyl)acryloisocyanate (Example II-$C_6$-4, m+n=25, $R_1$ and $R_3$ are all hydrogen atoms, and $R_2$ is furyl in Formula 12) of isosorbide-ethylene glycol (Preparation Example I-4: ethylene oxide 25 mole adduct), respectively, in a yield of 70% to 80%.

As a result of confirming the isocyanate content in the di(3-furyl)acryloisocyanate of isosorbide-ethylene glycol obtained in Examples II-C6-1 to II-C6-4 through the method of measuring the potential difference of ISO 14896, it was confirmed that Example II-C6-1 is at the level of 14.8+0.3 mass $\%_{NCO}$ (theoretical value=14.6 mass $\%_{NCO}$), Example II-C6-2 is at the level of 12.7+0.2 mass $\%_{NCO}$ (theoretical value=12.6 mass $\%_{NCO}$), Example II-C6-3 is at the level of 9.5+0.1 mass $\%_{NCO}$ (theoretical value=9.5 mass $\%_{NCO}$) and Example II-C6-4 is at the level of 5.2+0.3 mass $\%_{NCO}$ (theoretical value=5.4 mass $\%_{NCO}$). The mass $\%_{NCO}$, which is a unit of the isocyanate content, refers to the mass % of the NCO group present in the sample, di(3-furyl)acryloisocyanate of isosorbide-ethylene glycol.

Examples II-C7-1 to II-C7-4: Preparation of Di(3-Cyclohexyl)Acryloisocyanate of Isosorbide-Propylene Glycol After adding 300 ml of methylene chloride to a 4-neck reactor equipped with a condenser, an internal thermometer and a nitrogen injection line, 0.05 molar equivalent of 4-dimethylaminopyridine (DMAP) and 3.0 molar equivalent of di-tert-butyldicarbonate (DBDC) were added and dissolved in methylene chloride. Subsequently, the temperature inside the reactor was maintained at 0° C. to 5° C. using an ice bath under a nitrogen atmosphere. A solution prepared by dissolving 1.0 molar equivalent of each of di(3-cyclohexyl) acryloamine (Example II-B7-1, m+n=3, $R_1$ is methyl, $R_2$ is cyclohexyl, and $R_3$ is hydrogen atom in Formula 11) of isosorbide-propylene glycol (Preparation Example 2-1: propylene oxide 3 mole adduct), di(3-cyclohexyl)acryloamine (Example II-B7-2, m+n=5, $R_1$ is methyl, $R_2$ is cyclohexyl, and $R_3$ is hydrogen atom in Formula 11) of isosorbide-propylene glycol (Preparation Example 2-2: propylene oxide 5 mole adduct), di(3-cyclohexyl)acryloamine (Example II-B7-3, m+n=10, $R_1$ is methyl, $R_2$ is cyclohexyl, and $R_3$ is hydrogen atom in Formula 11) of isosorbide-propylene glycol (Preparation Example 2-3: propylene oxide 10 mole adduct) and di(3-cyclohexyl)acryloamine (Example II-B7-4, m+n=25, $R_1$ is methyl, $R_2$ is cyclohexyl, and $R_3$ is hydrogen atom in Formula 11) of isosorbide-propylene glycol (Preparation Example 2-4: propylene oxide 25 mole adduct) prepared in Examples II-B7-1 to II-B7-4 in 200 ml of methylene chloride was added dropwise to the reactor, at which time the temperature inside the reactor was kept at 0° C. to 5° C. After the dropwise addition was completed, the temperature inside the reactor was raised to 25° C., and the reaction was performed for 4 hours.

Methylene chloride was removed from the obtained reaction products using a concentrator, and the reaction products were extracted using hexane and tertiary distilled water. After removing moisture from the extract using magnesium sulfate, hexane was removed from the extract using a concentrator to obtain di(3-cyclohexyl)acryloisocyanate (Example II-C7-1, m+n=3, $R_1$ is methyl, $R_2$ is cyclohexyl, and $R_3$ is hydrogen atom in Formula 12) of isosorbide-propylene glycol (Preparation Example 2-1: propylene oxide 3 mole adduct), di(3-cyclohexyl)acryloisocyanate (Example II-C7-2, m+n=5, $R_1$ is methyl, $R_2$ is cyclohexyl, and $R_3$ is hydrogen atom in Formula 12) of isosorbide-propylene glycol (Preparation Example 2-2: propylene oxide 5 mole adduct), di(3-cyclohexyl)acryloisocyanate (Example II-C7-3, m+n=10, $R_1$ is methyl, $R_2$ is cyclohexyl, and $R_3$ is hydrogen atom in Formula 12) of isosorbide-propylene glycol (Preparation Example 2-3: propylene oxide 10 mole adduct) and di(3-cyclohexyl)acryloisocyanate (Example II-C7-4, m+n=25, $R_1$ is methyl, $R_2$ is cyclohexyl, and $R_3$ is hydrogen atom in Formula 12) of isosorbide-propylene glycol (Preparation Example 2-4: propylene oxide 25 mole adduct), respectively, in a yield of 80% to 90%.

As a result of confirming the isocyanate content in the di(3-cyclohexyl)acryloisocyanate of isosorbide-propylene glycol obtained in Examples II-C7-1 to II-C7-4 through the method of measuring the potential difference of ISO 14896, it was confirmed that Example II-C7-1 is at the level of 12.9+0.1 mass $\%_{NCO}$ (theoretical value=12.9 mass $\%_{NCO}$), Example II-C7-2 is at the level of 11.2+0.3 mass $\%_{NCO}$ (theoretical value=11.2 mass $\%_{NCO}$), Example II-C7-3 is at the level of 7.9+0.1 mass $\%_{NCO}$ (theoretical value=7.9 mass $\%_{NCO}$) and Example II-C7-4 is at the level of 4.3+0.2 mass $\%_{NCO}$ (theoretical value =4.4 mass $\%_{NCO}$). The mass $\%_{NCO}$, which is a unit of the isocyanate content, refers to the mass % of the NCO group present in the sample, di(3-cyclohexyl) acryloisocyanate of isosorbide-propylene glycol.

Examples II-D1-1 to II-D1-4: Preparation of Dipropylisocyanate of Isosorbide-Ethylene Glycol (Using Triphosgene)

After adding 30 ml of methylene chloride into a reactor equipped with a phosgene gas inlet, an internal thermometer, a dropping funnel, a dry ice cooling condenser and a gas discharge line connected to a hood line, the temperature inside the reactor was cooled to −50° C. using dry ice and maintained. Then, after connecting the phosgene generating device comprising 1 molar equivalent of triphosgene and the reactor with a hose, the phosgene generating device was heated to 100° C. using an oil bath, and 1.0 molar equivalent of each of diacryloamine (Example II-B1-1, m+n=3, $R_1$, $R_2$ and $R_3$ are all hydrogen atoms in Formula 11) of isosorbide-ethylene glycol (Preparation Example I-1: ethylene oxide 3 mole adduct), diacryloamine (Example II-B1-2, m+n=5, $R_1$, $R_2$ and $R_3$ are all hydrogen atoms in Formula 11) of isosorbide-ethylene glycol (Preparation Example I-2: ethylene oxide 5 mole adduct), diacryloamine (Example II-B1-3, m+n=10, $R_1$, $R_2$ and $R_5$ are all hydrogen atoms in Formula 11) of isosorbide-ethylene glycol (Preparation Example I-3: ethylene oxide 10 mole adduct) and diacryloamine (Example II-B1-4, m+n=25, $R_1$, $R_2$ and $R_3$ are all hydrogen atoms in Formula 11) of isosorbide-ethylene glycol (Preparation Example I-4: ethylene oxide 25 mole adduct) prepared in Examples II-B1-1 to II-B1-4 were slowly added dropwise and stirred vigorously, and the temperature inside the reactor was maintained at −30° C. Thereafter, a mixed solution obtained by dissolving 3 molar equivalents of triethylamine in 200 ml of methylene chloride was slowly added dropwise so that the temperature inside the reactor was maintained at −25° C. to −30° C. After the dropwise addition was completed, the temperature inside the reactor was raised and reacted at 0° C. for 30 minutes.

Methylene chloride was removed from the reaction product obtained by using a concentrator, and the reaction product was dissolved in hexane and washed 3 times with IN HCl solution, 1 time with IN NaOH solution and 3 times with tertiary distilled water. Then, water in the organic layer was removed using magnesium sulfate, and hexane was removed from the extract using a concentrator to obtain dipropylisocyanate (Example II-D1-1, m+n=3, $R_1$, $R_2$ and $R_5$ are all hydrogen atoms in Formula 12) of isosorbide-ethylene glycol (Preparation Example I-1: ethylene oxide 3 mole adduct), dipropylisocyanate (Example II-D1-2, m+n=5, $R_1$, $R_2$ and $R_3$ are all hydrogen atoms in Formula 12) of isosorbide-ethylene glycol (Preparation Example I-2: ethylene oxide 5 mole adduct), dipropylisocyanate (Example II-D1-3, m+n=10, $R_1$, $R_2$ and $R_3$ are all hydrogen atoms in Formula 12) of isosorbide-ethylene glycol (Preparation Example I-3: ethylene oxide 10 mole adduct) and dipropylisocyanate (Example II-D1-4, m+n=25, $R_1$, $R_2$ and $R_5$ are all hydrogen atoms in Formula 12) of isosorbide-ethylene glycol (Preparation Example I-4: ethylene oxide 25 mole adduct), respectively, in a yield of 85% to 95%.

As a result of confirming the isocyanate content in the dipropylisocyanate of isosorbide-ethylene glycol obtained in Examples II-D1-1 to II-D1-4 through the method of measuring the potential difference of ISO 14896, it was confirmed that Example II-D1-1 is at the level of 19.0+0.1 mass % NO (theoretical value=18.9 mass $\%_{NCO}$), Example II-D1-2 is at the level of 15.7+0.2 mass $\%_{NCO}$ (theoretical value=15.8 mass % NO), Example II-D1-3 is at the level of 11.1+0.2 mass $\%_{NCO}$ (theoretical value=11.1 mass $\%_{NCO}$) and Example II-D1-4 is at the level of 5.8+0.2 mass $\%_{NCO}$ (theoretical value=5.9 mass $\%_{NCO}$). The mass $\%_{NCO}$, which is a unit of the isocyanate content, refers to the mass % of the NCO group present in the sample, dipropylisocyanate of isosorbide-ethylene glycol.

<Preparation of Polymer Comprising Diisocyanate Compound (Compound of Formula A) Comprising Dianhydrohexitol and an Alkylene Oxide Extension>

Examples II-E1 to II-E8: Preparation of Polyurethane Foam Using the Compounds of Examples II-C1-1 to II-C7-1 and II-D1-1

According to the components and content ratios shown in Table 2 below, a polyol, a surfactant, a catalyst and a blowing agent were mixed and sufficiently stirred at a stirring speed of 3,000 rpm for 1 to 3 minutes to prepare a polyol premix composition (first component).

To the prepared polyol premix composition (first component), the compounds of II-$C_1$-1 to II-C7-1 and II-D1-1 prepared in Examples II-C1-1 to II-C7-1 and II-D1-1, respectively, were added as a polyisocyanate component (second component), and the mixtures were stirred for 7 seconds to 10 seconds at a stirring speed of 3,000 rpm to prepare a composition for forming a two-component polyurethane foam.

Subsequently, a polyethylene film was coated on a square box mold of 250 mm×250 mm in a square shape, and the prepared composition for forming a two-component polyurethane foam was poured thereon. At this time, the reaction initiation time (cream time), the maximum volume arrival time (rise time) and the gel time were measured and recorded using a second clock, and it was observed whether or not health bubbles were generated. As a result of checking the heat of curing reaction of the polyurethane foam with a bar thermometer, it was confirmed that it was 120° C. to 130° C. Thereafter, physical properties of the prepared polyurethane foam specimens were measured by the following evaluation method, and the results are shown in Table 2 below.

Comparative Example II-E1: Preparation of Polyurethane Foam Using Toluene Diisocyanate (TDI)

Except that toluene diisocyanate (TDI) was used as the polyisocyanate component (second component), a polyurethane foam specimen was prepared in the same manner as in Examples II-E1 to II-E8. Physical properties of the prepared polyurethane foam specimen were measured by the following evaluation method, and the results are shown in Table 2 below.

Comparative Example II-E2: Preparation of Polyurethane Foam Using 4,4-Diphenylmethylene Diisocyanate (MDI)

Except that 4,4'-diphenylmethylene diisocyanate (MDI) was used as the polyisocyanate component (second component), a polyurethane foam specimen was prepared in the same manner as in Examples II-E1 to II-E8. Physical properties of the prepared polyurethane foam specimen were measured by the following evaluation method, and the results are shown in Table 2 below.

<Used ingredients >

1) Polyol

PPG-3022: Trifunctional polyether polyol with an active hydrogen equivalent of 3,000 and a hydroxyl value of 54 to 58 mgKOH/g (PPG-3022 from Kumho Petrochemical) 2) Silicone surfactant L-580K: Polyalkyleneoxide methylsiloxane copolymer (Niax L-580K from Momentive)

3) Amine catalyst

-L-33: Triethylenediamine/dipropylene glycol solution at a concentration of 67% by weight (TEDA L-33 from Tosoh Corporation)

-A-1: Bis-(20dimethylaminoethyl)ether/propylene glycol solution at a concentration of 70% by weight (Niax Catalyst A-1 from Momentive)

4) Organometallic catalyst

DBTDL: organometallic catalyst (DBTDL from Sigma Aldrich)

5) Blowing agent

Water

6) Polyisocyanate component

① T-80: Toluene diisocyanate (TDI) (2,4-/2,6-isomer ratio=80:20) (Lupranate T-80 from BASF Korea)

② ME: 4,4-diphenylmethylene diisocyanate (MDI) (Lupranate ME product from BASF Korea)

③ SYC-ISO1.1: Diisocyanate compound of Example II-C1-1

④ SYC-ISO2.1: Diisocyanate compound of Example II-C2-1

⑤ SYC-ISO3.1: Diisocyanate compound of Example II-C3-1

⑥ SYC-ISO4.1: Diisocyanate compound of Example II-C4-1

⑦ SYC-ISO5.1: Diisocyanate compound of Example II-C5-1

⑧ SYC-ISO6.1: Diisocyanate compound of Example II-C6-1

⑨ SYC-ISO7.1: Diisocyanate compound of Example II-C7-1

⑩ SYC-ISO8.1: Diisocyanate compound of Example II-D1-1

Method of Measuring Physical Properties

A description of the physical properties described in Table 2 is as follows.

1) Cream time (seconds): shows the time taken from when the polyurethane foam stock solution is mixed until the stock solution starts to swell, and it is important to find a balance because this is the part that finds optimum reactivity. The fast and slow of the cream time is not important, but the short cream time is preferable because the longer cream time can result in irregular foam formation (or cell formation). However, too short a cream time may result in poor mixing, so a suitable cream time (e.g., 7 to 14 seconds) is required.

2) Rise time (seconds): shows the time taken from when polyurethane foam stock solution is mixed until the stock solution reaches to the maximum swelling of the foam. Rise time is the part that finds optimum reactivity, and it is important to balance between gelling and blowing, so it is hard to say good or bad just because of the fast and slow rise time. If the rise time is fast, the foam collapses (decayed before the foamed foam hardens, usually due to an incorrect stock solution ratio or insufficient mixing of raw materials), and if it is too slow, foaming may not be possible due to gelling (foaming of foam is stopped) during foaming. Therefore, a suitable rise time (e.g., 108 seconds to 124 seconds) is required. “Unmeasurable” of rise time means that the composition (stock solution) does not swell and no foam is formed.

3) Gel time: shows the time taken from the time when the polyurethane stock solution is mixed to the time when the stock solution has a gel strength that can withstand a light impact and has a stable spatial shape-specifically, the time when at least three or four urethane fibers come out when a foam in reaction is poked with wooden chopsticks.

4) Health bubbles: shows small bubbles that burst on the surface of the foam immediately after swelling to the maximum, and the presence of health bubbles means that foam foaming is correct.

O: Health bubbles exist x: Health bubbles do not exist

5) Foam state:

Good: The foam is blown (swollen), and it refers to a condition in which no collapse, cracks (cracking inside the foam due to external conditions during the formation of the foam or after the formation of the foam) or shrinkages (a phenomenon wherein the size of the foam is smaller than its original size by being cooled the gas trapped inside the foam) are apparent due to the gelling.

Bad: The foam does not form due to the bursting of cells while the foam is blowing.

6) Molding density: Measured according to ASTM D 1621.

7) Hardness: Measured according to KS M 6672.

8) Tensile strength: Measured according to KS M 6518.

9) Elongation: Measured according to KS M 6518.

TABLE 2

| Categories | | | Comparative Example | | Example | | | | | | | |
|---|---|---|---|---|---|---|---|---|---|---|---|---|
| | | | II-E1 | II-E2 | II-E1 | II-E2 | II-E3 | II-E4 | II-E5 | II-E6 | II-E7 | II-E8 |
| Component | Polyol | PPG-3022 | 100 | 100 | 100 | 100 | 100 | 100 | 100 | 100 | 100 | 100 |
| (parts by | Surfactant | L-580K | 1.2 | 1.2 | 1.2 | 1.2 | 1.2 | 1.2 | 1.2 | 1.2 | 1.2 | 1.2 |

TABLE 2-continued

| Categories | | | Comparative Example II-E1 | Comparative Example II-E2 | Example II-E1 | Example II-E2 | Example II-E3 | Example II-E4 | Example II-E5 | Example II-E6 | Example II-E7 | Example II-E8 |
|---|---|---|---|---|---|---|---|---|---|---|---|---|
| weight) | Catalyst | A-1 | 0.13 | 0.13 | 0.19 | 0.20 | 0.17 | 0.17 | 0.20 | 0.19 | 0.16 | 0.19 |
| | | L-33 | 0.5 | 0.5 | 0.5 | 0.5 | 0.5 | 0.5 | 0.5 | 0.5 | 0.5 | 0.5 |
| | | DBTDL | 0.12 | 0.12 | 0.12 | 0.14 | 0.17 | 0.17 | 0.19 | 0.18 | 0.20 | 0.12 |
| | Blowing agent | Water | 0.9 | 0.9 | 1.5 | 1.5 | 1.5 | 1.5 | 1.8 | 1.8 | 2.0 | 1.5 |
| | Polyiso-cyanate | T-80 | 19.2 | — | — | — | — | — | — | — | — | — |
| | | ME | — | 27.5 | — | — | — | — | — | — | — | — |
| | | SYC-ISO1.1 | — | — | 48.9 | — | — | — | — | — | — | — |
| | | SYC-ISO2.1 | — | — | — | 53.5 | — | — | — | — | — | — |
| | | SYC-ISO3.1 | — | — | — | — | 51.9 | — | — | — | — | — |
| | | SYC-ISO4.1 | — | — | — | — | — | 51.9 | — | — | — | — |
| | | SYC-ISO5.1 | — | — | — | — | — | — | 70.2 | — | — | — |
| | | SYC-ISO6.1 | — | — | — | — | — | — | — | 63.3 | — | — |
| | | SYC-ISO7.1 | — | — | — | — | — | — | — | — | 71.5 | — |
| | | SYC-ISO8.1 | — | — | — | — | — | — | — | — | — | 48.9 |
| Properties | Isocyanate index | | 110 | 110 | 110 | 110 | 110 | 110 | 110 | 110 | 110 | 110 |
| | Cream time (sec) | | 11 | 10 | 11 | 11 | 12 | 12 | 14 | 13 | 14 | 11 |
| | Rise time (sec) | | 116 | 106 | 110 | 112 | 118 | 119 | 122 | 119 | 124 | 108 |
| | Gel time (sec) | | 89 | 80 | 90 | 92 | 78 | 80 | 75 | 82 | 72 | 91 |
| | Molding density (kg/m$^3$) | | 34.7 | 35.3 | 35.3 | 35.5 | 34.9 | 34.5 | 34.9 | 35.2 | 35.0 | 35.1 |
| | Hardness (25%, CLD)(kgf) | | 7.2 | 8.5 | 7.3 | 6.9 | 7.2 | 7.5 | 9.0 | 8.8 | 8.6 | 7.3 |
| | Health bubbles | | ○ | ○ | ○ | ○ | ○ | ○ | ○ | ○ | ○ | ○ |
| | Tensile strength (kg/cm$^3$) | | 1.65 | 1.29 | 1.32 | 1.29 | 1.27 | 1.26 | 1.70 | 1.68 | 1.69 | 1.36 |
| | Elongation (%) | | 130 | 140 | 210 | 220 | 220 | 220 | 190 | 190 | 200 | 210 |
| | Foam state | | Good | Good | Good | Good | Good | Good | Good | Good | Good | Good |

As shown in Table 2, in the case of the polyurethane foams of Examples II-E1 to II-E8 prepared using the diisocyanate compound represented by Formula A according to the present invention as a polyisocyanate component, the molding density was about 35 kg/m$^3$, the tensile strength was 1.2 kg/cm$^3$ or more and the elongation was 190% or more, indicating excellent foam properties.

On the other hand, in the case of the polyurethane foams of Comparative Examples II-E1 and II-E2 prepared using TDI and MDI, which are diisocyanate compounds commonly used as polyisocyanate components in the manufacture of polyurethane foams, the molding density was about 35 kg/m$^3$, the tensile strength was 1.2 kg/cm$^3$ or more, but the elongation was 130% to 140%, which was inferior to that of the polyurethane foams of Examples II-E1 to II-E8.

In particular, when comparing Examples II-E5 to II-E7 and Comparative Example II-E1 having similar tensile strength of 1.6 kg/cm$^3$ to 1.7 kg/cm$^3$, the polyurethanes foam of Examples II-E5 to II-E7 exhibits the elongation of 190% to 200%, higher than the elongation of 130% of Comparative Example II-E1. From this, in terms of toughness in proportion to the elongation and tensile strength, it can be seen that the polyurethane foam of the Example exhibits higher toughness than the polyurethane foam of the Comparative Example.

In addition, even when comparing Examples II-E1 to II-E4 and II-E8 and Comparative Example II-E2 having a similar tensile strength of 1.2 kg/cm$^3$ to 1.3 kg/cm$^3$, the elongation of the polyurethane foam of Examples II-E1 to II-E4 and II-E8 was 210% to 220%, which was significantly higher than the 140% of Comparative Example II-E2. From this, it can also be seen that the polyurethane foam of the Example exhibits higher toughness than the polyurethane foam of the Comparative Example.

The invention claimed is:

1. A compound represented by the following Formula A:

X—Y—O—M—O—Y'—X [Formula A]

in Formula A, each X is independently —$CH_2NCO$,

Y is —$[CH_2CHR_{10}]_m$—$CHR_2CHR_3$—,

Y' is —$[CH_2CHR_1O]_n$—$CHR_2CHR_3$—, wherein each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, M is a divalent organic group derived from anhydrosugar alcohol, and wherein M is a divalent organic group derived from isosorbide, isomannide or isoidide.

2. The compound according to claim 1, wherein m+n is an integer from 1 to 25.

3. The compound according to claim 1, wherein M is selected from the following formula:

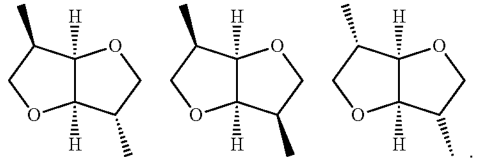

4. The compound according to claim 1, represented by the following Formula 3:

[Formula 3]

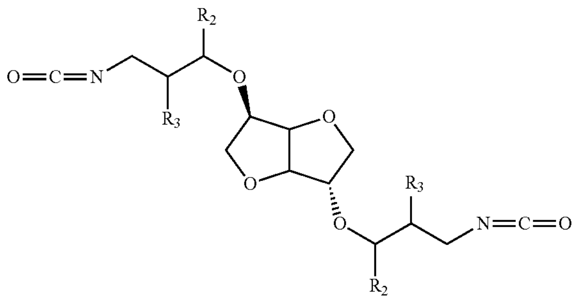

in Formula 3, each of $R_2$ and $R_3$ is independently hydrogen, alkyl, aryl, heteroaryl or cycloalkyl.

5. The compound according to claim 1, represented by the following Formula 6:

[Formula 6]

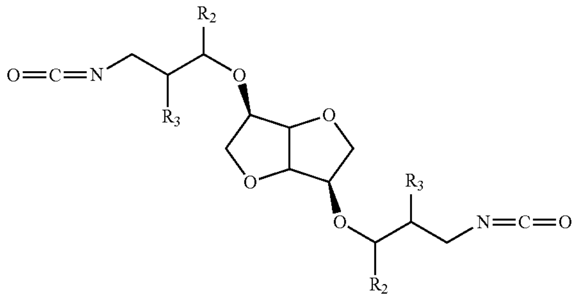

in Formula 6, each of $R_2$ and $R_3$ is independently hydrogen, alkyl, aryl, heteroaryl or cycloalkyl.

6. The compound according to claim 1, represented by the following Formula 9:

[Formula 9]

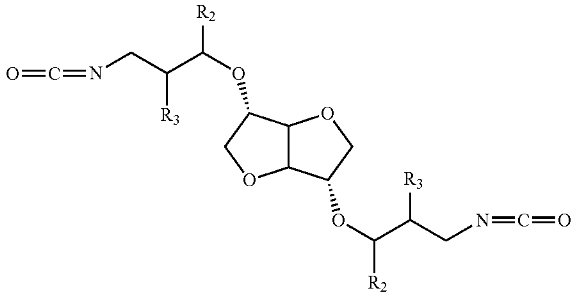

in Formula 9, each of $R_2$ and $R_3$ is independently hydrogen, alkyl, aryl, heteroaryl or cycloalkyl.

7. The compound according to claim 1, represented by the following Formula 12:

[Formula 12]

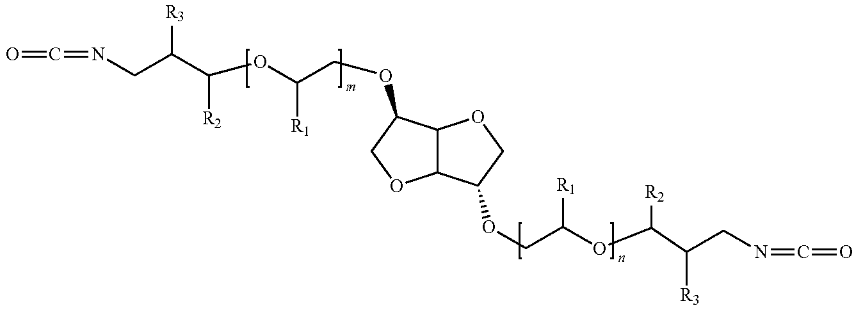

in Formula 12, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

8. The compound according to claim 1, represented by the following Formula

[Formula 15]

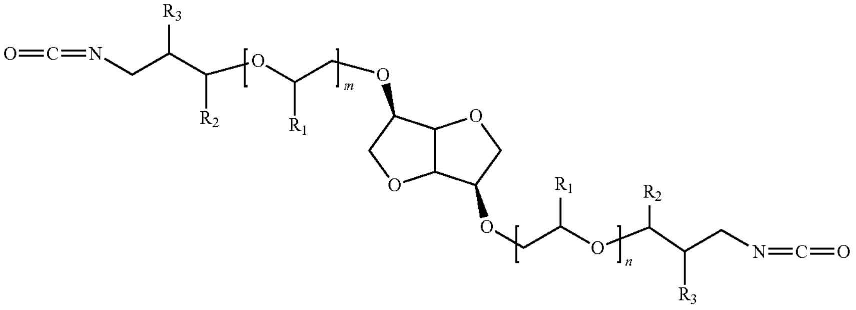

in Formula 15, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

9. The compound according to claim 1, represented by the following Formula 18:

[Formula 18]

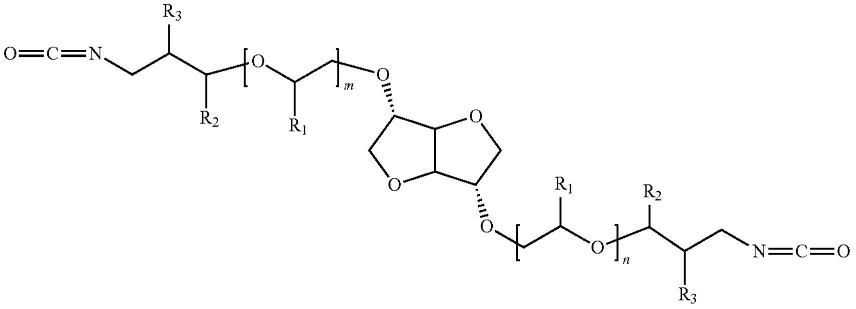

in Formula 18, each $R_1$ is independently hydrogen, alkyl or aryl, each of $R_2$ and $R_3$ is independently hydrogen, alkyl, aryl, heteroaryl or cycloalkyl, each of m and n is independently an integer of 0 to 15, and m+n is an integer from 1 to 25.

10. A method for preparing a compound represented by Formula A according to claim 1, comprising (1) a step of performing Michael reaction of anhydrosugar alcohol or anhydrosugar alcohol-alkylene glycol with a nitrile compound;

(2) a step of adding hydrogen to the compound obtained from the Michael reaction; and (3) a step of converting the terminal group of the compound obtained from the hydrogenation into an isocyanate.

11. The method for preparing a compound represented by Formula A according to claim 10, wherein the nitrile compound in step (1) is selected from the group consisting of acrylonitrile, crotononitrile, methacrylonitrile, cinnamonitrile, 3-(furan-2-yl)prop-2-enenitrile, cyclohexaneacrylonitrile or a combination thereof.

12. The method for preparing a compound represented by Formula A according to claim 10, wherein in step (1), 1 to 10 molar equivalents of a nitrile compound is reacted with 1 molar equivalent of anhydrosugar alcohol or anhydrosugar alcohol-alkylene glycol.

13. The method for preparing a compound represented by Formula A according to claim 10, wherein in step (1), Michael reaction is performed in the presence of 0.005 to 0.05 molar equivalent of a base catalyst with respect to 1 molar equivalent of anhydrosugar alcohol or anhydrosugar alcohol-alkylene glycol.

14. The method for preparing a compound represented by Formula A according to claim 10, further comprising a step of stirring the product of the Michael reaction for 1 to 10 hours after step (1).

15. The method for preparing a compound represented by Formula A according to claim 10, wherein in step (2), hydrogenation is performed under a hydrogen pressure of 5 to 30 bar.

16. The method for preparing a compound represented by Formula A according to claim 10, wherein step (3) is performed by reacting the compound obtained from the hydrogenation with a carbonate-based compound, a phosgene-based compound; carbon monoxide and oxygen; or carbon dioxide.

17. The method for preparing a compound represented by Formula A according to claim 16, wherein the carbonate-based compound is selected from the group consisting of di-tert-butyl dicarbonate, dimethyl dicarbonate, diethyl dicarbonate, dibenzyl dicarbonate, dimethyl carbonate, diethyl carbonate, diphenyl carbonate, ethylmethyl carbonate or a combination thereof, and the phosgene-based compound is selected from the group consisting of phosgene, diphosgene, triphosgene or a combination thereof.

18. The method for preparing a compound represented by Formula A according to claim 10, wherein step (3) is performed in the presence of a catalyst selected from the group consisting of 4-dimethylaminopyridine, zinc acetate, sodium methoxide, trialkylamine, Group Ill metal halide or a combination thereof.

19. A polymer comprising a compound represented by Formula A according to claim 1.

20. The polymer according to claim 19, which is thermoplastic polyurethane (TPU), soft or rigid polyurethane foam, polyurea, polyamide, polyimide, binder resin, thermoplastic polyester elastomer, artificial leather polyurethane or emulsion polymer.

* * * * *